(12) United States Patent
Kumamoto et al.

(10) Patent No.: US 8,256,412 B2
(45) Date of Patent: Sep. 4, 2012

(54) WARMING TOOL IN A SHEET FORM

(75) Inventors: Yoshiaki Kumamoto, Tochigi (JP); Masataka Ishikawa, Tochigi (JP); Hironobu Kawajiri, Tochigi (JP); Hisao Nishiguchi, Tokyo (JP)

(73) Assignee: Kao Corporation, Tokyo (JP)

( * ) Notice: Subject to any disclaimer, the term of this patent is extended or adjusted under 35 U.S.C. 154(b) by 1278 days.

(21) Appl. No.: 10/566,471

(22) PCT Filed: Jul. 29, 2004

(86) PCT No.: PCT/JP2004/010800
§ 371 (c)(1),
(2), (4) Date: Sep. 20, 2006

(87) PCT Pub. No.: WO2005/011543
PCT Pub. Date: Feb. 10, 2005

(65) Prior Publication Data
US 2007/0020412 A1  Jan. 25, 2007

(30) Foreign Application Priority Data

| | | |
|---|---|---|
| Jul. 31, 2003 | (JP) | 2003-204966 |
| Aug. 8, 2003 | (JP) | 2003-206865 |
| Aug. 8, 2003 | (JP) | 2003-206866 |
| Oct. 16, 2003 | (JP) | 2003-356907 |
| Feb. 6, 2004 | (JP) | 2004-031360 |
| Feb. 6, 2004 | (JP) | 2004-031361 |
| Feb. 10, 2004 | (JP) | 2004-034169 |
| Feb. 10, 2004 | (JP) | 2004-034170 |

(51) Int. Cl.
*A61F 7/08* (2006.01)
*D21J 3/00* (2006.01)

(52) U.S. Cl. ............... 126/263.02; 126/204; 126/205; 126/206; 126/263.01; 126/263.07; 165/46; 383/901

(58) Field of Classification Search ..... 126/263–263.09, 126/204–207; 165/46; 383/901; *A61F 7/08; D21J 3/00*
See application file for complete search history.

(56) References Cited

U.S. PATENT DOCUMENTS 301,931 A * 7/1884 Smith et al. .............. 165/46
(Continued)

FOREIGN PATENT DOCUMENTS

EP     0 370 600 A1    5/1990
(Continued)

OTHER PUBLICATIONS

File "JP2572621B_MT.pdf" Machine Translation; Apr. 22, 2010 (Machine Translation: JP-2572621, Translated Apr. 22, 2010).*

(Continued)

*Primary Examiner* — Steven B McAllister
*Assistant Examiner* — Daniel E Namay
(74) *Attorney, Agent, or Firm* — Oblon, Spivak, McClelland, Maier & Neustadt, L.L.P.

(57) ABSTRACT

A warming device of sheet form having (1) a heat generating sheet prepared by papermaking and containing an oxidizable metal, a moisture retaining agent, and a fibrous material and (2) an air permeable holder holding the heat generating sheet. The warming device has a thickness of 0.1 to 10 mm and a flexural strength of 0.01 to 0.3 N/cm. The sheet preferably has a thickness of 0.1 to 2.0 mm. The fibrous material preferably has a CSF of 600 ml or less.

21 Claims, 17 Drawing Sheets

U.S. PATENT DOCUMENTS

| | | | | |
|---|---|---|---|---|
| 341,584 | A * | 5/1886 | Leiter | 165/46 |
| 1,502,744 | A * | 7/1924 | Perrault | 44/252 |
| 1,525,168 | A * | 2/1925 | Davidson | 44/251 |
| 1,609,958 | A * | 12/1926 | Perrault | 126/263.02 |
| 1,819,807 | A * | 8/1931 | Baysinger | 44/253 |
| 2,040,407 | A * | 5/1936 | Reed | 44/253 |
| 2,110,677 | A * | 3/1938 | Racen | 132/220 |
| 2,112,674 | A * | 3/1938 | Lewit | 44/252 |
| 2,126,734 | A * | 8/1938 | Chancey | 132/220 |
| 2,261,221 | A * | 11/1941 | Bruner | 149/40 |
| 2,573,791 | A * | 11/1951 | Howells | 602/14 |
| 3,261,347 | A * | 7/1966 | Sherman | 126/263.02 |
| 3,301,250 | A * | 1/1967 | Glasser | 126/263.02 |
| 3,311,459 | A * | 3/1967 | Jones et al. | 149/15 |
| 3,390,046 | A * | 6/1968 | McDavid | 162/180 |
| 3,448,005 | A * | 6/1969 | Jone et al. | 162/164.3 |
| 3,545,230 | A * | 12/1970 | Morse | 62/530 |
| 3,702,799 | A * | 11/1972 | Lewis et al. | 162/168.2 |
| 4,057,047 | A * | 11/1977 | Gossett | 126/263.07 |
| 4,106,478 | A * | 8/1978 | Higashijima | 149/15 |
| 4,114,591 | A * | 9/1978 | Nakagawa | 126/263.02 |
| 4,203,418 | A * | 5/1980 | Donnelly | 126/263.05 |
| 4,205,957 | A * | 6/1980 | Fujiwara | 44/250 |
| 4,265,216 | A * | 5/1981 | Marshall et al. | 126/263.07 |
| 4,360,625 | A * | 11/1982 | Griffith | 524/414 |
| 4,516,564 | A * | 5/1985 | Koiso et al. | 126/263.02 |
| 4,522,190 | A * | 6/1985 | Kuhn et al. | 126/263.02 |
| 4,573,447 | A * | 3/1986 | Thrash et al. | 44/251 |
| 4,649,895 | A * | 3/1987 | Yasuki et al. | 126/263.05 |
| 4,692,259 | A * | 9/1987 | Roman | 252/70 |
| 4,804,823 | A * | 2/1989 | Okuda et al. | 219/553 |
| 4,856,651 | A * | 8/1989 | Francis, Jr. | 206/219 |
| 4,995,126 | A * | 2/1991 | Matsuda | 5/421 |
| 5,046,479 | A * | 9/1991 | Usui | 126/204 |
| 5,069,208 | A * | 12/1991 | Noppel et al. | 607/114 |
| 5,318,844 | A | 6/1994 | Brandon | |
| 5,366,492 | A * | 11/1994 | Ueki | 607/114 |
| 5,697,961 | A * | 12/1997 | Kiamil | 607/108 |
| 5,918,590 | A * | 7/1999 | Burkett et al. | 126/263.02 |
| 5,975,074 | A * | 11/1999 | Koiso et al. | 126/204 |
| 5,999,699 | A * | 12/1999 | Hyatt | 392/339 |
| 6,099,556 | A * | 8/2000 | Usui | 607/114 |
| 6,158,427 | A * | 12/2000 | McGuire et al. | 126/263.01 |
| 6,248,257 | B1 * | 6/2001 | Bell et al. | 252/70 |
| 6,974,470 | B2 | 12/2005 | Tsunakawa et al. | |
| 7,749,357 | B2 * | 7/2010 | Kumamoto et al. | 162/218 |
| 2001/0042546 | A1 | 11/2001 | Umeda et al. | |
| 2002/0020406 | A1 * | 2/2002 | Minami | 126/263.02 |
| 2005/0000827 | A1 | 1/2005 | Matsui et al. | |
| 2005/0028806 | A1 | 2/2005 | Kumamoto et al. | |
| 2006/0151136 | A1 | 7/2006 | Kumamoto et al. | |
| 2007/0020412 | A1 * | 1/2007 | Kumamoto et al. | 428/34.2 |
| 2008/0292879 | A1 * | 11/2008 | Kumamoto et al. | 428/339 |
| 2009/0101867 | A1 * | 4/2009 | Ishikawa et al. | 252/183.12 |
| 2010/0204417 | A1 * | 8/2010 | Hartman et al. | 525/527 |

FOREIGN PATENT DOCUMENTS

| | | | |
|---|---|---|---|
| EP | 1 121 912 | A2 | 8/2001 |
| EP | 1 121 912 | A3 | 8/2001 |
| EP | 1623689 | A1 * | 2/2006 |
| EP | 1655005 | A1 * | 5/2006 |
| JP | 55043346 | A * | 3/1980 |
| JP | 57031980 | A * | 2/1982 |
| JP | 60106874 | A * | 6/1985 |
| JP | 62-6815 | | 1/1987 |
| JP | 63-2028 | | 1/1988 |
| JP | 64-011543 | | 1/1989 |
| JP | 1-122930 | | 8/1989 |
| JP | 01-201253 | | 8/1989 |
| JP | 1-158762 | | 11/1989 |
| JP | 02274248 | A * | 11/1990 |
| JP | 4-33832 | | 6/1992 |
| JP | 4-37871 | | 9/1992 |
| JP | 5-46702 | | 12/1993 |
| JP | 7-83832 | | 9/1995 |
| JP | 08-112303 | | 5/1996 |
| JP | 08-173471 | | 7/1996 |
| JP | 8-275965 | | 10/1996 |
| JP | 2572621 | | 10/1996 |
| JP | 10-263002 | | 10/1998 |
| JP | 11-00353 | | 1/1999 |
| JP | 11-056895 | | 3/1999 |
| JP | 11-56896 | | 3/1999 |
| JP | 11071470 | A * | 3/1999 |
| JP | 11-128260 | | 5/1999 |
| JP | 2001-149401 | | 6/2001 |
| JP | 2001-198150 | | 7/2001 |
| JP | 2001-212168 | | 8/2001 |
| JP | 2002050725 | A * | 2/2002 |
| JP | 2002-155273 | | 5/2002 |
| JP | 2003-102761 | | 4/2003 |
| JP | 2003-129041 | | 5/2003 |
| JP | 2003-206479 | | 7/2003 |
| JP | 2005058248 | A * | 3/2005 |
| JP | 2005058744 | A * | 3/2005 |
| JP | 2005087719 | A * | 4/2005 |
| JP | 2005111180 | A * | 4/2005 |
| JP | 2005118319 | A * | 5/2005 |
| JP | 2005224316 | A * | 8/2005 |
| JP | 2005224317 | A * | 8/2005 |
| JP | 2005328852 | A * | 12/2005 |
| WO | WO 93/22499 | | 11/1993 |
| WO | WO 98/00077 | | 1/1998 |
| WO | WO 2004/041135 | A1 | 5/2004 |

OTHER PUBLICATIONS

File "JP2003102761_MT.pdf" Machine Translation; Apr. 22, 2010 (Machine Translation: JP-2003-102761, Translated Apr. 22, 2010).*
CRC Handbook of Chemistry and Physics; 91$^{st}$ Edition, 2010-2011; pp. 13-3 to 13-4.*
"2572621JPB2 TRANS 2011-09.pdf", Translation of JP-2572621, The McElroy Translation Co., Sep. 2011.*
U.S. Appl. No. 10/556,136, filed Nov. 9, 2005, Kumamoto, et al.
U.S. Appl. No. 10/534,047, filed Nov. 22, 2005, Kumamoto, et al.
U.S. Appl. No. 12/063,476, Feb. 11, 2008, Ishikawa, et al.
Communication pursuant to Article 94(3) EPC mailed Apr. 6, 2011 in European Patent Application No. 04 771 013.2 filed , Jul. 29, 2004.

* cited by examiner

WARMING TOOL IN A SHEET FORM

TECHNICAL FIELD

The present invention relates to a warming device of sheet form utilizing heat generation accompanying oxidation reaction of oxidizable metal with oxygen in air. More particularly, it relates to a warming device of sheet form that is thin, flexible, and agreeable to the touch.

The present invention also relates to a heat generating molded article of sheet form utilizing heat generation accompanying oxidation reaction of oxidizable metal with oxygen in air.

The present invention also relates to a heat generating sheet utilizing heat generation accompanying oxidation reaction of oxidizable metal with oxygen in air.

BACKGROUND ART

Known techniques pertinent to a heat generating sheet making use of heat generation accompanying oxidation of oxidizable metal powder with air oxygen include the heat generating element of sheet form described in Japanese Patent 2572612. The heat generating element of sheet form is made by papermaking using a composition comprising iron powder, activated carbon, an electrolyte, water, and a fibrous material and features conformability to a part of the body and the like.

Such a heat generating element of sheet form is used by, for example, putting the heat generating element in an air-permeable holder and applying or attaching the holder to a part of the body. A heat generating molded article of this type loses flexibility because iron powder cakes with progress of the exothermic reaction. It becomes gradually hard and feels uncomfortable in long time use.

The applicant of the present application previously made a proposal on a thin type heat generating molded article in JP-A-2003-102761. One of the characteristics of the heat generating molded article is that it is extremely thin and yet exhibits excellent heat generation characteristics as a heat generating element. It has been hoped that the proposed heat generating molded article would be free of the above described reduction in wearing comfort, feel during use and etc.

The warming seat pad disclosed in JP-A-U-1-158762 is also included in warming devices making use of heat generation accompanying oxidation reaction of oxidizable metal powder with air oxygen include. The warming seat pad consists of a flexible and air permeable foamed sheet as a surface side material, a flexible and heat-insulating back side material, a heat generating composition which heats up on contact with air and is interposed between the surface side material and the back side material, and a covering material having ventilation holes which covers the surface side material.

The warming seat pad is designed to supply sufficient air to the heat generating composition by disposing the heat-insulating sheet formed of open-cellular resin foam between the covering material and the heat generating composition. However, the heat insulating sheet absorbs a water vapor generated by the oxidation reaction, which gives rise to the problem that the heat generating composition is not uniformly oxidized, resulting in reduction of heat generation duration or variation in temperature of generated heat.

The foamed sheet disposed as a cushioning material between the covering material and the heat generating composition not only interferes with conduction of heat from the heat generating composition to the surface but also makes the pad bulky and inconvenience to carry. Because the heat generating composition is powder, it can be localized while in use to cause appreciable non-uniformity in temperature of heat generation. To use a powdered composition limits the product size and therefore limits the usability of the product. Furthermore, the powdered composition makes a rasping sound inherent to powder or causes a discomfort when a user sits thereon. Therefore, the warming seat pad is unsatisfactory as a commodity.

The above-mentioned thin type heat generating sheet proposed by the applicant is extremely thin and yet exhibits excellent heat generating characteristics as a heat generating element as stated and also enjoys high productivity. The sheet is additionally characterized by reduced fall-off of constituent components from the sheet compared with a conventional heat generating element made up of powder.

A heat generating sheet of this type is usually combined with an air permeable sheet and an air impermeable sheet and used as a heat generating molded article. Unity between these sheets and the heat generating sheet is therefore one of important factors that decide the heat generation characteristics, the hand or texture, the usability of the resulting heat generating molded article, and etc.

The heat generating molded article of sheet form proposed by the applicant is broadly usable in view of its characteristics. In some applications, the sheet is required to reach high temperatures immediately after the start of use. In some other applications, two or more of the sheets are used in a stacked form. In such cases, it is demanded to prevent the stacked sheets from sliding off each other.

JP-A-11-56895 proposes forming a pattern in a bag holding a heat generating element by embossing, which offers no solutions to the aforementioned problems.

While the heat generating molded article of sheet form proposed by the applicant has broad applications for its characteristics, it is still desirable to have the preferred heat generation characteristics without increasing the thickness.

DISCLOSURE OF THE INVENTION

The present invention relates to a warming device of sheet form that is thin, flexible, agreeable to the touch while in use, and suited to a variety of applications.

The present invention relates to a warming device of sheet form that sustains heat generation for a prolonged period of time and is suited to a variety of applications.

The present invention relates to a warming device of sheet form that is thin, flexible, excellent in heat generation characteristics, convenient to carry, and suited to a variety of applications.

The present invention relates to a heat generating molded article of sheet form which exhibits high unity between a heat generating sheet and an air permeable sheet or an air impermeable sheet, satisfactory heat generation characteristics, and an agreeable texture and hardly suffers fall-off of its constituents.

The present invention relates to a heat generating sheet which heats up immediately after the start of use and hardly slides when stacked one on top of another.

The present invention relates to a heat generating sheet thin and yet excellent in heat generation characteristics.

The present invention provides a warming device of sheet form (hereinafter simply referred to as a warming device) having a heat generating sheet and an air permeable holder holding the heat generating sheet. The heat generating sheet is prepared by papermaking and contains an oxidizable metal, a moisture retaining agent, and a fibrous material. The warming device has a thickness of 0.1 to 10 mm and a flexural strength of 0.01 to 0.3 N/cm.

The present invention also provides a warming device having a heat generating sheet and an air permeable holder holding the heat generating sheet. The heat generating sheet is prepared by papermaking and contains an oxidizable substance, a moisture retaining agent, and a fibrous material. The warming device further has a non-liquid-retentive heat insulating sheet disposed in the holder.

The present invention also provides a warming device having a heat generating sheet and an air permeable holder holding the heat generating sheet. The heat generating sheet is prepared by papermaking and contains an oxidizable substance, a moisture retaining agent, and a fibrous material. Part of the holder is formed of an air permeable sheet. The warming device has no heat insulating sheet between the air permeable sheet and the heat generating sheet. The warming device has a flexural strength of 0.01 to 1.0 N/cm.

The present invention also provides a heat generating molded article of sheet form (hereinafter simply referred to as a heat generating molded article) having a heat generating sheet and an air permeable sheet or an air impermeable sheet superposed on one or both sides of the heat generating sheet. The heat generating sheet contains an oxidizable metal, a moisture retaining agent, and a fibrous material and has a breaking length of 100 to 4000 m. The heat generating molded article has a large number of projections and depressions formed on a side thereof by embossing.

The present invention also provides a heat generating sheet having a molded article of sheet form (hereinafter simply referred to as a molded article) containing an oxidizable metal, a moisture retaining agent, and a fibrous material. The molded article has a breaking length of 100 to 4000 m and has a large number of projections and depressions formed on a side thereof by embossing.

The present invention also provides a heat generating sheet having a molded article. The molded article contains an oxidizable metal, a moisture retaining agent, and a fibrous material and has a large number of holes or cuts.

BRIEF DESCRIPTION OF DRAWINGS

FIG. 5($b$) is a cross-sectional view on arrow A-A in FIG. 5($a$).

FIG. 7($b$) is a cross-sectional view on arrow A-A in FIG. 7($a$).

FIG. 9($b$) is a cross-sectional view on arrow A-A in FIG. 9($a$).

BEST MODE FOR CARRYING OUT THE INVENTION

The present invention will be described based on its preferred embodiments with reference to the accompanying drawings.

Figure 1:
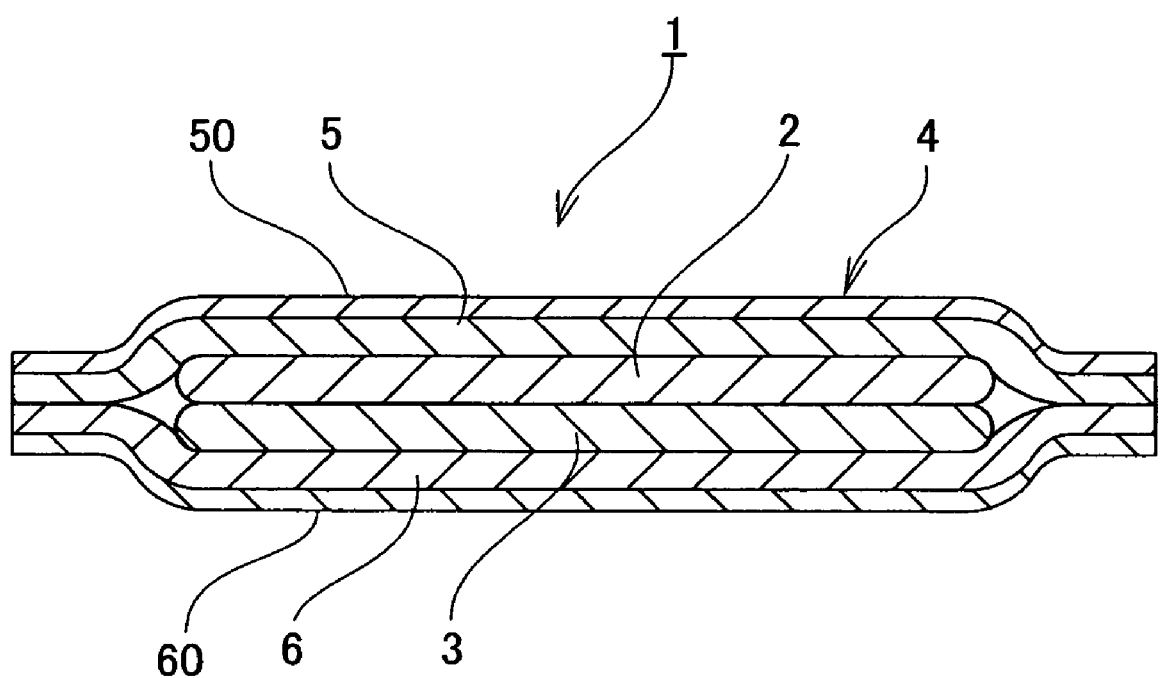
FIG. 1 is a schematic cross-sectional view of a first embodiment of the warming device according to the present invention.

FIG. 1 illustrates a first embodiment of the warming device according to the present invention, in which numeral 1 indicates a warming device.

As illustrated in FIG. 1, the warming device 1 has a heat generating sheet 2 prepared by papermaking process (hereinafter referred to as a molded sheet) and a non-liquid retentive, heat insulating sheet 3 both held in an air permeable holder 4. In what follows, a molded sheet free of an electrolyte (described later) is called a heat generating sheet precursor, and a molded sheet containing the electrolyte and water is called a heat generating sheet.

The holder 4 of the warming device 1 is formed of an air permeable sheet 5 and an air impermeable sheet 6. The heat insulating sheet 3 is interposed between the molded sheet 2 and the air impermeable sheet 6. There is no heat insulating sheet between the air permeable sheet 5 and the molded sheet 2.

The warming device 1 preferably has a flexural strength of 0.01 to 1.0 N/cm, more preferably 0.02 to 0.8 N/cm, even more preferably 0.03 to 0.5 N/cm. With the flexural strength falling within the recited range, the warming device 1 is highly flexible, easily foldable, and therefore convenient to carry (portable). In the present invention, the flexural strength is measured in three-point bending flexural test.

It is desirable for the warming device 1 to have a flexural strength of 0.05 to 3.0 N/cm, more preferably 0.02 to 1 N/cm, after heat generation comes to an end. Within that range, the warming device 1 keeps flexible from start to end of use and is easily disposed of after use.

The warming device 1 preferably has a thickness of 1 to 30 mm, more preferably 3 to 10 mm. The warming device of that thickness is thin and convenient to carry.

The warming device 1 preferably has a basis weight of 100 to 3000 g/m$^2$, more preferably 200 to 1500 g/m$^2$. The warming device 1 having a basis weight in that range is thin and flexible and gives no discomfort in applications where it is brought into contact with a human body.

The area, shape, and other geometrical features of the warming device 1 are decided as appropriate to the intended use.

The thickness of the heat generating sheet 2 is preferably 0.08 to 10 mm, more preferably 0.2 to 5 mm. With the thickness of the heat generating sheet 2 being in that range, the warming device is thin, flexible, and excellent in heat generating properties.

The heat generating sheet 2 contains an oxidizable substance, a moisture retaining agent, and a fibrous material.

The heat generating sheet precursor 2 preferably contains at least 50% by weight, more preferably 70% by weight or more, even more preferably 80% by weight or more, of components other than the fibrous material. When the content of the components other than the fibrous material is 50% by weight or more, the heat generating sheet heats up to or above the temperature feeling hot when touched with the finger and the like. The higher the content of the components other than the fibrous material, the more preferred. Nevertheless, the upper limit is about 98% by weight for assuring strength necessary to maintain fabricability of the heat generating sheet precursor 2.

The oxidizable substance is not particularly limited, and any oxidizable materials commonly employed in heat generating molded articles of this type can be made use of. The oxidizable substance preferably has a particulate or fibrous form from the standpoint of handling, molding properties, and etc.

Particulate oxidizable substances include iron powder, aluminum powder, zinc powder, manganese powder, magnesium powder, calcium powder and etc. Iron powder is preferred of them because of its handling properties, safety, and production cost. The particulate oxidizable substance preferably has a particle size of 0.1 to 300 μm for fixability onto the fibrous material (described infra) and ease of reaction control. The term "particle size" as used herein means a maximum length of powder particles or an average particle size measured by a dynamic light scattering method, a laser diffraction method, and the like. It is more preferred to use powder containing particles having a particle size of 0.1 to 150 μm in a proportion of 50% by weight or more.

Fibrous oxidizable substances include steel fiber, aluminum fiber, magnesium fiber and etc. Steel fiber, aluminum fiber or the like is preferred for handling properties, safety, and production cost. The fibrous oxidizable substance preferably has a fiber length of 0.1 to 50 mm and a thickness of 1 to 1000 μm from the viewpoint of molding properties and the mechanical strength, surface smoothness and heat generating performance of the resulting sheet.

The proportion of the oxidizable substance in the heat generating sheet precursor 2 is preferably 10% to 95% by weight, more preferably 30% to 80% by weight. With 10% by weight or more of the oxidizable substance, the resulting heat generating sheet 2 sufficiently heats up to or above the temperature feeling hot to the touch of fingers, and reduce the proportions of the fibrous material and a binding component (e.g., a flocculant), which constitute the heat generating sheet as hereinafter described, being so controlled, the heat generating sheet 2 is comfortable to use in terms of hardness. With the oxidizable substance content being 95% by weight or less, the following advantages are offered. The reaction takes place sufficiently in the inside of the heat generating sheet 2 to sufficiently raise the temperature. Hardening of the oxidizable substance due to setting expansion on oxidation is relatively suppressed. The duration of heat generation is sufficient a water vapor supply by the moisture retaining agent is secured. The oxidizable substance hardly falls off the sheet. Certain proportions of the fibrous material and binding component hereinafter described, which make up the heat generating sheet 2, are secured to assure mechanical strength characteristics such as flexural strength and tensile strength. The oxidizable substance content in the heat generating sheet 2 can be determined by determination of ash in accordance with JIS P8128 or with a thermogravimetric analyzer. Vibrating sample magnetization measurement is useful in the case of iron, of which the magnetization on applying an external magnetic field is made use of.

The moisture retaining agent includes any moisture retaining agents commonly employed in heat generating molded articles with no particular limitation. The moisture retaining agent not only serves for a water vapor retention but functions as an agent for holding and supplying oxygen to the oxidizable substance. Useful moisture retaining agents include activated carbon (palm shell charcoal, wood charcoal, bituminous coal, peat, and lignite), carbon black, acetylene black, graphite, zeolite, pearlite, vermiculite, silica, cancrinite, fluorite and the like. Preferred of them is activated carbon for its a water vapor retaining ability, oxygen supplying ability, and catalytic ability. It is preferred to use a particulate moisture retaining agent having a particle size of 0.1 to 500 μm, particularly the one containing particles with a particle size of 0.1 to 200 μm in a proportion of 50% by weight or more, in view of the capability of providing an effective contact with the oxidizable substance. Moisture retaining agents of other forms are also usable. For example, those of fibrous form such as activated carbon fiber can be used.

The moisture retaining agent is preferably present in the heat generating sheet precursor 2 in an amount of 0.5% to 60% by weight, more preferably 1% to 50% by weight. With a moisture retaining agent content of 0.5% by weight or more, the heat generating sheet 2 holds a requisite water content for the oxidizable substance to sustain oxidation reaction for maintaining the temperature at or above the body temperature. Furthermore, the heat generating sheet 2 has sufficient air permeability for oxygen supply to achieve high heat generation efficiency. With the moisture retaining agent content being 60% by weight or less, the following advantages are offered. The heat generating sheet 2 has a controlled heat capacity for the amount of heat generated to show a sufficient temperature rise. The moisture retaining agent hardly falls off. Sufficient amounts of the fibrous material and binding component hereinafter described, which build up the heat generating sheet 2, are secured to assure sufficient mechanical strength such as flexural strength and tensile strength.

The fibrous material includes natural fiber, and synthetic fibers. The natural fibers include plant fibers, such as cotton, kapok fiber, wood pulp, non-wood pulp, peanut protein fiber, corn protein fiber, soybean protein fiber, mannan fiber, rubber fiber, hemp, Manila fiber, sisal fiber, New Zealand flax, Luo Buma, coconut, rush, and straw; animal fibers, such as wool, goat hair, mohair, cashmere, alpaca, angora, camel, vicuna, silk, down, small feather, alginate fiber, chitin fiber, and casein fiber; and mineral fibers, such as asbestos. The synthetic fibers include semi-synthetic ones, such as cellulose diacetate, cellulose triacetate, oxidized cellulose acetate, promix, chlorinated rubber, rubber hydrochloride, metal fibers, carbon fiber, glass fiber, and etc. Also useful are single-component fibers made of polyolefin (e.g., high-density polyethylene, medium-density polyethylene, low-density polyethylene or polypropylene), polyester, polyvinylidene chloride, starch, polyvinyl alcohol or polyvinyl acetate, a copolymer thereof, or a modified product thereof; and core/sheath conjugate fibers having the above-recited resin component as a sheath. Of these fibers, polyolefin fibers and modified polyester fibers are preferably used for high bonding strength between individual fibers, high ability to form a three-dimensional network structure on fusion bonding of individual fibers, and a lower melting point than the ignition point of pulp fiber. Synthetic fibers of polymers having branches, such as branched polyolefin fibers, are also preferred for their fixing capabilities for the oxidizable substance and the moisture retaining agent. The above-recited fibrous materials can be used either individually or as a combination of two or more thereof. Recycled products of these fibrous materials are also employable. Among these fibrous materials particularly preferred are wood pulp and cotton in view of their fixing capabilities for the oxidizable substance and the moisture retaining agent, flexibility of the resulting molded sheet, oxygen permeability of the resulting sheet owing to the presence of interstitial voids, the cost of production and etc.

It is preferred for the fibrous material to have a CSF (Canadian Standard Freeness) of 600 ml or less, more preferably 450 ml or less. Fibrous materials having a CSF of 600 ml or less have sufficient fixing capabilities for such components as the oxidizable metal and the moisture retaining agent to hold prescribed amounts of the components thereby to assure excellent heat generating performance. Furthermore, a sheet with a uniform thickness and good molding conditions can be obtained. The sufficient fixing capabilities of the fibrous material for the other components will prevent fall-off of the components, and sufficient entanglement and hydrogen bonding between the fibrous material and the components will provide sufficient bonding strength. As a result, the sheet has sufficient mechanical strength, such as flexural strength and tensile strength, and excellent fabricability.

It is desirable for the fibrous material to have as low a CSF as possible. In carrying out papermaking using a slurry containing ordinary pulp fiber as a sole fibrous material and having high contents of components other than the fibrous material, the CSF is preferably 100 ml or higher to secure satisfactory drainage and dewatering to provide a heat generating sheet with a uniform thickness. Moreover, molding defects such as burst of blisters on drying are hardly experienced. Since the proportion of the components other than the fibrous material is relatively high, the slurry shows satisfactory drainage to provide a heat generating sheet with a uniform thickness. A lower CSF indicates a higher fibril content, and a higher fibril content secures better fixation of the components other than the fibrous material on the fibrous material, which results in high sheet strength. The CSF of a fibrous material can be controlled by, for example, the degree of beating. The CSF may also be adjusted by blending fibers different in CSF.

The fibrous material preferably has a negative zeta potential. "Zeta potential" is an apparent potential at the shear plane separating a charged particle and a solution, which can be determined by streaming potential measurement electrophoresis measurement or the like. A fibrous material having a negative zeta potential has satisfactory ability to fix the above-mentioned components including the oxidizable metal and the moisture retaining agent thereby to secure predetermined amounts of the components, assuring sufficient heat generating performance. Running of large quantities of the components into drain water can be prevented, i.e., loss of the components is minimized, which is favorable for the productivity and environmental protection.

The fibrous material preferably has an average length of 0.1 to 50 mm, more preferably 0.2 to 20 mm. Too short fibers fail to secure sufficient mechanical strength, such as flexural strength and tensile strength, of the resulting heat generating sheet 2. Too short fibers make too dense a fibrous layer that will impair the air permeability of the heat generating sheet 2. As a result, the heat generating sheet 2 can have poor heat generating performance due to inadequate oxygen supply. Too long fibers are difficult to disperse uniformly in the heat generating sheet 2, leading to a failure to obtain uniform mechanical strength or uniform sheet thickness. In addition, the increased fiber distance results in reduced capability of holding the other components such as the oxidizable substance, the moisture retaining agent and etc, easily causing these components to fall off.

The fibrous material content in the heat generating sheet precursor 2 is preferably 2% to 50% by weight, more preferably 5% to 40% by weight. Where the content is less than 2% by weight, the effect for preventing the oxidizable substance, the moisture retaining agent, etc. from falling off is reduced, and the heat generating sheet 2 tends to be very brittle. If the fibrous material content is more than 50% by weight, the heat generating sheet 2 will have an increased heat capacity for the amount of heat generated, and a reduced rise in temperature results. Furthermore, the proportion of the other components is so low that the resulting heat generating sheet 2 can fail to exhibit desired heat generating performance.

The ratios of the components are obtained by, for example, measuring the fibrous material content and the oxidizable substance content with a thermogravimetric analyzer. Subtracting these contents from the total weight gives the content of the moisture-retaining agent.

The thickness of the heat generating sheet precursor 2 is preferably 0.08 to 1.2 mm, more preferably 0.1 to 0.6 mm. A thickness of 0.08 mm or more assures sufficient heat generating performance, mechanical strength, fixation of the oxidizable substance, the moisture retaining agent, etc., and uniformity (stability) in thickness and composition. A thickness of 0.08 mm or more is also preferred in productivity and fabricability because defects, such as break of the sheet due to pinhole development, hardly occur. A sheet with a thickness of 1.2 mm or less has folding strength, flexibility and, in particular, good conformability to fit a bending part of a body, such as an elbow, a knee, and the face. In addition, the time for papermaking and drying is relatively short to provide good operationality. The thickness is also preferred in fabricability. The thickness of the heat generating sheet precursor is obtained by taking measurements at five or more different points in accordance with JIS P8118 and averaging the results.

The basis weight of the heat generating sheet precursor 2 is preferably 10 to 1000 g/m², more preferably 50 to 600 g/m². Even in using, for example, an oxidizable substance having a high specific gravity, a sheet having a basis weight of 10 g/m² or more can be formed stably. A sheet weighing 1000 g/m² or less is satisfactory in usability, productivity, operationality, and etc. The basis weight of the heat generating sheet precursor 2 is calculated by dividing the weight of the sheet of an area of at least 100 cm³ by the area.

It is preferred for the heat generating sheet precursor 2 to have a density of 0.6 to 1.5 g/cm³, more preferably 0.7 to 1.0 g/cm³. In the heat generating sheet precursor having a density of 0.6 g/cm³ or higher, the oxidizable substance and other components are in good entanglement with each other, which is favorable for strength. The heat generating sheet precursor having a density of 1.5 g/cm³ or lower has sufficient air permeability to exhibit its heat generation characteristics to the full. The density of the heat generating sheet precursor 2 is calculated by dividing the basis weight by the thickness.

It is preferred for the heat generating sheet precursor 2 to have a breaking length of 100 to 4000 m, more preferably 200 to 3000 m. With a breaking length of 100 m or longer, the sheet is formed in a stable manner during the production operation; the resulting sheet is fabricated in a stable manner; and the final product has sufficient strength for good usability. A heat generating sheet precursor 2 with a breaking length of 4000 m or less contains moderately controlled amounts of the fibrous material and the binding component as the sheet-forming components and is therefore flexible and excellent in heat generating performance. The breaking length is measured as follows. A 15 mm wide and 150 mm long test piece cut out of a heat generating sheet precursor 2 is subjected to a tensile test at an initial gauge length of 100 mm and a pulling speed of 20 mm/min in accordance with JIS P8113. A breaking length is calculated according to equation:

$$\text{Breaking length(m)} = (1/9.8) \times ((\text{tensile strength(N/m)}) \times 10^6/(\text{basis weight of test piece(g/m}^2)))$$

The heat generating sheet 2 contains an electrolyte.

The electrolyte to be added is not particularly limited, and any kind commonly used in this type of heat generating molded articles can be used. Examples of useful electrolytes include sulfates, carbonates, chlorides, and hydroxides of alkali metals, alkaline earth metals or heavy metals etc. Preferred of them are chlorides, such as sodium chloride, potassium chloride, calcium chloride, magnesium chloride, and iron (I) or (II) chloride, in view of their electrical conductivity, chemical stability, and production cost. These electrolytes can be used either individually or as a combination of two or more thereof.

The electrolyte is preferably added in an amount of 0.5% to 30% by weight, more preferably 1% to 25% by weight, based on the water content of the resulting heat generating sheet 2. At the electrolyte content of 0.5% by weight or more, the oxidation reaction proceeds sufficiently in the resulting heat generating sheet 2, and a sufficient temperature rise is achieved. At the electrolyte content of 30% by weight or less, satisfactory air permeability is retained in the heat generating sheet 2, and a sufficient amount of water is supplied to the oxidizable substance, etc. to assure high heat generating performance. The electrolyte of that amount can uniformly be distributed throughout the heat generating sheet 2.

A flocculant may be incorporated into the heat generating sheet 2 as described infra.

If desired, the heat generating sheet 2 may contain additives commonly used in papermaking, such as sizes, colorants, strengthening agents, yield improvers, loading materials, thickeners, pH control agents, bulking agents, and etc., with no particular limitation. The amounts of the additives to be added can be decided appropriately according to the kinds.

The thickness of the heat generating sheet 2 is 0.08 to 2.0 mm, preferably 0.15 to 1.8 mm. A heat generating sheet 2 having a thickness of 0.08 mm or more exhibits sufficient heat generating performance and mechanical strength. A sheet with a thickness of 2 mm or less has sufficient flexibility and provides comfort of use. The thickness of the heat generating sheet is obtained by taking measurements at five or more different points in accordance with JIS P8118 and averaging the results.

The heat generating sheet 2 preferably has a basis weight of 10 to 2000 g/m², more preferably 50 to 1500 g/m². The heat generating sheet 2 having a basis weight of 10 g/m² or more is produced in a stable manner. The heat generating sheet 2 having a basis weight of 2000 g/m² or less is favorable for comfort of use.

It is preferred for the heat generating sheet 2 to have a density of 0.6 to 3.0 g/cm³, more preferably 0.7 to 2.0 g/cm³. In the heat generating sheet having a density of 0.6 g/cm³ or higher, the oxidizable substance and other components are in good entanglement with each other, which assures sufficient strength and prevents constituent components from falling off to secure productivity and fabricability. The heat generating sheet having a density of 3.0 g/cm³ or lower is soft enough to provide conformability, pleasant feel to the touch, and usability and has sufficient air permeability to exhibit excellent heat and steam generating performance. The density of the heat generating sheet 2 is calculated by dividing the basis weight by the thickness.

The temperature reached by the heat generating sheet 2 on heat generation is preferably 30° to 100° C., more preferably 35° to 90° C. This temperature is measured as follows. A 50 mm side square test piece cut out of a heat generating sheet is sealed in between a water vapor permeable sheet and a water vapor impermeable sheet by bonding the periphery of the two sheets to make a closed bag. The a water vapor permeable sheet has a water vapor permeability rate of 5000 g/(m²·24 hr) as measured according to JIS Z208. The bag containing the test piece is placed with the a water vapor permeable sheet side up in a 4.2-liter closed chamber having a relative humidity of 1% or lower while feeding 5.0 l/min of dry air into the chamber to induce heat generation. The temperature of the lower side of the heat generating sheet measured with a thermocouple is the temperature reached by the sheet on heat generation. The temperature reachable by the heat generating sheet 2 can freely be designed by the formulation of the components according to the purpose, that is, whether a steep temperature rise is needed or a long duration of heat generation at a relatively low temperature is desired, and the like.

It is desirable for the heat generating sheet 2 to generate 1 to 100 mg/(cm²·10 min), more preferably 1.0 to 50 mg/(cm²·10 min), of water vapor per unit area for 10 minutes. The amount of water vapor generated is measured as follows.

A tester having a 4.2-liter closed chamber adjusted to 1% RH or less in which 5.0 l/min of dry air is fed is prepared. A test sheet is placed in the chamber and let to heat up so that water vapor generated may spread in the chamber. The humidity of the air discharged from the chamber is measured with a hygrometer, from which the amount of water vapor generated per unit time after the start of heat generation is calculated according to equation (1) shown below. The cumulative amount of water vapor generated for a period of 10 minutes is obtained and converted to a value per unit area. In the following equations, e stands for water vapor pressure (Pa); es, a saturated water vapor pressure (Pa; according to JIS Z8806); T, temperature (° C.; dry-bulb temperature); and s, sampling cycle (sec).

$$\text{Relative humidity } U(\% RH) = (e/es) \times 100$$

$$\text{Absolute humidity } D(g/m^3) = (0.794 \times 10^{-2} \times e)/(1+0.00366T) = (0.794 \times 10^{-2} \times U \times es)/[100 \times (1+0.00366T)]$$

$$\text{Unit air volume } P(\text{liter}) = (2.1 \times s)/60$$

$$\text{Amount of water vapor per unit time } A(g) = (P \times D)/1000 \tag{1}$$

Similarly to the time required for reaching the maximum temperature of heat generation, the amount of water vapor produced can be freely designed by the formulation of the components according to the purpose, that is, whether a steep temperature rise is desired or a long duration of heat generation at a relatively low temperature is desired, and the like.

The water content of the heat generating sheet 2 is preferably 10% to 80% (by weight, hereinafter the same), more preferably 20% to 60%. With a water content of 10% or more, a water vapor necessary for continuing oxidation reaction is secured to allow the oxidation reaction to proceed sufficiently. Furthermore, a water vapor can be distributed uniformly throughout the heat generating sheet 2 to assure uniform heat generation. With a water content of 80% or less, the heat generating sheet 2 has a controlled heat capacity for the amount of heat generated to achieve a sufficient rise in temperature; sufficient air permeability is secured to assure high heat generating performance; and the sheet 2 is excellent in shape retention and mechanical strength.

The heat insulating sheet 3 does not have a liquid retentive function. The warming device 1 does not retain, in the side of the heat insulating sheet 3, the a water vapor generated from the heat generating sheet 2. Therefore, the oxidation reaction proceeds smoothly, and a high temperature of heat generation is sustained for a prolonged period of time.

The heat insulating sheet 3 includes (1) foamed polyethylene, foamed polyurethane, foamed polystyrene and foamed melamine each of which is of closed cell type, (2) bubble film, (3) a bulky pulp sheet, corrugated paper, woven fabric or nonwoven fabric each of which is laminated with a water impermeable film, (4) composites of these materials and the like. Above all, a heat insulating sheet made of foamed polyethylene is preferably used for its light weight, flexibility, and cushioning properties. To laminate or deposit aluminum foil on a heat insulating sheet is preferred; for the warming effect is enhanced by radiant heat.

The thickness of the heat insulating sheet 3 is decided arbitrarily according to the end use or the environment of use. Taking into consideration both usability (e.g., bulkiness, portability, and disposability), heat generating performance and the like, the thickness is preferably 0.2 to 30 mm, more preferably 0.5 to 10 mm. The density of the heat insulating sheet 3 is preferably 0.005 to 0.9 g/cm$^3$, more preferably 0.01 to 0.6 g/cm$^3$, taking into consideration reduction in heat insulating effect due to cell collapse under a load, flexibility, and the like.

The holder 4 is not particularly limited as long as it has air permeability and prevents fall-off of the components constituting the heat generating sheet 2. To have the heat generating sheet 2 exhibit sufficient heat generation characteristics, the holder 4 preferably has a water vapor permeability of 100 to 10000 g/(m$^2$·24 hr), more preferably 200 to 8000 g/(m$^2$·24 hr).

In the present embodiment, the holder 4 of the warming device 1 is made by joining the air permeable sheet 5 and the air impermeable sheet 6 along their periphery with the heat generating sheet 2 enclosed therebetween. The method of joining the air permeable sheet 5 and the air impermeable sheet 6 is chosen as appropriate for the materials of the sheets. Useful methods include heat sealing, ultrasonic sealing, bonding with an adhesive, sewing, and etc.

The air permeable sheet 5 is not particularly limited as long as it has air permeability. It is preferred for the air permeable sheet 5 to have a water vapor permeability of 100 to 10000 g/(m$^2$·24 hr), more preferably 200 to 8000 g/(m$^2$·24 hr). With the water vapor permeability being in that range, the warming device rapidly co-generates heat and steam immediately after it is taken out of the package so that a user may feel warmed and moisturized without wait. The air permeable sheet 5 may have air permeability all over the entire area or partly.

The air permeable sheet 5 preferably has a basis weight of 10 to 200 g/m$^2$, more preferably 20 to 100 g/m$^2$. The air permeable sheet 5 whose basis weight is in that range is thin and flexible, feels very pleasant, does not impair the softness of the warming device 1, and allows the heat generating sheet 2 to generate heat and steam rapidly.

The air permeable sheet 5 includes a mechanically perforated sheet of a resin, such as a polyolefin (e.g., polyethylene (PE) or polypropylene (PP)), polyester, polyamide, polyurethane, polystyrene or an ethylene-vinyl acetate copolymer, etc.; a microporous sheet obtained by stretching a sheet of the above-recited resin containing an inorganic filler to make pores by phase separation; a microporous sheet obtained by making use of interfacial separation of the crystal structure of the above resin; and an open-cell sheet formed by foaming. Woven or nonwoven fabrics or synthetic paper made of synthetic pulp (e.g., polyolefin), wood pulp, non-wood pulp, semi-synthetic fibers (e.g., rayon and cellulose acetate), vinylon fiber, polyester fiber, etc., and paper are also useful. A plurality of the air-permeable sheets 5 can be used as stacked.

The warming device 1 has a surfacing member 50 on the surface of the air permeable sheet 5. The surfacing member 50 is not particularly limited in material production process and etc., unless the air permeability of the air permeable sheet 5 is affected. The surfacing member 50 includes nonwoven fabric made of synthetic fibers, natural fibers or composite fibers thereof. Production processes include spun bonding, needle punching, hydroentanglement, melt blowing, flash spinning, air laying, through-air processing, papermaking and the like. Through-air processing or air laying is preferred in view of softness and flexibility of the resulting nonwoven fabric. Hydroentanglement is preferred for wide applicability to various kinds of fibers. The surfacing member 50 can contain various perfumes. Taking perfume retentivity into consideration, hydroentanglement is preferred for applicability to fibers having high water and oil retentivity, exemplified by rayon, cotton and etc.

While the basis weight of the surfacing member 50 is not particularly limited, it is preferably 5.0 to 200 g/m$^2$, more preferably 10 to 100 g/m$^2$, taking into consideration efficient heat conduction from the heat generating element, hand or texture, such as touch to the skin, and strength against rubbing or pressing during use.

The air impermeable sheet 6 can be of any material as long as it is impermeable to air. The air impermeable sheet 6 preferably has a water vapor permeability of 10 g/(m$^2$·24 hr) or less, more preferably 1.0 g/(m$^2$·24 hr) or less. As long as the a water vapor permeability of the air impermeable sheet 6 falls within the above range, it is believed to be unlikely that a liquid substance enters from the air impermeable sheet side to adversely affect the quality of the heat generating sheet in applications under high temperature and high humidity conditions or in contact with liquid. Furthermore, the direction of release of water vapor co-generated with heat generation is partly controlled. Thus, oxygen is supplied from the air permeable sheet side, and steam generated is allowed to be released only from the air permeable sheet side while steam release from the air impermeable sheet side is suppressed.

The air impermeable sheet 6 preferably has a basis weight of 10 to 200 g/m$^2$, more preferably 20 to 100 g/m$^2$. Within this range of basis weight, the air impermeable sheet 6 retains the thinness and flexibility of the warming device 1 and yet exhibits improved capability of hiding the heat generating sheet from sight.

Materials of the air impermeable sheet 6 include synthetic resins such as polyolefin (e.g., PE or PP), polyester, polyamide, polyurethane, polystyrene, nylon, polyvinylidene chloride, and an ethylene-vinyl acetate copolymer, etc. Where the heat generating element should be hidden from sight, a sheet made of the above-recited resin having an inorganic filler (e.g., titanium oxide) incorporated therein is useful. More than two air impermeable sheets 6 may be used as stacked.

The warming device 1 has a surfacing member 60 on the surface of the air impermeable sheet 6. The surfacing member 60 is not particularly limited in material, production process and etc. The surfacing member 60 includes nonwoven fabric made of synthetic fibers, natural fibers or composite fibers thereof. Production processes include spun bonding, needle punching, hydroentanglement, melt blowing, flash spinning, air laying, through-air processing, papermaking and etc.

While the basis weight of the surfacing member 60 is not particularly limited, it is preferably 5.0 to 200 g/m$^2$, more preferably 10 to 100 g/m$^2$, taking into consideration improvement on heat insulation effect and strength against rubbing or pressing.

The warming device 1 is supplied as individually packaged in an oxygen impermeable packaging material.

The warming device 1 is produced by, for example, interposing a heat generating sheet 2, which is prepared as described below, and the heat insulating sheet 3 at a prescribed position between the sheets making up the holder 4, bonding the periphery of the air permeable sheet 5, the air impermeable sheet 6, the surfacing members 50 and 60 to enclose the heat generating sheet 2, and cutting the laminate into a prescribed shape.

Production of the heat generating sheet 2 starts with preparation of a raw material composition (slurry) containing the oxidizable substance, the moisture-retaining agent, the fibrous material, and water.

A flocculant is preferably added to the raw material composition.

The flocculant includes inorganic ones, such as metal salts, e.g., aluminium sulfate, polyaluminum chloride, iron ferric chloride, iron polyferric sulfate, and iron ferrous sulfate, etc; polymeric ones, such as polyacrylamides, sodium polyacrylates, Mannich base-modified polyacrylamide, aminoalkylester poly(meth)acrylates, sodium carboxymethyl celluloses, chitosans, starches, and polyamide-epichlorohydrins, etc; organic flocculants, such as dimethyldiallylammonium chloride type or ethyleneimine type alkylene dichloride-polyalkylenepolyamine condensates, and dicyandiamide-formalin condensates, etc; clay minerals, such as montmorillonite and bentonite; silicon dioxide and its hydrates, such as colloidal silica, etc; and hydrous magnesium silicate, such as talc, etc; Preferred of these flocculants are combinations of an anionic agent and a cationic agent from the standpoint of sheet surface properties, formation, molding properties, properties of fixing the oxidizable substance, the moisture retaining agent, etc., and sheet strength. Suitable combinations include a combination of colloidal silica or bentonite, etc; (anionic) and starch or polyacrylamide, etc; (cationic) and a combination of sodium carboxymethyl cellulose (anionic) and a polyamide-epichlorohydrin resin (cationic). In addition to these combinations, the above-recited flocculants can be used either individually or in combination of two or more thereof.

The flocculant is preferably added in an amount of 0.01% to 5% by weight, more preferably 0.05% to 1% by weight, based on the total solids content of the raw material composition. With the amount of the flocculant being 0.01% by weight or more, an excellent flocculating effect is produced so that the components such as the oxidizable substance and the moisture retaining agent are prevented from running into white water in the step of papermaking. Furthermore, the raw material composition is uniform to give a molded sheet with a uniform thickness and a uniform composition. With the amount of the flocculant being 5% by weight or less, sticking of the flocculant to drying rolls during the step of drying hardly occurs, which assures high productivity. The potential balance of the raw material composition is maintained to minimize running of the above components into white water during papermaking. Furthermore, oxidation is prevented from proceeding in the molded sheet thereby securing storage stability of the sheet in heat generation characteristics, strength, and the like.

The concentration of the raw material composition preferably ranges 0.05% to 10% by weight, more preferably 0.1% to 2% by weight. In concentrations of 0.05% by weight or higher, a large quantity of water is not needed, and much time is not required for papermaking. Furthermore, a molded sheet with a uniform thickness can be formed. In concentrations of 10% by weight or lower, the raw material composition maintains a satisfactory disperse state to provide a sheet with excellent surface properties and a uniform thickness.

The raw material composition is formed into a molded sheet by papermaking techniques.

Papermaking techniques for making the molded sheet include continuous papermaking by use of a cylinder paper machine, a foundrinier paper machine, a short-wire paper machine, a twin-wire paper machine, etc.; and batch papermaking such as manual papermaking. A multilayer molded sheet may be obtained by using the above-described raw material composition and a composition having a different formulation. A multilayer molded sheet may also be obtained by laminating molded sheets separately prepared from the raw material composition or laminating a molded sheet prepared from the raw material composition and a molded sheet prepared from a composition having a different formulation.

The molded sheet is dewatered preferably to a water content of 70% or less (by weight, hereinafter the same), more preferably 60% or less, for assuring shape retention and mechanical strength after papermaking. Dewatering of the molded sheet after papermaking is carried out by, for example, suction, application of pressurized air or pressing with a pressure roll or a pressure plate.

The molded sheet, which contains the oxidizable substance capable of exothermic reaction in an ordinary atmosphere, is then subjected to positive drying to remove the water content. Removal of the water content provides a molded sheet that is inhibited from inducing oxidation of the oxidizable substance during the subsequent steps and has excellent long-term storage stability. Drying of the sheet is preferably carried out after the papermaking and before addition of an electrolytic solution containing the aforementioned electrolyte so that the oxidizable substance may be firmly fixed and held by the fibrous material and be prevented from falling off and that improvement in mechanical strength by addition of a heat fusible component or a thermal crosslinking component may be expected.

Drying of the molded sheet is preferably effected by heating. The heating temperature is preferably 60° to 300° C., more preferably 80° to 250° C. If the heat drying temperature is too low, a prolonged drying time is needed, and meanwhile, oxidation of the oxidizable substance would be accelerated with evaporation of water, which can result in reduction of the heat generating performance of the heat generating sheet. Accelerated oxidation of the oxidizable substance in the upper and lower skin layers of the heat generating sheet can cause color change to pale brown. Too high a heat drying temperature invites deterioration of performance of the moisture retaining agent, etc., resulting in reduction of the heat generating performance of the heat generating sheet. Additionally, abrupt water vaporization inside the molded sheet can destroy the sheet structure.

The water content of the molded sheet after drying (i.e., the heat generating sheet precursor) is preferably 20% or less, more preferably 10% or less. Where the water content is 20% or less, the resulting sheet has excellent long-term storage stability. For example, when the sheet is stored in a roll form or the like, migration of water in the radial direction of the roll hardly occurs so that the sheet is able to supply products uniform in heat generating performance and mechanical strength.

The method of drying the molded sheet is selected appropriately depending on the sheet thickness, the treatment given to the sheet before drying, the water contents before and after the drying, and the like. Useful drying methods include contact with a heating structure (heat generating element), application of heated air or steam (superheated steam), vacuum drying, microwave heating, and electric current heating. The drying may be carried out simultaneously with the above-described dewatering.

Shaping of the molded sheet (i.e., dewatering and drying) is preferably conducted in an inert gas atmosphere. Nevertheless, because the molded sheet is free from an electrolyte acting as an oxidation promoter, the shaping may be performed in an ordinary air atmosphere if desired, which enables simplification of equipment. Where necessary, the dried sheet is fabricated by craping, slitting, trimming or any other processings for shaping or forming. Thin and yet tear-proof, the resulting molded sheet can be taken up in a roll if needed. The molded sheet or a plurality of the molded sheets, either alone or as laminated with other film or sheet (e.g., paper, woven fabric, nonwoven fabric or plastic film), may be pressed, embossed or needle-punched to be united into a unitary sheet, given uneven patterns or perforated. In order to facilitate heat sealing for lamination or other processing, a thermoplastic resin component or a hot-water-soluble component may be incorporated into the raw material composition.

The electrolyte is then incorporated into the molded sheet (heat generating sheet precursor). The step of incorporating the electrolyte is preferably carried out in an inert gas atmosphere such as nitrogen or argon. Where the electrolyte is incorporated by impregnation with an electrolytic solution, the impregnating step can be conducted in an ordinary air atmosphere because oxidation that may proceed immediately after the impregnation is mild.

The method of incorporating the electrolyte into the molded sheet is selected appropriately according to the treatment given to the sheet after papermaking, the water content and the form of the sheet, and the like. For example, the electrolyte can be incorporated by impregnating the molded sheet with an electrolytic solution having a prescribed electrolyte concentration, adding a powdered electrolyte having a prescribed particle size directly to the molded sheet, or injecting an electrolytic solution having a prescribed concentration into a part of the molded sheet using a syringe, etc. and making the solution spread throughout the molded sheet by capillarity of the fibrous material. Impregnation is preferred for achieving uniform distribution of the electrolyte and simultaneously controlling the water content of the resulting sheet.

When the electrolyte is incorporated into the molded sheet by impregnation with a solution of the electrolyte, the manner of impregnation is chosen as appropriate to the form (e.g., thickness) and the water content of the molded sheet. Impregnation methods include spraying, coating with a brush, etc., soaking in the electrolytic solution, gravure coating, reverse coating, doctor blade coating and the like. Spraying is preferred for uniform distribution, ease of operation, and relatively low cost of equipment. Where the product has a complicated shape or layer structure, injection of an electrolyte solution at a prescribed concentration using a syringe, etc. is preferred for productivity, process flexibility (the final finishing process can be done in a separate step), and simplicity of equipment. It is possible to conduct injection after the molded sheet is enclosed in the holder.

Where necessary, the water content of the molded sheet containing the electrolyte is adjusted to provide a stabilized heat generating sheet. If desired, the heat generating sheet thus prepared can be fabricated to yield a product of desired size by trimming, stacking one on top of another or etc.

Since the warming device 1 thus produced has the air permeable heat insulating sheet 3 disposed between the heat generating sheet 2 and the air impermeable sheet 6, heat dissipation toward the side of the air impermeable sheet 6 is suppressed. As a result, the temperature of heat generation is sustained for an extended period of time. Having no intermediate between the air permeable sheet 5 and the heat generating sheet 2, the warming device 1 is thin, flexible, convenient to carry, and excellent in heat generating performance. Since the flexibility is maintained even after use, the warming device 1 can easily be disposed of in a folded form, rolled form or the like.

Figure 2:
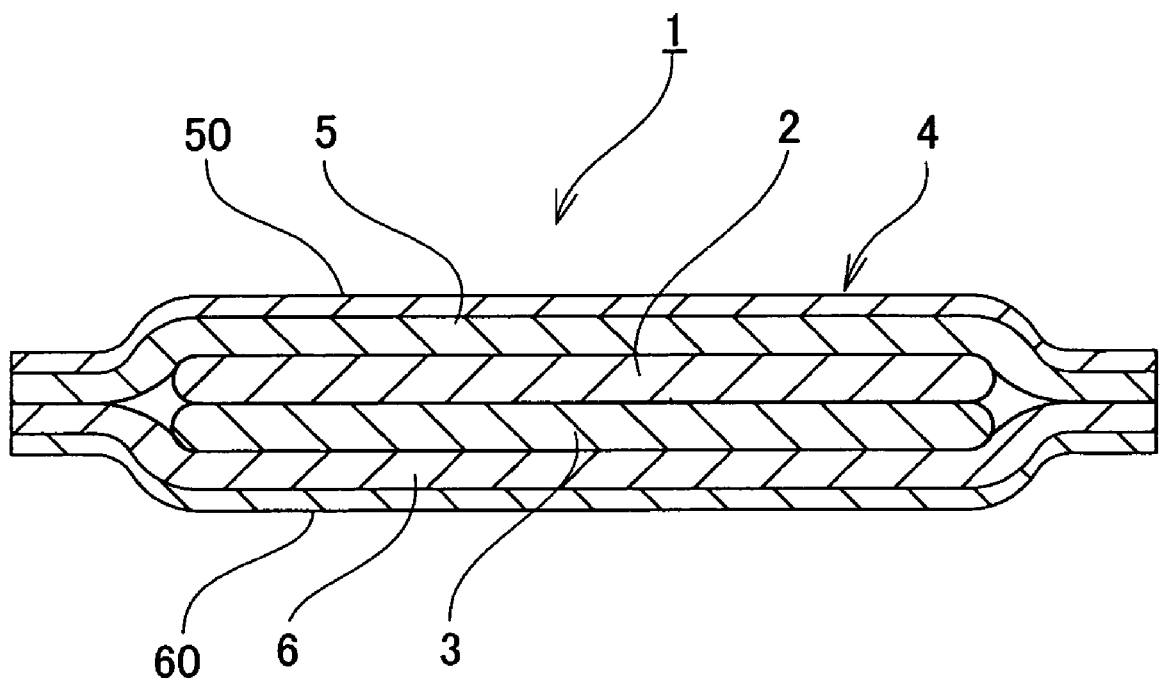
FIG. 2 is a schematic cross-sectional view of a second embodiment of the warming device according to the present invention.

FIG. 2 illustrates a second embodiment of the warming device according to the present invention, in which numeral 1 indicates a warming device. Elements in FIG. 2 common to the warming device 1 of the first embodiment are given the same reference numerals. The description about the first embodiment applies as appropriate to the elements of the second embodiment that are not described hereunder.

As illustrated in FIG. 2, the warming device 1 has a heat generating sheet 2 prepared by papermaking process (hereinafter referred to as a molded sheet) and a heat insulating sheet 3 held in an air permeable holder 4. In what follows, a molded sheet free of an electrolyte (described later) is called a heat generating sheet precursor, and a molded sheet containing the electrolyte and water is called a heat generating sheet.

The holder 4 of the warming device 1 is formed of an air permeable sheet 5 and an air impermeable sheet 6. The heat insulating sheet 3 is interposed between the molded sheet 2 and the air impermeable sheet 6. There is no heat insulating sheet 3 between the air permeable sheet 5 and the molded sheet 2. The heat insulating sheet 3 is disposed between the molded sheet 2 and the air impermeable sheet 6.

The warming device 1 of the second embodiment has a flexural strength of 0.01 to 1.0 N/cm, preferably 0.02 to 0.8 N/cm, more preferably 0.03 to 0.5 N/cm. With the flexural strength falling within the recited range, the warming device 1 is highly flexible, easily foldable, and therefore convenient to carry. The flexural strength is measured in three-point bending flexural test.

It is desirable for the warming device 1 to have a flexural strength of 0.05 to 3.0 N/cm, more preferably 0.02 to 1 N/cm, after heat generation comes to an end. Within that range, the warming device 1 keeps flexible from start to end of use and is easily disposed of after use.

The heat generating sheet 2 preferably has a basis weight of 10 to 2000 g/m$^2$, more preferably 50 to 1500 g/m$^2$. The heat generating sheet 2 having a basis weight of 10 g/m$^2$ or more is produced in a stable manner. The heat generating sheet 2 having a basis weight of 2000 g/m$^2$ or less is favorable for comfort of use.

In the second embodiment, the heat insulating sheet 3 may or may not have air permeability, preferably has no air permeability.

It is more preferred that the heat insulating sheet 3 have neither air permeability nor water retentivity. Where the heat insulating sheet has water retentivity, it would absorb water vapor generated in the oxidation reaction of the oxidizable substance. As a result, the heat generating sheet steeply reduces its water content, and the moisture retained in the heat insulating sheet comes into contact with the heat generating sheet. It can follow that the heat generation duration is shortened and that the temperature of the heat varies. When an air permeable sheet is used as the heat insulating sheet 3, it is desirable to superpose an air impermeable sheet on the heat insulating sheet, particularly the side facing the heat generating sheet 2.

The heat insulating sheet 3 includes foamed polyethylene, foamed polyurethane, foamed polystyrene, foamed melamine, bubble film, a bulky pulp sheet, corrugated paper, woven fabric, nonwoven fabric and etc. Above all, a heat insulating sheet made of foam is preferably used for its light weight, flexibility, and cushioning properties. To laminate or deposit aluminum foil on a heat insulating sheet is preferred; for the warming effect is enhanced by radiant heat.

Similarly to the warming device 1 of the first embodiment, the warming device 1 of the second embodiment is produced by, for example, interposing a heat generating sheet 2, which is prepared as described below, and the heat insulating sheet 3 at a prescribed position between the sheets making up the holder 4, bonding the periphery of the air permeable sheet 5, the air impermeable sheet 6, the surfacing members 50 and 60 to enclose the heat generating sheet 2, and cutting the laminate into a prescribed shape.

The warming device 1 thus obtained is thin, flexible, convenient to carry, and excellent in heat generating performance. Since the flexibility is maintained even after use, the warming device 1 can easily be disposed of in a folded form, rolled form or the like.

Figure 3:
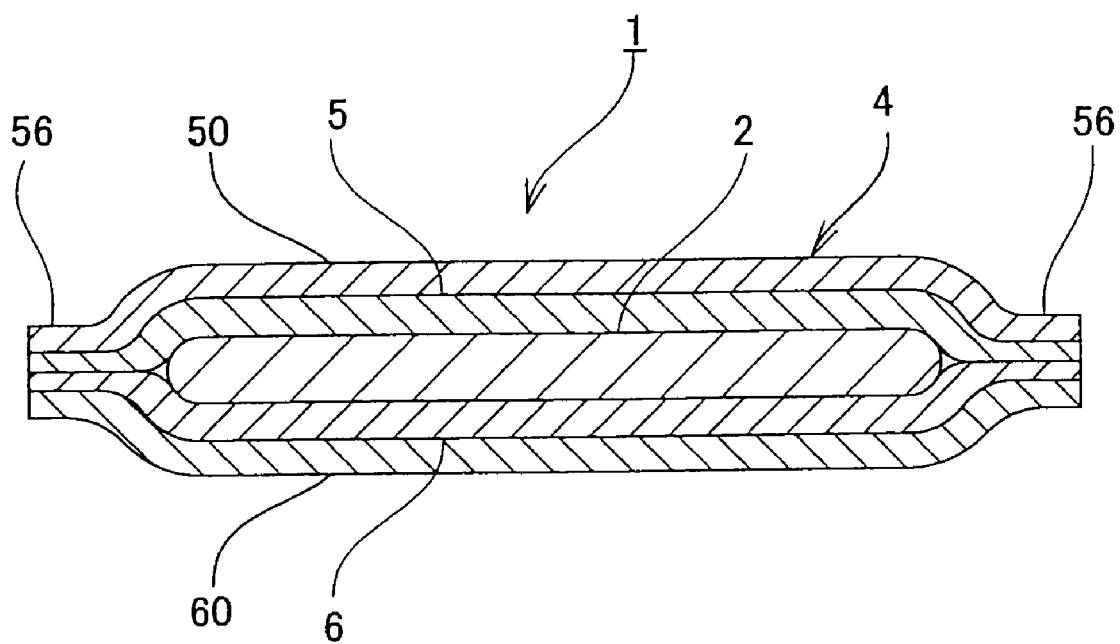
FIG. 3 is a schematic cross-sectional view of a third embodiment of the warming device according to the present invention.

FIG. 3 illustrates a third embodiment of the warming device according to the present invention, in which numeral 1 indicates a warming device. Elements in FIG. 3 common to the warming device 1 of the first embodiment are given the same reference numerals. The description about the first embodiment applies as appropriate to the elements of the third embodiment that are not described hereunder.

As illustrated in FIG. 3, the warming device 1 has a heat generating sheet 2 containing an oxidizable metal, a moisture retaining agent, and a fibrous material and prepared by papermaking process (hereinafter referred to as a molded sheet) and an air permeable holder 4 for holding the molded sheet 2. In what follows, a molded sheet free of an electrolyte (described later) is called a heat generating sheet precursor, and a molded sheet containing the electrolyte and water is called a heat generating sheet.

The warming device 1 has a thickness of 0.1 to 10 mm, preferably 0.3 to 3.0 mm, more preferably 0.5 to 2.0 mm. If the thickness is less than 0.1 mm, it has poor heat generating performance and steam generating performance, failing to exert sufficient effects as a warming device. If the thickness exceeds 10 mm, the warming device has poor flexibility and feels stiff and rough to the touch when applied to a part of the body or tends to harden during use, resulting in poor usability.

The warming device 1 has a flexural strength of 0.01 to 0.3 N/cm, preferably 0.02 to 0.25 N/cm, more preferably 0.03 to 0.2 N/cm. If the flexural strength is less than 0.01 N/cm, heat generation to moderate temperatures is not obtained. If the flexural strength exceeds 0.3 N/cm, the warming device 1 has poor flexibility and feels discomfort to wear. The flexural strength is measured in three-point bending flexural test.

It is desirable for the warming device 1 to have a flexural strength of 0.05 to 3.0 N/cm, more preferably 0.02 to 1 N/cm, after heat generation comes to an end. Within that range, the warming device 1 keeps flexible and conformable from start to end of use.

The warming device 1 preferably has a basis weight of 100 to 3000 g/m$^2$, more preferably 200 to 1500 g/m$^2$. With the basis weight being within that range, the warming device 1 is thin, flexible, and conformable.

The heat generating sheet 2 preferably has a thickness of 0.08 to 2.0 mm, more preferably 0.2 to 1.5 mm. Within that thickness range, the warming device 1 is thin, flexible, and agreeable to the touch while in use.

The heat generating sheet 2 contains an oxidizable metal, a moisture retaining agent, and a fibrous material.

The heat generating sheet precursor 2 preferably contains at least 50% by weight, more preferably 70% by weight or more, even more preferably 80% by weight or more, of components other than the fibrous material. When the content of the components other than the fibrous material is 50% by weight or more, the heat generating sheet heats up to or above the temperature feeling hot when touched with the finger or the like. The higher the content of the components other than the fibrous material, the more preferred. Nevertheless, the upper limit is about 98% by weight for assuring strength necessary to maintain fabricability of the heat generating sheet precursor 2. The proportion of the components other than the fibrous material is measured as follows.

The proportion of the components other than the fibrous material in the heat generating sheet precursor 2 is calculated from the solids weight and composition of a raw material composition and the dry weight of the heat generating sheet precursor according to formula:

$$b=(Mh/Ms)\times(100-a)$$

wherein
b: content of components other than fibrous material in heat generating sheet precursor
Mh: dry weight of heat generating sheet precursor
Ms: solids weight of raw material composition
a: percentage of fibrous material in solids content of raw material composition The oxidizable metal can be of any kind that is commonly employed in this type of heat generating molded articles. The oxidizable metal is preferably in the form of powder or fiber from the standpoint of ease in handling molding capabilities, and the like.

Oxidizable metals in the form of powder include the oxidizable substances listed above with reference to the warming device of the first embodiment.

Oxidizable metals in the form of fiber include the oxidizable substances listed above with reference to the warming device of the first embodiment.

The proportion of the oxidizable metal in the heat generating sheet precursor 2 is preferably 10% to 95% by weight, more preferably 30% to 80% by weight. With 10% by weight or more of the oxidizable metal, the resulting heat generating sheet 2 sufficiently heats up to or above the temperature feeling hot to the touch of fingers, etc., and with the proportions of the fibrous material and a binding component (e.g., a flocculant), which constitute the heat generating sheet as hereinafter described, being so controlled, the heat generating sheet 2 is comfortable to use in terms of hardness. With the oxidizable metal content being 95% by weight or less, the following advantages are offered. The reaction takes place sufficiently in the inside of the heat generating sheet 2 to sufficiently raise the temperature. Hardening of the oxidizable metal due to setting expansion on oxidation is relatively suppressed. The duration of heat generation is sufficient a water vapor supply by the moisture retaining agent is secured. The oxidizable metal hardly falls off the sheet. Certain proportions of the fibrous material and binding component hereinafter described, which make up the heat generating sheet 2, are secured to assure mechanical strength characteristics such as flexural strength and tensile strength. The oxidizable metal content in the heat generating sheet 2 can be determined by determination of ash in accordance with JIS P8128. Vibrating sample magnetization measurement is useful in the case of iron, of which the magnetization on applying an external magnetic field is made use of.

The moisture retaining agent includes any moisture retaining agents commonly employed in heat generating molded articles with no particular limitation. The moisture retaining agent not only serves for moisture retention but functions as an agent for holding and supplying oxygen to the oxidizable metal. Examples of useful moisture retaining agents include those recited with respect to the warming device of the first embodiment.

The moisture retaining agent is preferably present in the heat generating sheet precursor 2 in an amount of 0.5% to 60% by weight, more preferably 1% to 50% by weight. With a moisture retaining agent content of 0.5% by weight or more, the heat generating sheet 2 holds a requisite water content for the oxidizable metal to sustain oxidation reaction for maintaining the temperature at or above the body temperature. Furthermore, the heat generating sheet 2 has sufficient air permeability for oxygen supply to achieve high heat generation efficiency. With the moisture retaining agent content being 60% by weight or less, the following advantages are offered. The heat generating sheet 2 has a controlled heat capacity for the amount of heat generated to show a sufficient temperature rise. The moisture retaining agent hardly falls off. Sufficient amounts of the fibrous material and binding component hereinafter described, which build up the heat generating sheet 2, are secured to assure sufficient mechanical strength such as flexural strength and tensile strength.

The fibrous material includes those enumerated for the warming device of the first embodiment.

The fibrous material content in the heat generating sheet precursor 2 is preferably 2% to 50% by weight, more preferably 5 to 40% by weight. Where the content is less than 2% by weight, the effect for preventing the oxidizable metal, the moisture retaining agent, etc. from falling off is reduced, and the heat generating sheet 2 tends to be very brittle. If the fibrous material content is more than 50% by weight, the heat generating sheet 2 will have an increased heat capacity for the amount of heat generated, and a reduced rise in temperature results. Furthermore, the proportion of the other components is so low that the resulting heat generating sheet 2 can fail to exhibit desired heat generating performance.

The thickness of the heat generating sheet precursor 2 is preferably 0.08 to 1.2 mm, more preferably 0.1 to 0.6 mm. A thickness of 0.08 mm or more assures sufficient heat generating performance, mechanical strength, fixation of the oxidizable metal, the moisture retaining agent, etc., and uniformity (stability) in thickness and composition. A thickness of 0.08 mm or more is also preferred in productivity and fabricability because defects, such as break of the sheet due to pinhole development, hardly occur. A sheet with a thickness of 1.2 mm or less has folding strength, flexibility and, in particular, good conformability to fit a bending part of a body, such as an elbow, a knee, and the face. In addition, the time for papermaking and drying is relatively short to provide good operationality. The thickness is also preferred in fabricability. The thickness of the heat generating sheet precursor is obtained by taking measurements at five or more different points in accordance with JIS P8118 and averaging the results.

The basis weight of the heat generating sheet precursor 2 is preferably 10 to 1000 g/m$^2$, more preferably 50 to 600 g/m$^2$. Even in using, for example, an oxidizable metal having a high specific gravity, a sheet having a basis weight of 10 g/m$^2$ or more can be formed stably. A sheet weighing 1000 g/m$^2$ or less is satisfactory in usability, productivity, and operationality. The basis weight of the heat generating sheet precursor 2 is calculated by dividing the weight of the sheet of an area of at least 100 cm$^3$ by the area.

It is preferred for the heat generating sheet precursor 2 to have a density of 0.6 to 1.5 g/cm$^3$, more preferably 0.7 g/cm$^3$ to 1.0 g/cm$^3$. In the heat generating sheet precursor having a density of 0.6 g/cm$^3$ or higher, the oxidizable metal and other components are in good entanglement with each other, which is favorable for strength. The heat generating sheet precursor having a density of 1.5 g/cm$^3$ or lower has sufficient air permeability to exhibit its heat generation characteristics to the full. The density of the heat generating sheet precursor 2 is calculated by dividing the basis weight by the thickness.

It is preferred for the heat generating sheet precursor 2 to have a breaking length of 100 to 4000 m, more preferably 200 to 3000 m. With a breaking length of 100 m or longer, the sheet is formed in a stable manner during the production operation; the resulting sheet is fabricated in a stable manner; and the final product has sufficient strength for sufficient usability. A heat generating sheet precursor 2 with a breaking length of 4000 m or less contains moderately controlled amounts of the fibrous material and the binding component as the sheet-forming components and is therefore flexible and excellent in heat generating performance.

The heat generating sheet 2 contains an electrolyte.

Any kind of electrolytes commonly employed in this type of heat generating molded articles can be used with no particular restrictions. Examples of useful electrolytes include those recited for the warming device of the first embodiment.

The electrolyte is preferably used in an amount of 0.5% to 30% by weight, more preferably 1% to 25% by weight, based on the water content of the heat generating sheet 2. At the electrolyte content of 0.5% by weight or more, the oxidation reaction proceeds sufficiently in the resulting heat generating sheet 2, and a sufficient temperature rise is achieved. At the electrolyte content of 30% by weight or less, satisfactory air permeability of the heat generating sheet 2 is retained, and a sufficient amount of water is supplied to the oxidizable metal, etc. to assure high heat generating performance. The electrolyte of that amount can uniformly be distributed throughout the heat generating sheet 2.

The thickness of the heat generating sheet 2 is preferably 0.1 to 2.0 mm, more preferably 0.15 to 1.8 mm. A heat generating sheet 2 having a thickness of 0.1 mm or more exhibits sufficient heat generating performance and mechanical strength. A sheet with a thickness of 2 mm or less has sufficient flexibility and provides comfort of use. The thickness of the heat generating sheet is obtained by taking measurements at five or more different points in accordance with JIS P8118 and averaging the results.

The heat generating sheet 2 preferably has a basis weight of 10 to 2000 $g/m^2$, more preferably 50 to 1500 $g/m^2$. The heat generating sheet 2 having a basis weight of 10 $g/m^2$ or more is produced in a stable manner. The heat generating sheet 2 having a basis weight of 2000 $g/m^2$ or less is favorable for comfort of use.

It is preferred for the heat generating sheet 2 to have a density of 0.6 to 3.0 $g/cm^3$, more preferably 0.7 to 1.0 $g/cm^3$. In the heat generating sheet having a density of 0.60 $g/cm^3$ or higher, the oxidizable metal and other components are in good entanglement with each other, which assures sufficient strength and prevents constituent components from falling off to secure productivity and fabricability. The heat generating sheet having a density of 1.50 $g/cm^3$ or lower is soft enough to provide conformability, pleasant feel to the touch, and usability and has sufficient air permeability to exhibit excellent heat and steam generating performance. The density of the heat generating sheet 2 is calculated by dividing the basis weight by the thickness.

The temperature reached by the heat generating sheet 2 on heat generation is preferably 30° to 100° C., more preferably 35° to 90° C. The temperature reachable by the heat generating sheet 2 can freely be designed by the formulation of the components according to the purpose, that is, whether a steep temperature rise is needed or a long duration of heat generation at a relatively low temperature is desired, and the like.

It is desirable for the heat generating sheet 2 to generate 1 to 100 $mg/(cm^2 \cdot 10\ min)$, more preferably 1.0 to 50 $mg/(cm^2 \cdot 10\ min)$, of water vapor per unit area for 10 minutes.

Similarly to the time required for reaching the maximum temperature of heat generation, the amount of water vapor produced can be freely designed by the formulation of the components according to the purpose, that is, whether a steep temperature rise is desired or a long duration of heat generation at a relatively low temperature is desired, and the like.

The water content of the heat generating sheet 2 is preferably 10% to 80% (by weight, hereinafter the same), more preferably 20% to 60%. With a water content of 10% or more, a water vapor necessary for continuing oxidation reaction is secured to allow the oxidation reaction to proceed sufficiently. Furthermore, a water vapor can be distributed uniformly throughout the heat generating sheet 2 to assure uniform heat generation. With a water content of 80% or less, the heat generating sheet 2 has a controlled heat capacity for the amount of heat generated to achieve a sufficient rise in temperature; sufficient air permeability is secured to assure high heat generating performance; and the sheet 2 is excellent in shape retention and mechanical strength.

The holder 4 is not particularly limited as long as it has air permeability and prevents fall-off of the components constituting the heat generating sheet 2. To have the heat generating sheet 2 exhibit sufficient heat generation characteristics, the holder 4 preferably has a water vapor permeability of 100 to 10000 $g/(m^2 \cdot 24\ hr)$, more preferably 1000 to 8000 $g/(m^2 \cdot 24\ hr)$. The holder 4 has air permeability either wholly or partially.

In the third embodiment, the holder 4 of the warming device 1 is made by joining the air permeable sheet 5 and the air impermeable sheet 6 along their peripheral joint 56 with a prescribed width to enclose the heat generating sheet 2 therebetween.

The warming device 1 has a surfacing member 60 on the surface of the air impermeable sheet 6. The surfacing member 60 is not particularly limited in material, production process, and etc. Nevertheless, where a functional preparation is added to the surfacing member 60 as hereinafter described, retentivity for such a functional preparation should be taken into consideration. The surfacing member 60 includes nonwoven fabric made of synthetic fibers, natural fibers or composite fibers thereof. Production processes include spun bonding, needle punching, hydroentanglement, melt blowing, flash spinning, air laying, through-air processing, papermaking and the like. Taking functional preparation retentivity into consideration, hydroentanglement is preferred for its applicability to fibers having high water and oil retentivity exemplified by rayon, cotton and etc.

While the basis weight per of the surfacing member 60 is not particularly limited, it is preferably 5 to 200 $g/m^2$, more preferably 10 to 100 $g/m^2$, from the standpoint of functional preparation retentivity.

It is preferred that the warming device 1 of the third embodiment contain a functional preparation of various kinds in the surfacing member 60. Examples of useful functional preparations include packs and cataplasms for skin care and health care applications; moisturizers, agents for eliminating skin dullness, wrinkle removers and etc. for beauty care applications; hair colors, conditioners, hair growth formulas and etc. for personal care applications; cleaners, sanitizers, and deodorants for home care applications; and slow release fragrances for air care applications.

The moisturizers, in particular, include polyols such as glycerol, ceramids, collagens and etc. The moisturizer and heat produce synergistically enhanced moisturizing effect to give a water vapor and bounciness to the skin. The cataplasms include anti-inflammatory agents such as indometacin and methyl salicylate. Percutaneous absorption of the cataplasm is synergistically accelerated by the heat to effectively relieve pains in muscles, joints, lower back, etc.

Where a functional preparation is held by the surfacing member 60, the functional preparation is preferably covered with a covering layer. Useful covering layers include a sheet of resins such as polyolefins (e.g., PE and PP), polyester, polyamide, polyurethane, polystyrene, nylon, polyvinylidene chloride, and an ethylene-vinyl acetate copolymer, etc.

The warming device of the present invention can have a buffer material. Providing a buffer material imparts cushioning properties, keep warm properties, and heat insulation properties to the warming device. While the buffer material is not particularly restricted in form, a buffer of sheet form is preferred in view of ease of producing the warming device, ease of adjusting the thickness of the warming device, uniformity and controllability of the heat generation temperature, and the like. The buffer material preferably has a thickness of 0.2 to 9 mm, more preferably 0.5 to 8 mm, taking into consideration commodity performance, such as thermal conductivity to an object to be treated (e.g., a human body) and degree of steam generation, and commodity form, such as bulkiness, portability, and disposability. The buffer material of sheet form preferably has a thickness of 0.2 to 6 mm, more preferably 0.5 to 3 mm, and a density of 0.005 to 0.9 $g/cm^3$, more preferably 0.01 to 0.6 g/cm³. It is preferred for the buffer material not to have liquid retentivity with consideration given to improvement in exothermic reaction efficiency, controllability of heat generation temperature, and improvement in heat generation duration. Where a liquid retentive buffer material is used, it would absorb water vapor generated upon exothermic reaction, which can interfere with further exothermic reaction. There are cases in which a commodity design requires use of an air permeable buffer material. Because most of air permeable buffer materials have more or less liquid retentivity, such a design can be realized by laminating the buffer material with an air-permeable but a water vapor impermeable sheet. Examples of useful buffer materials include foamed polyethylene, foamed polyurethane, foamed polystyrene, foamed melamine, bubble film, and a bulky pulp sheet, corrugated paper, woven fabric nonwoven fabric, etc., laminated with a water impermeable film. Above all, a buffer material made of foamed polyethylene is preferably used for its light weight, flexibility, and cushioning properties. To laminate or deposit aluminum foil, etc. on a buffer material of sheet form is preferred; for the warming effect is enhanced by radiant heat.

The warming device 1 is produced by, for example, interposing a heat generating sheet 2, which is prepared as described below, at a prescribed position between the sheets making up the holder 4, bonding the periphery of the air permeable sheet 5, the air impermeable sheet 6, the surfacing members 50 and 60 to enclose the heat generating sheet 2, and cutting the laminate into a prescribed shape. Where the surfacing member 60 holds the above-mentioned functional preparation, it is preferred to add the functional preparation after the cutting.

The heat generating sheet 2 is prepared using a raw material composition (slurry) containing the oxidizable metal, moisture retaining agent, fibrous material, and water in the same manner as described with respect to the warming device of the first embodiment.

As described, the warming device 1 of the third embodiment is thin, flexible, and agreeable to the touch while in use. The warming device 1 of the third embodiment is applicable to a wide variety of applications, taking advantage of the heat and steam generating function combined with the function of various functional preparations. For example, it can be combined with a facial pack to provide a hot pack for skin care applications, such as a water vapor retention or reduction of wrinkles, or it can be combined with cataplasm to provide a hot cataplasm for health care applications, such as reduction of hand pain.

Where steam liberated from the side of the air permeable sheet 5 is first applied to an object to be treated, and then the functional preparation on the side of the air impermeable sheet 6 is made to act on the object, the function of the functional preparation is enhanced. For instance, the efficacy of a pack as a functional preparation is enhanced by first applying steam to the skin to open the pores and then making the pack act thereon. The effect of a cleaner as a functional preparation can be increased by first applying steam to soften dirt, etc.

Figure 4:
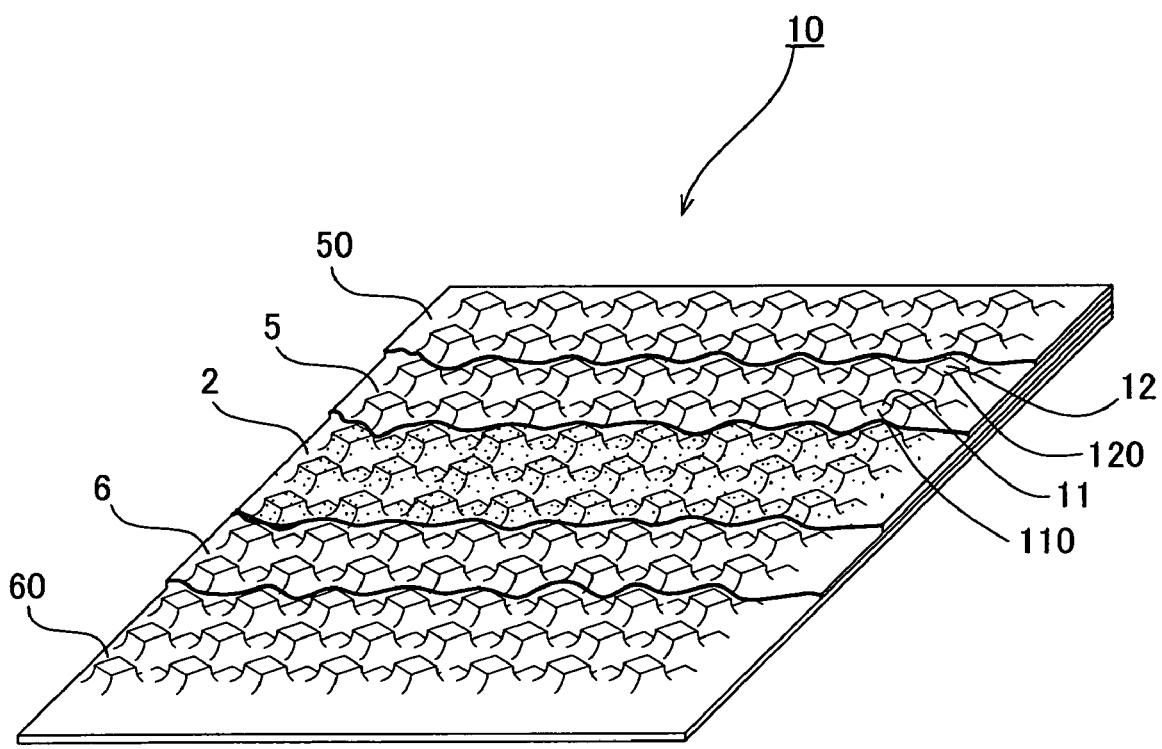
FIG. 4 is a perspective view of an embodiment of the heat generating molded article according to the present invention with part cut away.
Figure 5A:
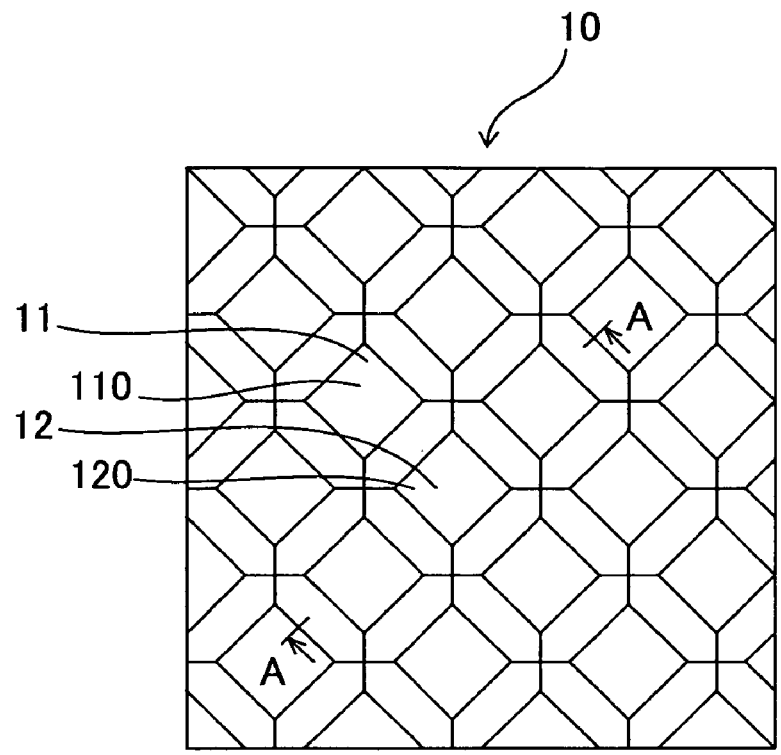
FIG. 5($a$) is an enlarged plan view of a part of the heat generating molded article shown in FIG. 4.
Figure 5B:
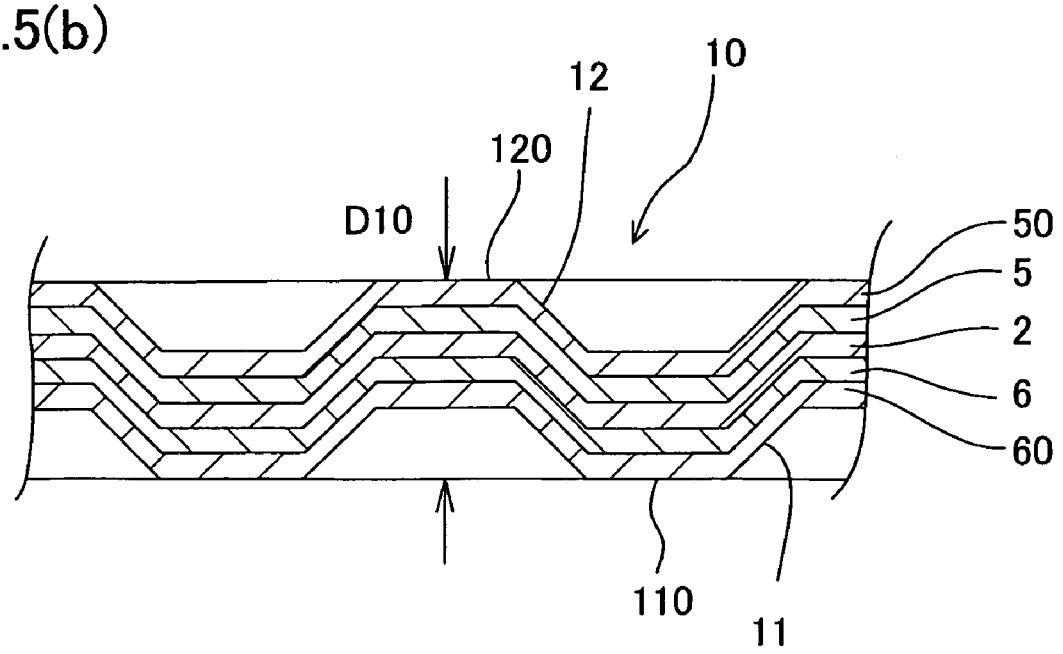

FIGS. 4, 5(a), and 5(b) show an embodiment of the heat generating molded article as a fourth embodiment of the present invention. In the figures numeral 10 indicates a heat generating molded article. Elements common to the warming device 1 of the first embodiment are given the same numerals. The description about the first embodiment applies as appropriate to the elements of the fourth embodiment that are not described hereunder.

As illustrated in FIGS. 4, 5(a), and 5(b), the heat generating molded article 10 has a heat generating sheet 2 containing an oxidizable metal, a moisture retaining agent and a fibrous material, an air permeable sheet 5 on one side of the heat generating sheet 2, an air impermeable sheet 6 on the other side of the heat generating sheet 2, and surfacing members 50 and 60 on the air permeable sheet 5 and the air impermeable sheet 6, respectively. In what follows, the sheet 2 free of an electrolyte (described later) is called a heat generating sheet precursor 2, and the sheet 2 containing the electrolyte and water is called a heat generating sheet.

The heat generating molded article 10 having the above-described layer structure has a large number of depressions 11 and productions 12 embossed on both sides thereof by means of matched steel embossing rolls. In this particular embodiment, the bottom 110 of the depression 11 and the top 120 of the projection 12 are both square-shaped, and the depressions 11 and the projections 12 are arranged in a diamond lattice pattern.

The level difference between the projections and the depressions is preferably 0.3 to 5 mm, more preferably 0.5 to 4 mm. With this difference, heat generating properties of the resulting heat generating molded article and shapability by embossing are secured. The level difference between the projections and the depressions is obtained from a distance D10 between the bottom 110 of the depressions 11 and the top 120 of the projection 12.

The bottom 110 of the individual depressions 11 and the top 120 of the individual projections 12 each preferably have an area of 0.01 to 100 mm², more preferably 0.1 to 25 mm². With this area, when two or more heat generating sheets and/or two or more a water vapor permeable sheets are stacked, the stack can be united and prevented from sliding.

The number of the bottoms 110 of the depressions 11 and the tops 120 of the projections 12 in an area of 10 cm² of the heat generating molded article 10 is preferably 1 to 10000, more preferably 10 to 8000. With that number of the bottoms 110 and the tops 120, when two or more heat generating sheets and/or two or more a water vapor permeable sheets are stacked, the stack can be united and prevented from sliding.

The basis weight of the heat generating molded article 10 is preferably 10 to 1000 g/m², more preferably 50 to 600 g/m². Even in using, for example, an oxidizable metal having a high specific gravity, a sheet having a basis weight of 10 g/m² or more can be formed stably. A sheet weighing 1000 g/m² or less feels light and good while worn and is also preferred from the standpoint of productivity and operationality.

The temperature reached by the heat generating molded article 10 on heat generation is preferably 30° to 100° C., more preferably 35° to 90° C. The temperature reachable by the heat generating molded article 10 can freely be designed by the formulation of the components according to the purpose, that is, whether a steep temperature rise is needed or a long duration of heat generation at a relatively low temperature is desired, and the like.

It is desirable for the heat generating molded article 10 to generate 0.1 to 100 mg/(cm²·10 min), more preferably 1 to 50 mg/(cm²·10 min), of water vapor per unit area for 10 minutes.

Similarly to the time required for reaching the maximum temperature of heat generation, the amount of water vapor produced by the heat generating molded article 10 can be freely designed by the formulation of the components according to the purpose, that is, whether a steep temperature rise is desired or a long duration of heat generation at a relatively low temperature is desired, and the like.

The oxidizable metal used in the heat generating sheet precursor 2 can be of any kind that is commonly employed in this type of heat generating molded articles. The oxidizable metal is preferably in the form of powder or fiber from the standpoint of ease in handling and molding properties.

Oxidizable metals in the form of powder include the oxidizable substances listed above with reference to the warming device of the first embodiment.

The proportion of the oxidizable metal in the heat generating sheet precursor 2 is preferably 10% to 95% by weight, more preferably 30% to 80% by weight. Where the proportion of the oxidizable metal is 10% by weight or more, the following advantages are offered. The resulting heat generating molded article 10 heats up to or above the temperature feeling hot when touched with the fingers or the like. Since the proportions of the fibrous material and a binding component (e.g., a flocculant) hereinafter described, which constitute the heat generating sheet 2, are controlled, sufficient air permeability of the molded sheet is assured, so that the reaction takes place sufficiently in the inside of the heat generating molded article to sufficiently raise the temperature. The duration of heat generation is sufficient a water vapor supply by the moisture retaining agent is secured. Fall-off of the oxidizable metal hardly occurs. The molded sheet contains certain proportions of the fibrous material and binding component hereinafter described, which make up the molded sheet, to secure mechanical strength characteristics such as flexural strength and tensile strength. The oxidizable metal content in the heat generating sheet precursor 2 can be determined by determination of ash in accordance with JIS P8128. Vibrating sample magnetization measurement is useful in the case of iron, of which the magnetization on applying an external magnetic field is made use of.

The moisture retaining agent includes any moisture retaining agents commonly employed in heat generating molded articles with no particular limitation. The moisture retaining agent not only serves for a water vapor retention but functions as an agent for holding and supplying oxygen to the oxidizable metal. Examples of useful moisture retaining agents include those recited with respect to the warming device of the first embodiment.

The proportion of the moisture retaining agent in the heat generating sheet precursor 2 is preferably 0.5% to 60% by weight, more preferably 1% to 50% by weight. With a moisture retaining agent content of 0.5% by weight or more, the heat generating molded article 10 holds a requisite water content for sustaining sufficient oxidation reaction for maintaining the temperature at or above the body temperature. Furthermore, the heat generating molded article 10 has sufficient air permeability for oxygen supply to assure high heat generation efficiency. With the moisture retaining agent content being 60% by weight or less, the following advantages are offered. The heat generating molded article 10 has a controlled heat capacity for the amount of heat generated to show a sufficient temperature rise to a degree that can be felt with the body. The moisture retaining agent hardly falls off. Sufficient amounts of the fibrous material and binding component hereinafter described, which build up the heat generating sheet 2, are secured to provide sufficient mechanical strength such as flexural strength and tensile strength.

The fibrous material includes those enumerated for the warming device of the first embodiment.

The fibrous material content in the heat generating sheet precursor 2 is preferably 2% to 50% by weight, more preferably 5% to 40% by weight. With the fibrous material content of 2% by weight or more, fall-off of the other components such as the oxidizable metal and the moisture retaining agent is sufficiently prevented, and the resulting heat generating sheet becomes sufficient. With the fibrous material content of 50% by weight or less, the heat generating molded article has a controlled heat capacity for the amount of generated heat to show a sufficient temperature rise. Furthermore, certain proportions of the other components are secured to develop sufficient heat generating performance as desired.

The heat generating sheet precursor 2 preferably contains at least 50% by weight, more preferably 70% by weight or more, even more preferably 80% by weight or more, of components other than the fibrous material. When the content of the components other than the fibrous material is 50% by weight or more, the temperature of heat generation rises to a degree such that the heat generating molded article feels hot when touched with the fingers. The higher the content of the components other than the fibrous material, the more preferred. Nevertheless, the upper limit is 98% by weight for assuring strength necessary to maintain fabricability of the heat generating sheet 2.

The thickness of the heat generating sheet precursor 2 is preferably 0.08 to 1.2 mm, more preferably 0.1 to 0.6 mm. A heat generating sheet precursor 2 having a thickness of 0.08 mm or more exhibits excellent heat generating performance, mechanical strength, sufficient fixation of the oxidizable metal, the moisture retaining agent, etc., and uniformity (stability) in thickness and composition. A thickness of 0.08 mm or more is also preferred in productivity and fabricability because defects, such as break of the sheet due to pinhole development, hardly occur. A sheet with a thickness of 1.2 mm or less has the following advantages. The sheet has enough folding strength not to undergo brittle fracture easily. The sheet has satisfactory flexibility to provide conformability particularly to fit a bending part of a body, such as an elbow, a knee, and the face. Prolongation of the papermaking and drying time is hardly needed to provide good operationality. The sheet exhibits satisfactory heat generating performance and excellent fabricability in bending or like processing.

The basis weight of the heat generating sheet precursor 2 is preferably 10 to 1000 g/m$^2$, more preferably 50 to 600 g/m$^2$. Even in using, for example, an oxidizable metal having a high specific gravity, a sheet having a basis weight of 10 g/m$^2$ or more can be formed stably. A sheet weighing 1000 g/m$^2$ or less is light enough to be convenient to use and also advantageous for productivity, operationality and the like.

It is preferred for the heat generating sheet precursor 2 to have a breaking length of 100 to 4000 m, more preferably 200 to 3000 m. With a breaking length of 100 m or longer, the heat generating sheet is prevented from being broken or cut when embossed, and the product is highly usable without easily crumbling due to lack of elasticity while in use. A heat generating sheet precursor 2 with a breaking length of 4000 m or less contains moderately controlled amounts of the fibrous material and the binding component as the sheet-forming components and is therefore flexible and excellent in heat generating performance.

The electrolyte used in the heat generating sheet 2 is not particularly limited, and any kind commonly used in this type of heat generating molded articles can be used. Examples of useful electrolytes include those recited for the warming device of the first embodiment.

The electrolyte is preferably added in an amount of 0.5% to 30% by weight, more preferably 1% to 25% by weight, based on the water content of the resulting heat generating sheet 2. At the electrolyte content of 0.5% by weight or more, the oxidation reaction proceeds sufficiently in the resulting heat generating molded article 10, and the water content of the heat generating sheet 2 necessary to maintain the requisite amount of the electrolyte for heat generation is controlled. As a result, reduction in temperature rise of the heat generating molded article 10 is avoided. At the electrolyte content of 30% by weight or less, precipitation of the electrolyte hardly occurs, and the heat generating molded article 10 maintains satisfactory air permeability. A certain proportion of water is held in the heat generating molded article 10 for securing a necessary amount of the electrolyte for heat generation so that a sufficient amount of water is supplied to the oxidizable metal, etc. to assure high heat generating performance. The electrolyte of that amount can uniformly be distributed throughout the heat generating molded article 10.

The water content of the heat generating sheet 2 is preferably 10% to 80% (by weight, hereinafter the same), more preferably 20% to 60%. With a water content of 10% or more, a water vapor necessary for continuing oxidation reaction is secured thereby preventing the oxidation reaction from ceasing halfway. Furthermore, uniformity of a water vapor distribution throughout the heat generating molded article 10 is assured, leading to uniform heat generation. With a water content of 80% or less, the heat generating molded article 10 has a controlled heat capacity for the amount of heat generated, which promises a sufficient rise in temperature. Besides, the air permeability of the heat generating molded article 10 is sufficient so that high heat generating performance and sufficient shape retention and mechanical strength are secured.

The temperature reached by the heat generating sheet 2 on heat generation is preferably 30° to 100° C., more preferably 35° to 90° C. The temperature reachable by the heat generating sheet 2 can freely be designed by the formulation of the above-described components according to the intended use of commodities.

It is desirable for the heat generating sheet 2 to generate 0.1 to 100 mg/(cm$^2$·10 min), more preferably 1 to 50 mg/(cm$^2$·10 min), of water vapor. Similarly to the time for reaching the highest temperature, the amount of water vapor to be generated by the heat generating sheet 2 is freely designed by the formulation of the above-described components according to the intended use of commodities.

The air permeable sheet 5 is not particularly limited as long as it has air permeability. The water vapor permeability of the air permeable sheet 5 is preferably 10 to 10000 g/(m$^2$·24 hr), more preferably 100 to 8000 g/(m$^2$·24 hr). With the water vapor permeability being in that range, oxygen is supplied smoothly to enable rapid heat and steam generation. The air permeable sheet 5 may have air permeability all over the entire area or partly.

The air permeable sheet 5 preferably has a basis weight of 10 to 200 g/m$^2$, more preferably 20 to 100 g/m$^2$. The air permeable sheet 5 whose basis weight is in that range does not impair the flexibility of the heat generating element and prevents sheet breakage during embossing.

Materials of the air permeable sheet 5 include those of the air permeable sheet used in the warming device of the first embodiment.

The air impermeable sheet 6 is not particularly limited as long as it is impermeable to air. The air impermeable sheet 6 preferably has a water vapor permeability of 10 g/(m$^2$·24 hr) or less, more preferably 1 g/(m$^2$·24 hr) or less.

The air impermeable sheet 6 preferably has a basis weight of 10 to 200 g/m$^2$, more preferably 20 to 100 g/m$^2$. The air impermeable sheet 6 having a basis weight within that range controls the direction of release of water vapor co-generated with heat generation and exhibits improved capability of hiding the heat generating element while retaining the softness and flexibility of the warming device.

Materials of the air impermeable sheet 6 include those of the air impermeable sheet used in the warming device of the first embodiment.

The surfacing members 50 and 60 are not particularly limited as long they have an agreeable hand and flexibility. The thickness of the surfacing members is preferably 0.1 to 2.0 mm, more preferably 0.2 to 1.0 mm. The surfacing members having a thickness within the recited range relax the heat of the heat generating element to give a mild warm feel.

The basis weight of the surfacing members 50 and 60 preferably ranges from 5.0 to 200 g/m$^2$, more preferably 10 to 100 g/m$^2$. The surfacing member weighing 5.0 g/m$^2$ or more is preferred for strength and tearproofness. The surfacing member weighing 200 g/m$^2$ or less feels good to the touch and sufficiently acts as a heat insulator, which is preferred for heat conduction.

The surfacing members 50 and 60 can be made of nonwoven fabrics of synthetic fibers, such as polyolefin (e.g., polyethylene or polypropylene), polyester, polyamide, polyurethane, polystyrene, ethylene-vinyl acetate copolymers, and polyethylene terephthalate, plant fibers, such as cotton and hemp, animal fibers, such as wool and silk, regenerated fibers, such as rayon and cuprammonium rayon, or semi-synthetic fibers, such as cellulose acetate; paper inclusive of Japan paper and synthetic paper; woven fabrics (e.g., woolen fabric); leather; and the like. A plurality of the surfacing members 50 or 60 may be used as stacked.

The method of producing the heat generating molded article 10 will then be described.

The heat generating sheet precursor 2 used in the production of the heat generating molded article 10 is preferably prepared by papermaking process in the same manner as described with respect to the warming device of the first embodiment using a raw material composition (slurry) containing the oxidizable metal, moisture retaining agent, fibrous material, and water.

The air permeable sheet 5, the air impermeable sheet 6, and the surfacing members 50 and 60 are superposed on the dried heat generating sheet precursor 2 to build up the above-described multilayer structure, which is embossed through the nip of matched steel embossing rollers to make the depressions 11 and the projections 12. The unity of the resulting multilayer structure may be improved by providing a layer of a thermoplastic resin or a component developing adhesiveness on being dried between the heat generating sheet and the air permeable sheet or the air impermeable sheet.

The electrolyte is then incorporated into the heat generating sheet precursor 2 in the same manner as in the production of the warming device of the first embodiment.

After incorporating the electrolyte into the heat generating sheet precursor, the water content of the heat generating sheet can be adjusted, when needed, to provide a stabilized heat generating molded article 10. If desired, the heat generating molded article thus prepared can be fabricated by trimming into a prescribed size. The resulting heat generating molded article 10 is supplied as individually packaged in an oxygen impermeable packaging material.

As described, the heat generating molded article 10 of the fourth embodiment is composed of the heat generating sheet 2 having the above-described composition and the specific breaking length and the air permeable sheet 5 and the air impermeable sheet 6 superposed on the respective sides of the sheet 2 and has a large number of projections and depressions formed on both sides thereof by embossing. Therefore, the heat generating molded article 10 shows high heat generating performance immediately after the start of use and has excellent flexibility. Moreover, fall-off of the constituent materials from the molded article 10 is prevented.

Figure 6:
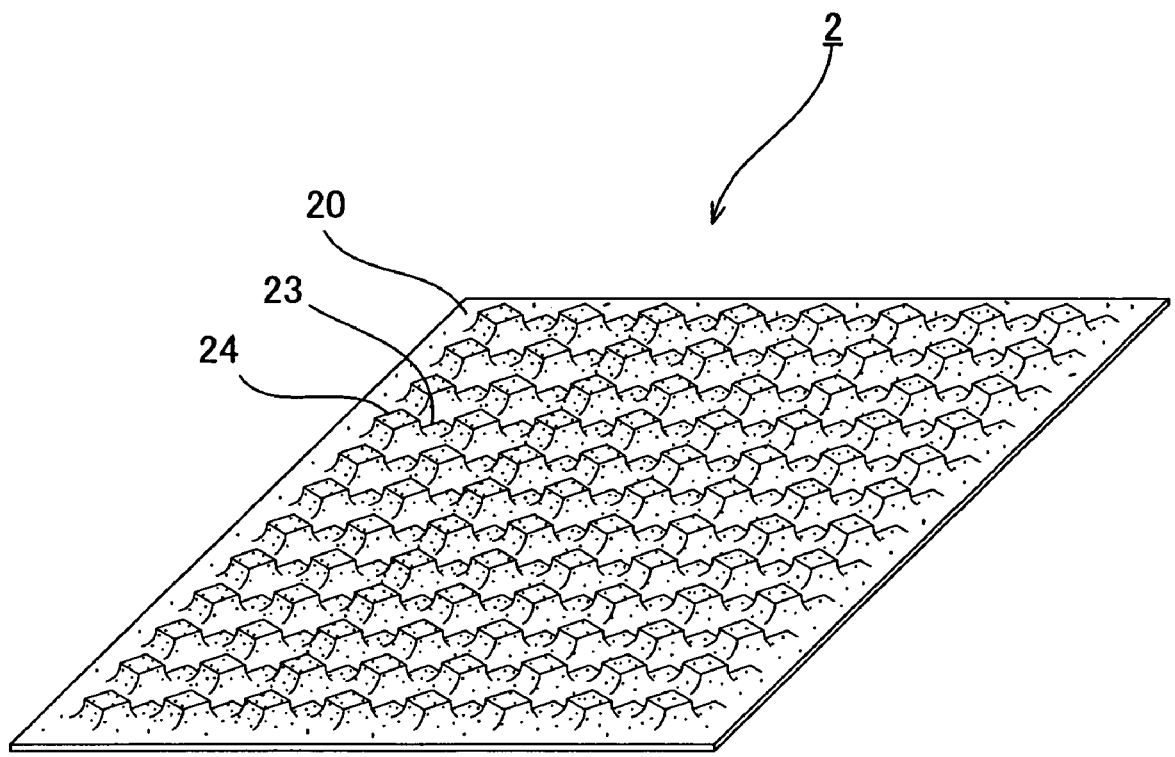
FIG. 6 is a schematic perspective view of an embodiment of the heat generating sheet according to the present invention.
Figure 7A:
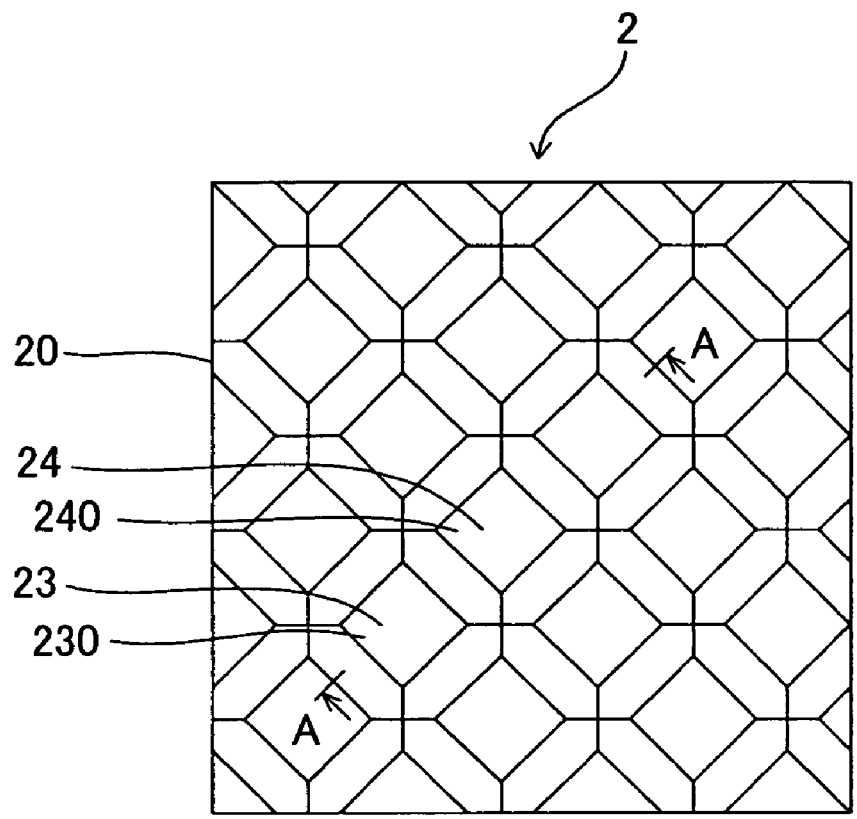
FIG. 7($a$) is an enlarged plan view of a part of the heat generating sheet shown in FIG. 6.
Figure 7B:
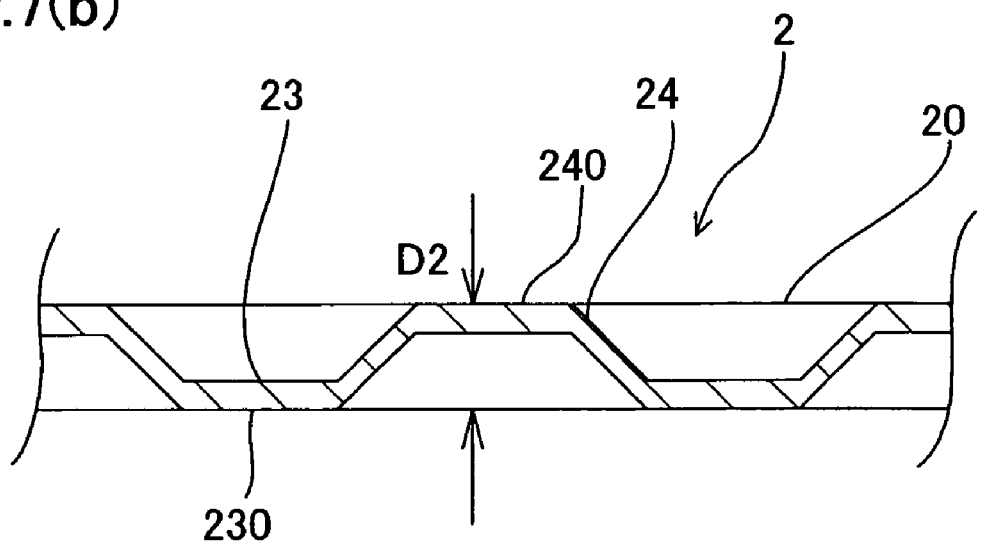

FIGS. 6, 7(*a*), and 7(*b*) show an embodiment of the heat generating sheet according to the present invention as a fifth embodiment of the present invention. Numeral 2 indicates a heat generating sheet. Elements in these figures common to the warming device 1 of the first embodiment are given the same numerals. The description about the first embodiment applies as appropriate to the elements of the fifth embodiment that are not described hereunder.

As illustrated in FIGS. 6, 7(*a*), and 7(*b*), the heat generating sheet 2 is a molded article (i.e., a molded article of sheet form) 20 containing an oxidizable metal, a moisture retaining agent, and a fibrous material and having a large number of depressions 23 and projections 24 embossed on both sides thereof by means of matched steel embossing rolls. In this particular embodiment, the bottom 230 of the depression 23 and the top 240 of the projection 24 are both square-shaped and arranged in a diamond lattice pattern.

The level difference between the projections and the depressions is preferably 0.3 to 5 mm, more preferably 0.5 to 2 mm. With this difference, heat generating properties of the resulting heat generating sheet and shapability by embossing are secured. The level difference between the projections and the depressions is obtained from a distance D2 between the bottom 230 of the depressions 23 and the top 240 of the projection 24.

The bottom 230 of the individual depressions 23 and the top 240 of the individual projections 24 each preferably have an area of 0.01 to 100 mm$^2$, more preferably 0.1 to 25 mm$^2$. With this area, when two or more heat generating sheets are used as stacked, the stack can be united and prevented from sliding.

The number of the bottoms 230 of the depressions 23 and the tops 240 of the projections 24 in an area of 100 cm$^2$ of the heat generating sheet 2 is preferably 1 to 10000, more preferably 10 to 8000. With that number of the bottoms 230 and the tops 240, when two or more heat generating sheets are used as stacked, the stack can be united and prevented from sliding.

The oxidizable metal used in the molded article 20 can be of any kind that is commonly employed in this type of heat generating molded articles. The oxidizable metal is preferably in the form of powder or fiber from the standpoint of ease in handling, molding capabilities, and the like.

Oxidizable metals in the form of powder include the particulate oxidizable substances listed above with reference to the warming device of the first embodiment.

Oxidizable metals in the form of fiber include the fibrous oxidizable substances recited with reference to the warming device of the first embodiment.

The proportion of the oxidizable metal in the molded article 20 is preferably 10% to 95% by weight, more preferably 30% to 80% by weight. Where the proportion of the oxidizable metal is 10% by weight or more, the following advantages are offered. The resulting heat generating sheet 2 sufficiently heats up to a degree feeling hot to the touch of fingers. Since the proportions of the fibrous material and a binding component hereinafter described, which constitute the molded sheet 2, are controlled, flexibility of the sheet can be maintained. Where the proportion is 95% by weight or less, the heat generating sheet 2 has sufficient air permeability, so that the reaction takes place sufficiently in the inside of the sheet to sufficiently raise the temperature. The duration of heat generation is sufficient. a water vapor supply by the moisture retaining agent is secured. Fall-off of the oxidizable metal hardly occurs. The molded sheet contains certain proportions of the fibrous material and binding component hereinafter described, which make up the molded article 20, to secure mechanical strength characteristics such as flexural strength and tensile strength. The oxidizable metal content in the molded article 20 can be determined by determination of ash in accordance with JIS P8128. Vibrating sample magnetization measurement is useful in the case of iron, of which the magnetization on applying an external magnetic field is made use of.

The moisture retaining agent includes any moisture retaining agents commonly employed in heat generating molded articles with no particular limitation. The moisture retaining agent not only serves for a water vapor retention but functions as an agent for holding and supplying oxygen to the oxidizable metal. Examples of useful moisture retaining agents include those recited with respect to the warming device of the first embodiment.

The proportion of the moisture retaining agent in the molded article 20 is preferably 0.5% to 60% by weight, more preferably 1% to 50% by weight. With a moisture retaining agent content of 0.5% by weight or more, the heat generating sheet 2 holds a requisite water content for sustaining the oxidation reaction of the moisture retaining agent for maintaining the temperature at or above the body temperature. Furthermore, the heat generating sheet has sufficient air permeability for oxygen supply to assure high heat generation efficiency. With the moisture retaining agent content being 60% by weight or less, the following advantages are offered. The heat generating sheet 2 has a controlled heat capacity for the amount of heat generated to show a sufficient temperature rise to a degree that feels warm to the touch. Fall-off of the moisture retaining agent is suppressed. Sufficient amounts of the fibrous material and binding component hereinafter described, which constitute the molded article 20, are secured to provide sufficient mechanical strength such as flexural strength and tensile strength.

The fibrous material includes those enumerated for the warming device of the first embodiment.

The fibrous material content in the molded article 20 is preferably 2% to 50% by weight, more preferably 5% to 40% by weight. With the fibrous material content of 2% by weight or more, fall-off of the oxidizable metal and the moisture retaining agent is sufficiently prevented, and the resulting molded article has sufficient strength. With the fibrous material content of 50% by weight or less, the heat generating molded article has controlled heat generation to show a sufficient temperature rise. Furthermore, heat capacity of in the heat generating sheet 2 are secured to develop sufficient heat generating performance as desired.

A flocculant is preferably incorporated into the molded article 20 as described infra.

If desired, the molded article 20 may contain additives commonly used in papermaking, such as sizes, colorants, strengthening agents, yield improvers, loading materials, thickeners, pH control agents, and bulking agents, with no particular limitation. The amounts of the additives to be added can be selected appropriately according to the kinds.

The molded article 20 preferably contains at least 50% by weight, more preferably 70% by weight or more, even more preferably 80% by weight or more, of components other than the fibrous material. When the content of the components other than the fibrous material is 50% by weight or more, the temperature of heat generation rises to or above the temperature that feels hot when touched with the fingers, and the like. The higher the content of the components other than the fibrous material, the more preferred. Nevertheless, the upper limit is preferably about 98% by weight for assuring strength necessary to maintain fabricability of the molded article 20. The proportions of the components other than the fibrous material are determined in the same manner as described with respect to the warming device of the third embodiment.

The heat generating sheet 2 contains an electrolyte in the molded article 20.

Any kind of electrolytes commonly employed in this type of heat generating molded articles can be used with no particular restrictions. Examples of useful electrolytes include those recited for the warming device of the first embodiment.

The molded article used in the heat generating sheet 2 has a breaking length of 100 to 4000 m, preferably 200 to 3000 m. With a breaking length of 100 m or longer, the molded article of sheet form is formed in a stable manner; the resulting molded article can be embossed in a stable manner without being broken or cut; and the final product has sufficient strength for good usability. A molded article 20 with a breaking length of 4000 m or less contains moderately controlled amounts of the fibrous material and the binding component, which constitute the molded article 20, and therefore, the resulting heat generating sheet 2 has sufficient flexibility and heat generating performance.

The thickness of the molded article 20 used in the heat generating sheet 2 is preferably 0.08 to 1.2 mm, more preferably 0.1 to 0.6 mm. A thickness of 0.08 mm or greater provides the following advantages. Sufficient mechanical strength is secured. Sufficient fixing ratios of the oxidizable metal, the moisture retaining agent, etc. are achieved. Uniformity (stability) in thickness and composition is obtained. A break of the sheet due to pinhole development, which leads to poor productivity and poor fabricability, hardly occurs. The resulting heat generating sheet 2 exhibits satisfactory heat generating properties. A thickness of 1.2 mm or smaller offers the following advantages. The heat generating sheet 2 maintains folding strength and hardly undergoes brittle fracture. When applied to a bending part of a body, such as an elbow, a knee, and the face, etc., the heat generating sheet 2 has good conformability. The molded article has excellent productivity in terms of papermaking time and drying time. The molded article has excellent fabricability, hardly undergoing reduction of heat generating performance, breaking, cracking, or the like.

The electrolyte is preferably used in an amount of 0.5% to 30% by weight, more preferably 1% to 25% by weight, based on the water content of the heat generating sheet 2. At the electrolyte content of 0.5% by weight or more, the oxidation reaction proceeds sufficiently in the resulting heat generating sheet 2, and the water content of the heat generating sheet 2 necessary to maintain the requisite amount of the electrolyte for heat generation can be held down. As a result, reduction in temperature rise due to an increase in water content of the heat generating sheet is avoided. At the electrolyte content of 30% by weight or less, precipitation of the electrolyte hardly occurs, and the heat generating sheet 2 maintains satisfactory air permeability. A certain proportion of water is held in the heat generating sheet 2 for securing a necessary amount of the electrolyte for heat generation. A sufficient amount of water is supplied to the oxidizable metal, etc. to assure high heat generating performance. The electrolyte of that amount can uniformly be distributed throughout the heat generating sheet 2.

The water content of the heat generating sheet 2 is preferably 10% to 80% (by weight, hereinafter the same), more preferably 20% to 60%. With a water content of 10% or more, a water vapor necessary for continuing oxidation reaction is secured, and a water vapor can be distributed uniformly throughout the heat generating sheet 2, leading to uniform heat generation. With a water content of 80% or less, the heat generating sheet 2 has a controlled heat capacity for the amount of heat generated, which assures a sufficient rise in temperature. Besides, the air permeability of the heat generating sheet 2 is sufficient so that high heat generating performance and sufficient shape retention and mechanical strength are secured.

The basis weight of the heat generating sheet 1 is preferably 10 to 1000 g/m$^2$, more preferably 50 to 600 g/m$^2$. Even in using, for example, an oxidizable metal having a high specific gravity, a sheet having a basis weight of 10 g/m$^2$ or more can be formed stably. A basis weight of 1000 g/m$^2$ or less provides comfort of use and is also preferred from the standpoint of productivity, perationality and the like.

The temperature reached by the heat generating sheet 2 on heat generation is preferably 30° to 100° C., more preferably 35° to 90° C. The temperature reachable by the heat generating sheet 2 can freely be designed by the formulation of the components according to the purpose, that is, whether a steep temperature rise is needed or a long duration of heat generation at a relatively low temperature is desired, and the like.

It is desirable for the heat generating sheet 2 to generate 0.1 to 100 mg/(cm$^2$·10 min), more preferably 1 to 50 mg/(cm$^2$·10 min), of water vapor per unit area for 10 minutes.

Similarly to the time required for reaching the maximum temperature of heat generation, the amount of water vapor produced by the heat generating sheet 2 can be freely designed by the formulation of the components according to the purpose, that is, whether a steep temperature rise is desired or a long duration of heat generation at a relatively low temperature is desired, and the like.

The method of producing the heat generating sheet 2 will then be described.

The molded article of sheet form that can be used in the heat generating sheet 2 is preferably prepared by papermaking process using a raw material composition (slurry) containing the oxidizable metal, moisture retaining agent, fibrous material, and water and forming the molded sheet in the same manner as described with respect to the warming device of the first embodiment.

Shaping of the molded article (i.e., dewatering and drying) is preferably conducted in an inert gas atmosphere. Nevertheless, because the molded article is free from an electrolyte acting as an oxidation promoter as previously stated, the shaping may be performed in an ordinary air atmosphere if desired, which enables simplification of equipment. Thin and yet tearproof, the resulting molded article can be taken up in a roll where needed.

The dried molded article 20 is embossed through the nip of matched steel embossing rollers to make the depressions 23 and the projections 24.

Where necessary, the embossed molded article 20 is subjected to fabrication processings such as craping, slitting, trimming or any other processings for conversion. The embossed molded article or a stack of the embossed molded articles, either alone or as laminated with other film or sheet (e.g., paper, woven fabric, nonwoven fabric or plastic film), may be pressed or needle-punched to be united into a unitary sheet or perforated. A thermoplastic resin component or a hot-water-soluble component may be incorporated into the raw material composition to facilitate heat sealing for lamination or other processings.

The electrolyte is then incorporated into the embossed molded article 20. The step of incorporating the electrolyte may be carried out in an ordinary air atmosphere but is preferably done in an inert gas atmosphere such as nitrogen or argon.

The electrolyte can be incorporated into the molded article in the same manner as in the fourth embodiment described above.

After the electrolyte is incorporated into the molded article, the water content may be adjusted to provide a stabilized heat generating sheet 2 when needed. If desired, the heat generating sheet thus prepared can be fabricated into a desired size by trimming, stacking one on top of another, and the like. The resulting heat generating sheet 2 is supplied as individually packaged in an oxygen impermeable packaging material.

As described, since the heat generating sheet 2 of the fifth embodiment has a large number of projections and depressions formed on both sides thereof, it shows high heat generating performance immediately after the start of use. When two or more heat generating sheets 2 are used as stacked, they hardly slide on each other. Owing to the numerous projections and depressions, the heat generating sheet 2 has good flexibility.

Figure 8:
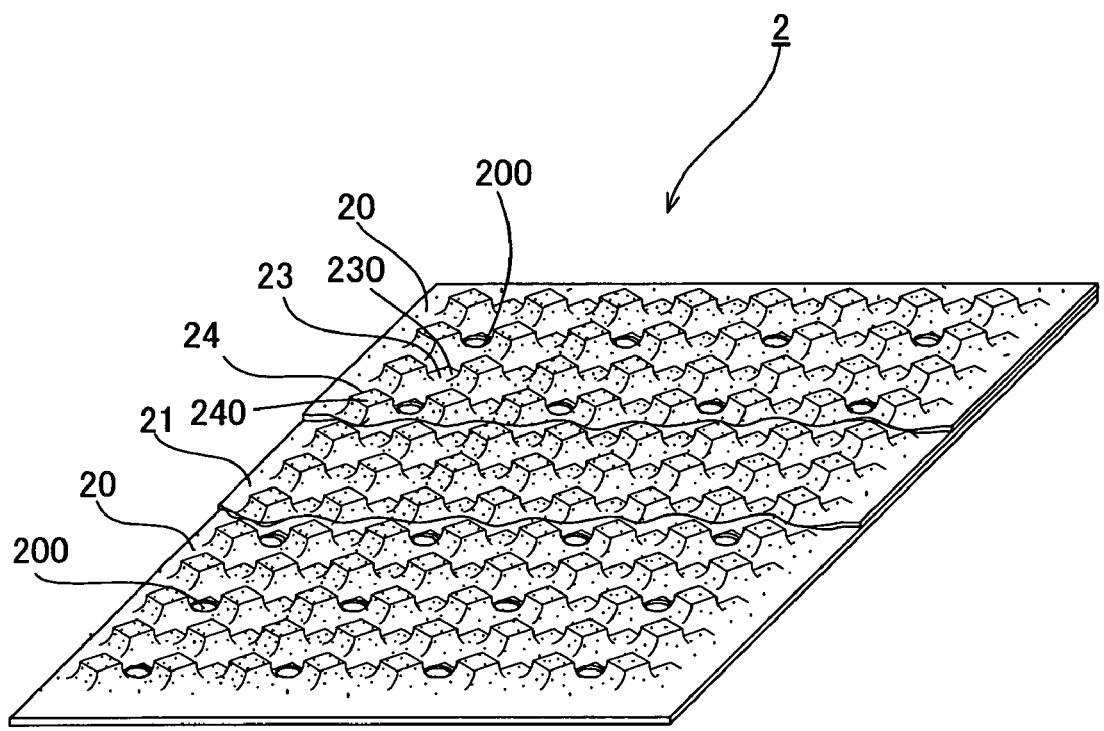
FIG. 8 is a schematic perspective view of an embodiment of the heat generating sheet according to the present invention.
Figure 9A:
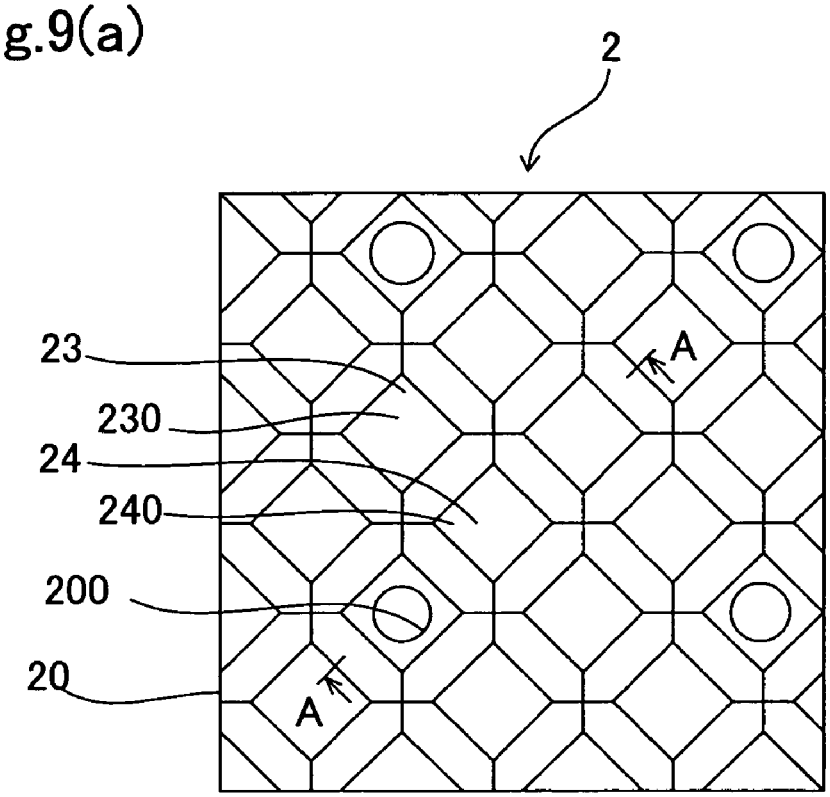
FIG. 9($a$) is an enlarged plan view of a part of the heat generating sheet shown in FIG. 8.
Figure 9B:
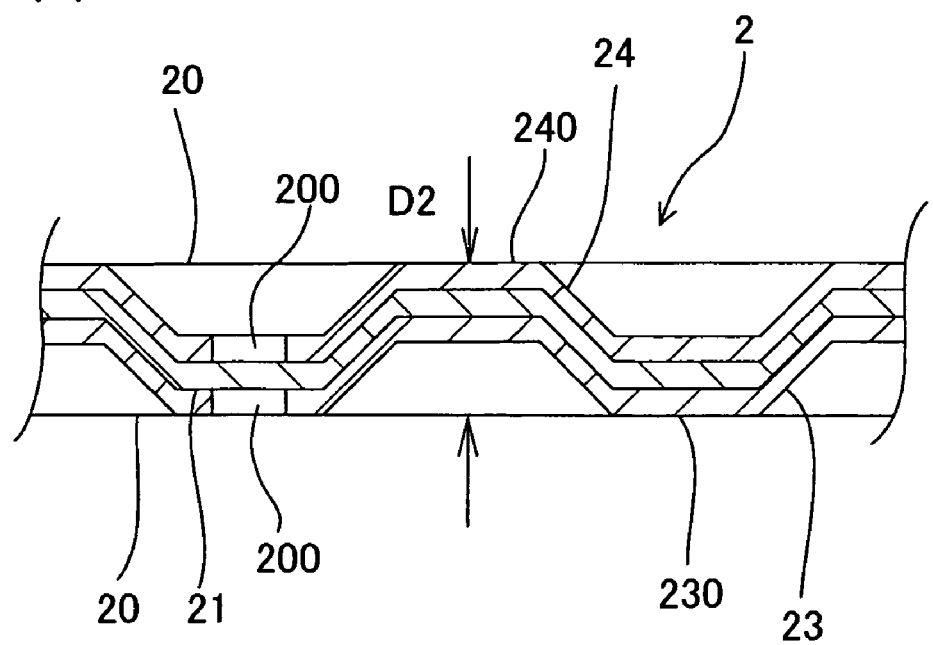

FIGS. 8, 9(a), and 9(b) show another embodiment of the heat generating sheet according to the present invention. Numeral 2 indicates a heat generating sheet. Elements in these figures common to the warming device 1 of the first embodiment and the heat generating sheet 2 of the fifth embodiment are given the same numerals. The description about the first and the fifth embodiments applies as appropriate to the elements of this embodiment that are not described hereunder.

As illustrated in FIGS. 8, 9(a), and 9(b), the heat generating sheet 2 has a first molded article 20 containing an oxidizable metal, a moisture retaining agent, and a fibrous material and having many holes 200 and a second molded article 21 containing an oxidizable metal, a moisture retaining agent, and a fibrous material and having no holes 200. The molded article 21 is superposed on each side of the molded article 20.

The individual holes 200 preferably have an area of 0.01 to 10 $mm^2$, more preferably 0.1 to 8 $mm^2$. With the holes having an area of 0.01 $mm^2$ or more, air is sufficiently allowed to pass so that the heat generating performance is offered to the full. With the holes having an area of 10 $mm^2$ or less, non-uniformity of temperature or the like due to the holes where no heat is generated is ignorable.

The number of the holes 200 made in the molded article 20 is preferably 0.1 to 20, more preferably 1 to 15, per square centimeter. The number of the holes being 0.1/$cm^2$ or greater, air is sufficiently allowed to pass, so that the heat generating sheet offers the full performance. With the number of the holes being 20/$cm^2$ or fewer, the strength of the heat generating sheet is secured. The number of the holes falling within the recited range, when holes are made through a stack of two or more molded articles 20, the molded articles 20 are joined together with high unity and prevented from sliding.

The heat generating sheet 2 has a large number of depressions 23 and projections 24 embossed on both sides thereof by means of matched steel embossing rolls. In this particular embodiment, the bottom 230 of the depression 23 and the top 240 of the projection 24 are both square-shaped and arranged in a diamond lattice pattern.

The level difference between the projections and the depressions is preferably 0.3 to 5.0 mm, more preferably 0.5 to 2.0 mm. With this difference, heat generating properties of the resulting heat generating sheet and shapability by embossing are secured. The level difference between the projections and the depressions is obtained from a distance D2 between the bottom 230 of the depressions 23 and the top 240 of the projection 24.

The bottom 230 of the individual depressions 23 and the top 240 of the individual projections 24 each preferably have an area of 0.01 to 100 $mm^2$, more preferably 0.1 to 25 $mm^2$. With this area, the heat generation characteristics are improved and, when two or more heat generating sheets are stacked one on top of another, the stack can be united and prevented from sliding.

The number of the bottoms 230 of the depressions 23 and the tops 240 of the projections 24 in an area of 100 $cm^2$ of the heat generating sheet 2 is preferably 1 to 10000, more preferably 10 to 8000. With that number of the bottoms 230 and the tops 240, the heat generation characteristics are improved, and when two or more heat generating sheets are stacked up, the stack can be united and prevented from sliding.

The heat generating sheet 2 preferably has an air permeance of 0.1 to 8 s/(6.4 $cm^2$·300 ml), more preferably 0.5 to 6 s/(6.4 $cm^2$·300 ml), per 100 $g/m^2$. Within that range of air permeance, the heat generating sheet 2 exhibits improved heat generation characteristics. Furthermore, when an electrolyte solution is incorporated as described later, the electrolyte solution can penetrate more uniformly. The term "air permeance" as used herein means a value measured in accordance with JIS P8117.

The basis weight of the heat generating sheet 2 is preferably 10 to 1000 $g/m^2$, more preferably 50 to 600 $g/m^2$. Even in using, for example, an oxidizable metal having a high specific gravity, a sheet having a basis weight of 10 $g/m^2$ or more can be formed stably. A sheet weighing 1000 $g/m^2$ or less feels good while worn and is also preferred from the standpoint of productivity, operationality, and the like.

The temperature reached by the heat generating sheet 2 on heat generation is preferably 30° to 100° C., more preferably 35° to 90° C.

It is desirable for the heat generating sheet 2 to generate 0.1 to 100 mg/($cm^2$·10 min), more preferably 1 to 50 mg/($cm^2$·10 min), of water vapor per unit area for 10 minutes. Similarly to the time required for reaching the maximum temperature of heat generation, the amount of water vapor produced by the heat generating sheet 2 can be freely designed by the formulation of the components according to the purpose, that is, whether a steep temperature rise is desired or a long duration of heat generation at a relatively low temperature is desired, and the like.

The oxidizable metal used in the molded articles 20 and 21 constituting the heat generating sheet 2 can be of any kind that is commonly employed in this type of heat generating molded articles. The oxidizable metal is preferably in the form of powder or fiber from the standpoint of ease in handling, molding properties and the like.

Oxidizable metals in the form of powder include the oxidizable substances recited with reference to the warming device of the first embodiment.

The proportion of the oxidizable metal in the molded articles 20 and 21 is preferably 10% to 95% by weight, more preferably 30% to 80% by weight. Where the proportion of the oxidizable metal is 10% by weight or more, the resulting heat generating sheet 21 sufficiently heats up to or above the temperature feeling hot to the touch of fingers and the like, and the molded articles 20 and 21 are flexible because of the controlled proportions of the fibrous material and a binding component hereinafter described, which constitute the molded articles 20 and 21. With the proportion being 95% by weight or less, the heat generating sheet 2 has sufficient air permeability. As a result, the reaction takes place sufficiently in the inside of the sheet to sufficiently raise the temperature. The duration of heat generation is sufficient. a water vapor supply by the moisture retaining agent is secured. Fall-off of the oxidizable metal hardly occurs. Certain proportions of the fibrous material and a binding component (e.g., a flocculant), which make up the molded articles 20 and 21, are secured to assure sufficient mechanical strength such as flexural strength and tensile strength.

The moisture retaining agent includes any moisture retaining agents commonly employed in heat generating molded articles with no particular limitation. The moisture retaining agent not only serves for a water vapor retention but functions as an agent for holding and supplying oxygen to the oxidizable metal. Examples of useful a water vapor retaining agents include those recited with respect to the warming device of the first embodiment.

The proportion of the moisture retaining agent in the molded articles 20 and 21 is preferably 0.5% to 60% by weight, more preferably 1% to 50% by weight. With a moisture retaining agent content of 0.5% by weight or more, the heat generating sheet 2 holds a requisite water content for the oxidizable metal to sustain oxidation reaction for maintaining the temperature at or above the body temperature. Furthermore, the heat generating sheet has sufficient air permeability for oxygen supply to assure high heat generation efficiency. With the moisture retaining agent content being 60% by weight or less, the following advantages are offered. The heat generating sheet 2 has a controlled heat capacity for the amount of heat generated to show a sufficient temperature rise to a degree that feels warm. The moisture retaining agent hardly falls off. Sufficient amounts of the fibrous material and binding component, which build up the molded articles 20 and 21, are secured to provide sufficient mechanical strength such as flexural strength and tensile strength.

The fibrous material includes those enumerated for the warming device of the first embodiment.

The fibrous material content in the molded articles 20 and 21 is preferably 2% to 50% by weight, more preferably 5 to 40% by weight. With the fibrous material content of 2% by weight or more, fall-off of the oxidizable metal and the moisture retaining agent is sufficiently prevented, and the resulting molded articles have sufficient strength. With the fibrous material content of 50% by weight or less, the heat generating sheet has a controlled heat capacity for the amount of generated heat to show a sufficient temperature rise. Furthermore, certain proportions of the oxidizable metal and the moisture retaining agent are secured to develop sufficient heat generating performance as desired.

The molded articles 20 and 21 each preferably contain at least 50% by weight, more preferably 70% by weight or more, even more preferably 80% by weight or more, of components other than the fibrous material. When the content of the components other than the fibrous material is 50% by weight or more, the heat generating sheet sufficiently heats up to or above the temperature feeling hot by the finger or the like. The higher the content of the components other than the fibrous material, the more preferred. Nevertheless, the upper limit is about 98% by weight for assuring strength necessary to maintain fabricability of the molded articles 20 and 21.

The molded articles 20 and 21 may have the same or different compositions.

The molded article 20 with holes 200 preferably has an air permeance of 0.1 to 8 s/(6.4 cm$^2$·300 ml), more preferably 0.5 to 5 s/(6.4 cm$^2$·300 ml). Within that range of air permeance, improved heat generation characteristics are obtained. Furthermore, when an electrolyte solution is incorporated, the solution can penetrate more uniformly.

It is preferred for the molded article 20 before being perforated and the molded article 21 to have a breaking length of 100 to 4000 m, more preferably 200 to 3000 m. With a breaking length of 100 m or longer, the molded articles can be formed stably and embossed stably without being broken or cut, and the final product has moderate strength and excellent usability. The molded articles with a breaking length of 4000 m or less contain moderately controlled amounts of the fibrous material and the binding component. As a result, the resulting heat generating sheet 2 has sufficient flexibility and sufficient heat generating performance.

The molded article 20 before being perforated and the molded article 21 each preferably have a basis weight of 10 to 1000 g/m$^2$, more preferably 50 to 600 g/m$^2$. Even in using, for example, an oxidizable metal and etc. having a high specific gravity, molded articles having a basis weight of 10 g/m$^2$ or more can be formed stably. Molded article weighing 1000 g/m$^2$ or less are comfortable to use and also advantageous for productivity and operationality.

Each of the molded articles 20 and 21 preferably has a thickness of 0.08 to 1.2 mm, more preferably 0.1 to 0.6 mm. Molded articles with a thickness of 0.08 mm or more exhibit high mechanical strength, sufficient fixation of the oxidizable metal, the moisture retaining agent, etc., and uniformity (stability) in thickness and composition. A break of the sheet like due to pinhole development and the like, which leads to poor productivity and poor fabricability, hardly occurs. The resulting heat generating sheet 2 exhibits satisfactory heat generating properties. A sheet thickness of 1.2 mm or less offers the following advantages. The molded articles have enough folding strength not to undergo brittle fracture easily. The heat generating sheet is conformable when applied to a bending part of a body, such as an elbow, a knee, and the face, etc. High operationality is enjoyed in terms of papermaking and drying time. Reduction in heat generating performance hardly occurs. The molded articles have excellent fabricability, hardly undergoing breaking or cracking during fabrication processing.

It is preferred for the molded articles 20 and 21 to contain an electrolyte.

Any kind of electrolytes commonly used in this type of heat generating molded articles can be used. Examples of useful electrolytes include those recited for the warming device of the first embodiment.

The electrolyte is preferably added in an amount of 0.5% to 30% by weight, more preferably 1% to 25% by weight, based on the water content of the molded articles 20 and 21. At the electrolyte content of 0.5% by weight or more, the oxidation reaction proceeds sufficiently in the resulting heat generating sheet 2, and the water content of the molded articles 20 and 21 necessary to maintain the requisite amount of the electrolyte for heat generation is held down. As a result, reduction in temperature rise of the heat generating sheet 2 due to an increased water content is avoided. At the electrolyte content of 30% by weight or less, precipitation of the electrolyte hardly occurs, and the heat generating sheet 2 maintains satisfactory air permeability. A certain proportion of water is held in the heat generating sheet 2 for securing a necessary amount of the electrolyte for heat generation. A sufficient amount of water is supplied to the oxidizable metal, etc. to assure high heat generating performance. The electrolyte of that amount can uniformly be distributed throughout the molded articles 20 and 21.

The water content of each of the molded articles 20 and 21 is preferably 10% to 80% (by weight, hereinafter the same), more preferably 20% to 60%. With a water content of 10% or more, a water vapor necessary for continuing oxidation reaction is secured. Water is uniformly supplied throughout the heat generating sheet 2, leading to uniform heat generation. With a water content of 80% or less, the heat generating sheet 2 has a controlled heat capacity for the amount of heat generated to achieve a sufficient rise in temperature. Moreover, the air permeability of the heat generating sheet 2 is sufficient to secure high heat generating performance. The heat generating sheet 2 has sufficient shape retention and mechanical strength.

The temperature reached by the molded articles 20 and 21 on heat generation is preferably 30° to 100° C., more preferably 35° to 90° C. The temperature reachable by the molded sheets 20 and 21 can freely be decided according to the desired temperature to be reached by the heat generating sheet 2.

It is desirable for the molded articles 20 and 21 to generate 0.1 to 100 mg/(cm$^2$·10 min), more preferably 1 to 50 mg/(cm$^2$·10 min), of water vapor. The amount of water vapor to be generated by the molded articles 20 and 21 is freely decided according to the desired amount of water vapor to be generated by the heat generating sheet 2.

The method of producing the heat generating sheet 2 will then be described.

First of all, a raw material composition (slurry) containing the oxidizable metal, moisture retaining agent, fibrous material, and water is prepared, and the molded article 20 with no holes 200 and the molded article 21 are formed by papermaking using the slurry in the same manner as for the heat generating sheet precursor used to make the heat generating sheet of the fifth embodiment.

After drying, holes 200 are made in the molded article 20 with no holes. The method of making the holes 200 is not limited. The method of making the holes 200 includes needle punching and etc.

The molded articles 20 and 21 are stacked to give the above-described layer structure and embossed through the nip of matched steel embossing rollers to make the depressions 23 and the projections 24.

Where necessary, the molded article 20 with no holes 200 and the molded article 21 may be subjected to fabrication processings such as craping, trimming or any other processings for conversion. The molded article or a plurality of the molded articles, either alone or as laminated with other film or sheet (e.g., paper, woven fabric, nonwoven fabric or plastic film), may be pressed or embossed to be united into a unitary sheet or given an uneven pattern. In order to facilitate heat sealing for lamination or other processing, a thermoplastic resin component or a hot-water-soluble component may be incorporated into the raw material composition.

After the molded sheets 20 and 21 are stacked, the electrolyte is incorporated into the stack. The step of incorporating the electrolyte is carried out in the same manner as in the production of the warming device of the first embodiment.

After the addition of the electrolyte, the water content can be adjusted, if necessary, to provide a stabilized heat generating sheet 2. If desired, the heat generating sheet thus prepared can be fabricated into a prescribed size by trimming, stacking, and the like. The resulting heat generating sheet 2 is supplied as individually packaged in an oxygen impermeable packaging material. The heat generating sheet 2 is used as held in a holder, such as a bag, having air permeability.

As described, since the heat generating sheet 2 of the present embodiment is composed of the molded article 21 and the molded article 20 having a large number of holes 200 laminated on both sides of the molded article 21, it shows high heat generating performance for its small thickness. The many holes 200 formed in the molded articles 20 contribute to excellent flexibility.

The present invention is not limited to the foregoing embodiments, and alterations and modifications can appropriately be made thereto without departing from the spirit and scope of the present invention.

Although the warming device of sheet form of the present invention preferably has an electrolyte solution previously incorporated into the heat generating sheet 2 as in the warming device 1 of the first embodiment, it is possible that a warming device containing no electrolyte solution in its heat generating sheet is once prepared, which is impregnated with an electrolyte solution upon use. In such a case, there is no need to carry out production of the warming device in an oxygen-free or low-oxygen atmosphere, which enables simplification of the production steps and equipment.

The shape of the warming device of the present invention may be altered to suit the application. For example, the warming device may have the shape of a band that can be wrapped around a part of a body or an object to be treated or may be made into a cloth-like material that can be applied to the surface of a body or an object to be treated.

The layered structure of the heat generating sheet and the holder which constitute the warming device of the present invention can be altered to suit the intended use. For instance, the surfacing member(s) disposed on the surface of the warming device may be omitted.

While application of the warming device according to the present invention is not limited, it is suited for use as disposable bedding including comforters, blankets, and covers therefor; disposable mats or sheets including, cushions, ground sheets, and pet sheets; and disposable horticultural sheets including frost-preventive sheets for bonsai and other plants.

The layered structure of the heat generating sheet and the holder which constitute the warming device of the present invention can be altered to suit the intended use. For instance, the layer structure of the third embodiment, in which the warming device has air permeability on only one side thereof so that steam may be released only from that side, may be modified such that the holder is made of two air permeable sheets joined together so that steam may be released from both sides of the heat generating sheet.

While in the foregoing embodiments the air permeable sheet and the air impermeable sheet are joined by heat sealing, these sheets may be joined by other means, such as an adhesive.

Applications of the warming device of the present invention are not particularly limited. In addition to the applications described with reference to the third embodiment, the warming device of the present invention can be combined with various functional preparations for, for example, cleaning, sterilization, slow wax release, scenting or deodorization to provide a hot sheet suited for use in home care applications (cleaning or treatment of flooring, tatami, kitchen stoves and fans, etc.), air care applications for creating a comfortable space; car care applications (cleaning and waxing); facial and body skin care applications (cleansing, sanitization, moisturizing, and make-up removal); bedding including comforters, blankets, and covers thereof; and mats and sheets, such as cushions and ground sheets, etc.

Figure 10:
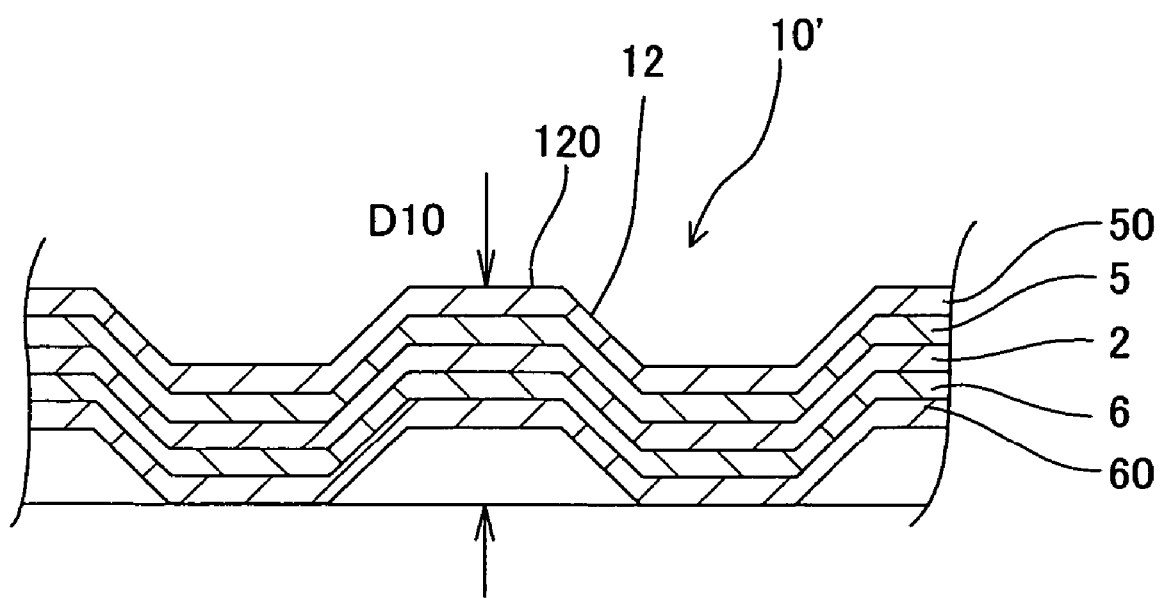
FIG. 10 is a schematic fragmentary cross-sectional view of another embodiment of the present invention (corresponding to FIG. 5($b$)).

The heat generating molded article 10 according to the forth embodiment (see FIGS. 4, 5(a), and 5(b)) is obtained by embossing the heat generating sheet precursor from both sides thereof by passing the precursor between matched steel embossing rolls. In a modification, the precursor may be embossed from only one side thereof by passing the precursor between an engraved roll and a flat roll to give the heat generating molded article 10' shown in FIG. 10. In this modification, the level difference D10 between the projections and the depressions is preferably 0.3 to 5 mm, more preferably 0.5 to 4 mm. With such a level difference, when the heat generating sheet precursors are stacked one on top of another, they can be joined into a unitary sheet and prevented from sliding. The top 120 of each projection 12 (or the bottom of each depression) formed by embossing between the engraved roll and the flat roll preferably has an area of 0.01 to 100 mm$^2$, more preferably 0.1 to 25 mm$^2$, for the same reasons as stated with respect to the heat generating molded article 10. The number of the tops 120 of the projections 12 (or the bottom of each depression) in an area of 10 cm$^2$ of the heat generating molded article is preferably 1 to 10000, more preferably 10 to 8000, for the same reason as for the heat generating molded article 10.

The shape of the bottoms and the tops formed on the heat generating sheet precursor by the embossing is not limited to the shape adopted in the foregoing embodiments and includes a rectangle, a polygon, a circle, an ellipse, and an elongated ellipse. The bottoms and the tops are preferably flat but may be curved. Furthermore, the cross-sectional contour of the projections and the depressions is not limited and includes a trapezoid (as in the above-mentioned embodiments), a triangle, a rectangle, a semicircle, a semi-ellipse, a half elongated ellipse, and a bell shape.

The heat generating molded article of the present invention preferably has the air permeable sheet 5 on one side thereof and the air impermeable sheet 6 on the other side as in the fourth embodiment. As a modification, the heat generating molded article may have either one of the air permeable sheet and the air impermeable sheet on only one side thereof or may have the air permeable sheet on both sides thereof.

Figure 11:
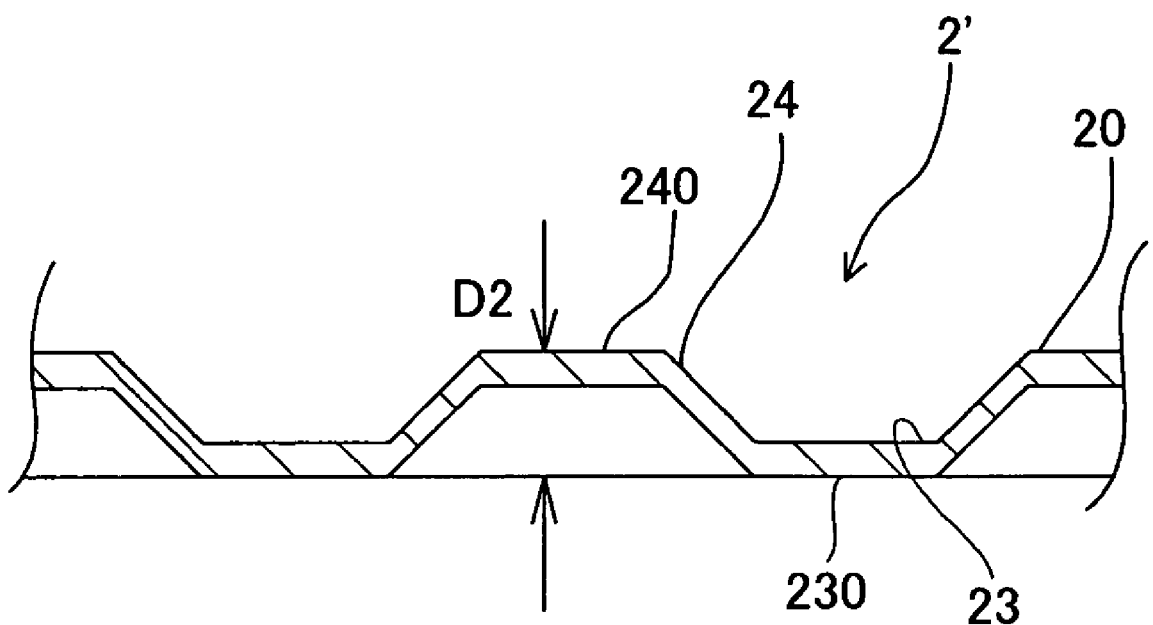
FIG. 11 is a schematic fragmentary cross-sectional view of another embodiment of the present invention (corresponding to FIG. 7($b$)).

The heat generating sheet 2 according to the fifth embodiment (see FIGS. 6, 7(*a*), and 7(*b*)) is obtained by embossing the molded article of sheet form from both sides thereof by passing between matched steel embossing rolls. In a modification, the molded article may be embossed from only one side thereof by passing between an engraved roll and a flat roll to give the heat generating sheet 2' shown in FIG. 11. In this modification, the level difference D2 between the projections and the depressions is preferably 0.3 to 5 mm, more preferably 0.5 to 2 mm. With such a level difference, when the heat generating sheets are stacked one on top of another, they can be joined into a unitary sheet and prevented from sliding. The top 240 of each projection 24 (or the bottom 230 of each depression 23) formed by embossing between the engraved roll and the flat roll preferably has an area of 0.01 to 100 mm$^2$, more preferably 0.1 to 25 mm$^2$, for the same reasons as stated with respect to the heat generating sheet 2. The number of the tops 240 of the projections 24 (or the bottoms of the depressions) in an area of 100 cm$^2$ of the heat generating sheet is preferably 1 to 10000, more preferably 10 to 8000, for the same reason as for the heat generating sheet 2.

The shape of the depressions and the projections formed by the embossing is not limited to the shape adopted in the foregoing embodiments and includes a rectangle, a polygon, a circle, an ellipse, and an elongated ellipse. The bottoms and the tops are preferably flat but may be curved. Furthermore, the cross-sectional contour of the projections and the depressions is not limited and includes a trapezoid (as in the above-mentioned embodiment), a triangle, a rectangle, a semicircle, a semi-ellipse, a half elongated ellipse, and a bell shape.

The applicability of the heat generating sheet according to the present invention is not particularly limited. In addition to the use as a heat generating sheet, the heat generating sheet of the present invention can be combined with various functional preparations for, for example, cleaning, sterilization, slow wax release, scenting or deodorization to provide a hot brush suited for use in home care applications (cleaning or treatment of flooring, tatami, kitchen stoves and fans, etc.), car care applications (cleaning and waxing), facial and body skin care applications (cleansing, sanitization, moisturizing, and make-up removal), and pet care applications (e.g., brushing).

While the molded article 20 having the holes 200 is effectively used as superposed on both sides of the molded article 21 having no holes as in the heat generating sheet 2 of the above-described embodiment (see FIGS. 8, 9(*a*), and 9(*b*)), the molded article 20 may be used singularly, or two or more molded articles 20 may be used as stacked one on top of another. Where molded articles with holes are stacked, the molded articles 20 to be stacked may have the same shape and arrangement of holes 200 as in the heat generating sheet 2 of the embodiment, or the molded articles to be stacked may have different shape and arrangement of the holes.

The shape of the holes formed through the molded article is not limited to the shape adopted in the foregoing embodiment and includes a rectangle, a polygon, an ellipse, and an elongated ellipse.

Figure 12:
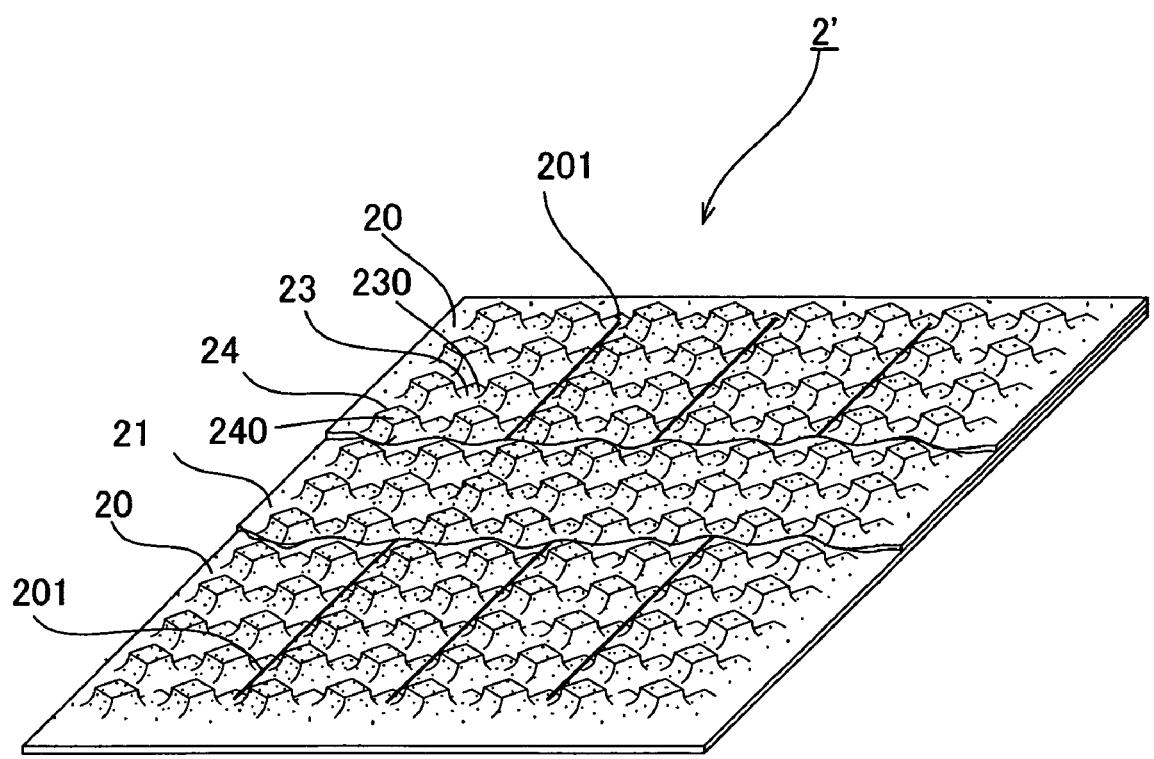
FIG. 12 is a schematic perspective view of another embodiment of the heat generating sheet according to the present invention (corresponding to FIG. 8).

In the heat generating sheet of the above-described embodiment, a number of holes 200 made in the molded article 20 may be replaced with cuts 201 as in the heat generating sheet 2' shown in FIG. 12. The length of the individual cuts is preferably 1 to 50 mm, more preferably 5 to 30 mm, to achieve the same purposes as described for the heat generating sheet 2. The total length of the cuts per unit area is preferably 5 to 100 mm/cm$^2$, more preferably 10 to 50 mm/cm$^2$, for the same reasons as for the heat generating sheet 2. The cut 201 may or may not reach the edge of the molded article 2.

Figure 13:
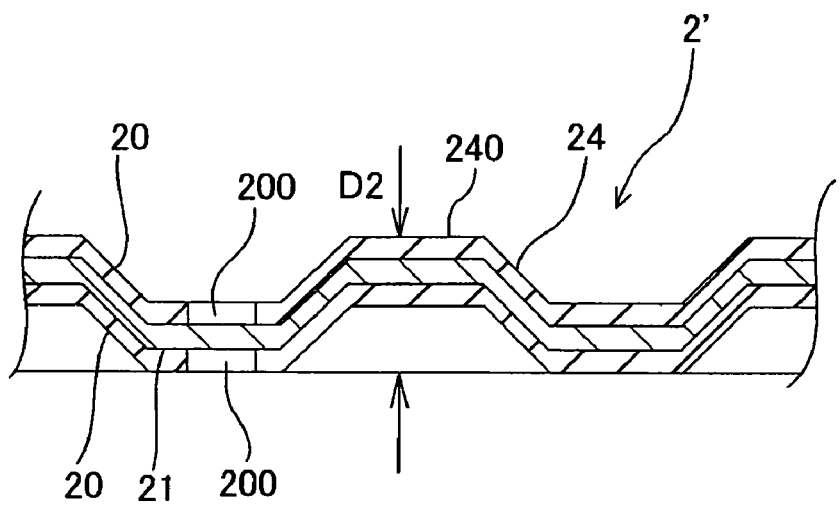
FIG. 13 is a schematic fragmentary cross-sectional view of another embodiment of the heat generating sheet according to the present invention (corresponding to FIG. 9($b$)).

The heat generating sheet 2 according to the above-described embodiment is obtained by embossing the molded articles from both sides thereof by passing between matched steel embossing rolls. In a modification, the molded articles may be embossed from only one side thereof by passing between an engraved roll and a flat roll to give the heat generating sheet 2' shown in FIG. 13. In this modification, the level difference D2 between the projections and the depressions is preferably 0.3 to 5 mm, more preferably 0.5 to 2 mm. With such a level difference, the heat generation characteristics are enhanced, and, when the heat generating sheets are stacked one on top of another, they can be prevented from sliding and joined into a unitary sheet. The top 220 of each projection 22 (or the bottom of each depression) formed by embossing between the engraved roll and the flat roll preferably has an area of 0.01 to 100 mm$^2$, more preferably 0.1 to 25 mm$^2$, for the same reasons as stated with respect to the heat generating sheet 2. The number of the tops 240 of the projections 24 (or the bottoms of the depressions) in an area of 10 cm$^2$ of the heat generating sheet is preferably 1 to 10000, more preferably 10 to 8000, for the same reason as for the heat generating sheet 1.

The shape of the depressions and the tops formed on the molded articles by the embossing is not limited to the shape adopted in the foregoing embodiment and includes a rectangle, a polygon, a circle, an ellipse, and an elongated ellipse. The depressions and the tops are preferably flat but may be curved. Furthermore, the cross-sectional contour of the projections and the depressions is not limited and includes a trapezoid (as in the above-mentioned embodiment), a triangle, a rectangle, a semicircle, a semi-ellipse, a half elongated ellipse, and a bell shape.

The applicability of the heat generating sheet according to the present invention is not particularly limited. In addition to the use as a heat generating sheet, the heat generating sheet of the invention, being held in the air-permeable holder, can be combined with various functional preparations for, for example, cleaning, sterilization, slow wax release, scenting or deodorization for use in home care applications (cleaning or treatment of flooring, tatami, kitchen stoves and fans, etc.), car care applications (cleaning and waxing), and facial and body skin care applications (cleansing, sanitization, moisturizing, and make-up removal).

EXAMPLES

The present invention will now be illustrated in greater detail with reference to Examples.

In Example 1-1 and Comparative Examples 1-1 and 1-2, warming devices were prepared. The thickness, flexural strength, and heat generation characteristics of the resulting warming devices were measured as described hereunder. The results obtained are shown in Table 1-1.

Example 1-1

(1) Formulation of Raw Material Composition

Oxidizable metal: iron powder, RKH (trade name) from Dowa Iron Powder Co., Ltd. 75 wt %

Fibrous material: pulp fiber NBKP, Mackenzie (trade name) from Fletcher

Challenge Canada, Ltd.; CSF: 200 ml 15 wt %

Moisture retaining agent: activated carbon, Carboraffin (trade name) from Takeda Chemical Industries, Ltd.; average particle size: 43 μm 10 wt %

To 100 parts by weight of the composition of the above components were added 0.2 parts by weight of sodium carboxymethyl cellulose, Cellogen WS-C (trade name) from Dai-ichi Kogyo Seiyaku Co., Ltd., as a flocculant and 0.3 parts by weight of a polyamide-epichlorohydrin resin, WS552 (trade name) from Japan PMC Corp.) as a flocculant. Water (industrial water) was added thereto to result in a solids concentration of 0.3%.

(2) Papermaking Conditions

The raw material composition was formed into sheeting on an inclined short-wire paper machine to prepare a wet molded sheet.

(3) Drying Conditions

The wet molded sheet was press dewatered between felt blankets, passed as such between 120° C. heated rolls to be dried to a water content of 5 wt % or less to obtain a molded sheet (heat generating sheet precursor) having a basis weight of 180 g/m² and a thickness of 0.25 mm.

As a result of measurement with a thermogravimetric analyzer (TG/DTA 6200 from Seiko Instruments Inc.), the resulting heat generating sheet precursor was found to be made up of 72 wt % iron, 17 wt % pulp, and 11 wt % activated carbon.

(4) Preparation of Heat Generating Sheet

Six of the resulting molded sheets (heat generating sheet precursors) were stacked one on top of another, and the weight of the stack was adjusted to 1060 g/m². An electrolytic solution described below was sprayed on the stack to obtain a heat generating sheet containing 60 parts by weight of the electrolytic solution per 100 parts by weight of the heat generating sheet precursors.

Electrolytic Solution:
Electrolyte: purified salt (NaCl)
Water: industrial water
Concentration: 5% by mass As a result of measurement with a thermogravimetric analyzer (TG/DTA 6200 from Seiko Instruments Inc.), the resulting heat generating sheet was found to be made up of 45 wt % iron, 10.6 wt % pulp, 6.9 wt % activated carbon, 1.9 wt % NaCl, and 35.6 wt % water.

(5) Preparation of Warming Device

A stack of four air-impermeable, non-liquid retentive, highly expanded polyethylene sheets, Miramat (trade name) #110 available from JSP Corp., having a thickness of 1 mm each was disposed under the resulting heat generating sheet as a heat insulating sheet. A nonwoven fabric/porous polyethylene sheet laminate having a water vapor permeability of 500 g/(m²·24 hr) and a basis weight of 100 g/m² (Breathron 1500, available from Nitto Denko Corp.) was superposed as an air permeable sheet on the upper side of the heat generating sheet. A PE film weighing 20 g/m² was superposed as an air impermeable sheet on the lower side of the heat insulating sheet. The air permeable sheet and the air impermeable sheet were heat sealed around the perimeter of the heat generating sheet. Air-through nonwoven fabric made of PET/PE core/sheath conjugate fibers and having a basis weight of 20 g/m² was used as a surfacing member on the air impermeable sheet side.

Comparative Example 1-1

A warming device was prepared in the same manner as in Example 1-1, except for using, as a heat insulating sheet, air-permeable and liquid-retentive urethane foam, TL (trade name) from Bridgestone Corp. having a thickness of 5 mm.

Comparative Example 1-2

A commercially available warming device, Hokaron Zabuton manufactured and sold in 2003 by Lotte Denshi, Inc. (240 mm×330 mm), was used.

(a) Thickness Measurement

The thickness of the warming device obtained in Example and Comparative Examples was measured with a slide gauge (from Mitutoyo Corp.) at five or more different points to obtain an average. The warming device of Comparative Example 1-2 was horizontally shaken a few times with its both ends held by hands to even the thickness prior to the thickness measurement.

(b) Flexural Strength Measurement

The flexural strength of the resulting warming device was measured by three point bending flexural test using a tensile/compression tester, RTA-500 from Orientec. A test specimen measuring 5 cm by 30 cm was cut out of the warming device, placed on the tester at a span length of 50 mm between the supports, and pressed at the middle with an indenter having a radius of 5 mm at a crosshead speed of 20 mm/min. The flexural strength was obtained from equation:

$$\text{Flexural strength(N/cm)}=\text{Maximum bending load(N)}/\text{sample width(cm)}$$

(c) Measurement of Heat Generation Characteristics

Figure 14:
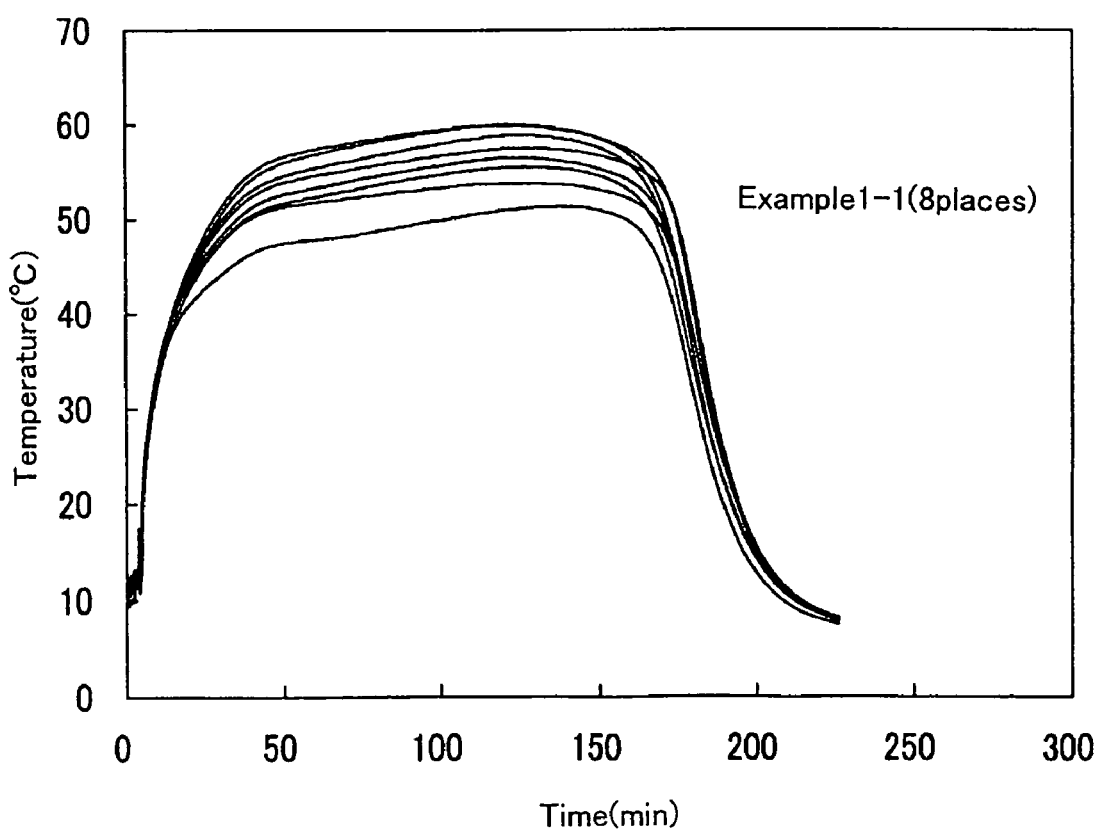
FIG. 14 is a graph showing changes of heat generation temperature with time in a warming device prepared in Example.
Figure 15:
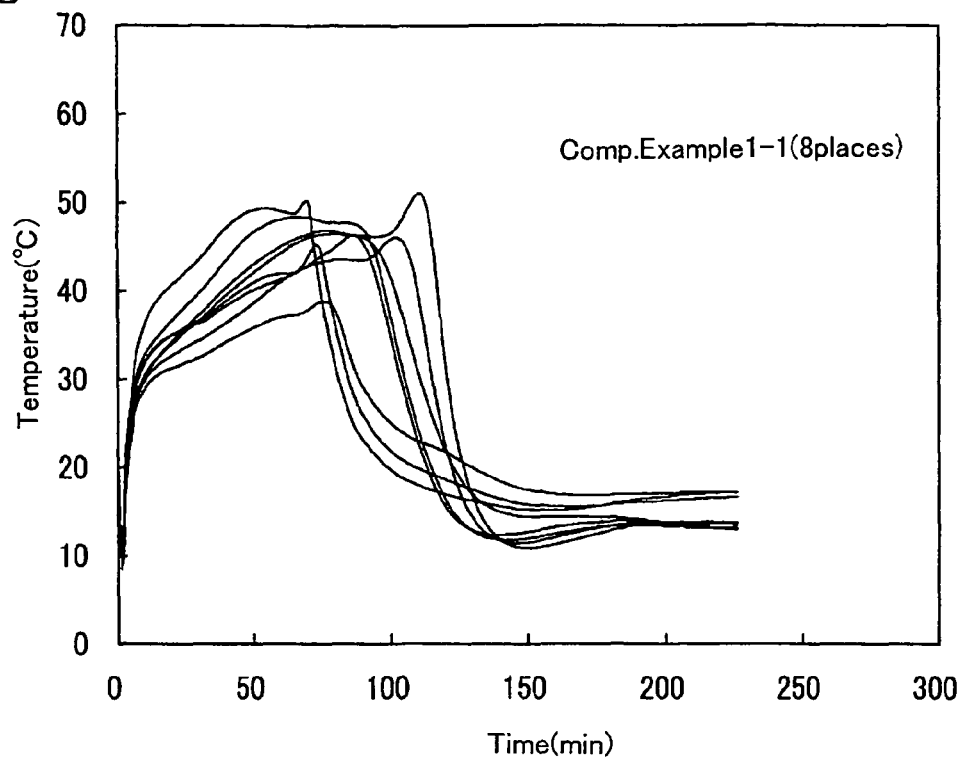
FIG. 15 is a graph showing changes of heat generation temperature with time in a warming device prepared in Comparative Example.
Figure 16:
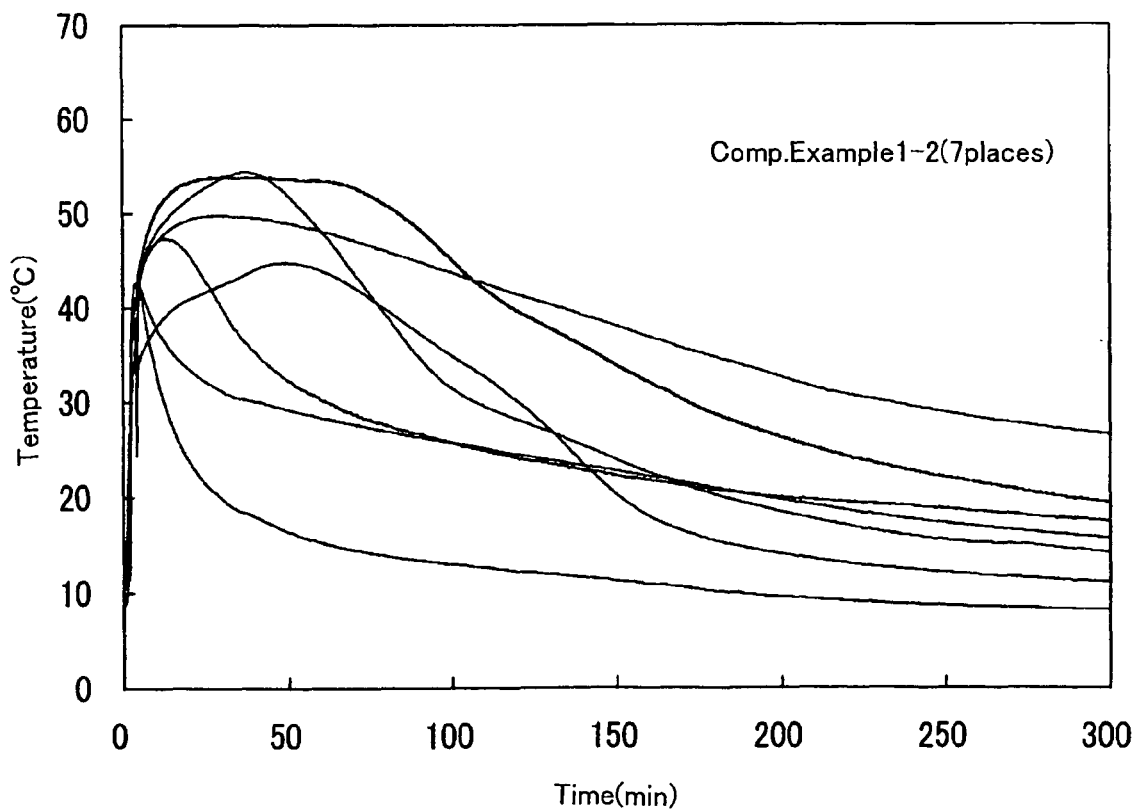
FIG. 16 is a graph showing changes of heat generation temperature with time in another warming device prepared in Comparative Example.

The warming device was placed on a 5 mm thick polypropylene plate with its air permeable side up in a chamber maintained at 5° C. Seven or eight temperature sensors were set at arbitrarily chosen positions on the air permeable sheet, and a blanket was overlaid thereon. The results obtained are shown in FIGS. 14 to 16.

TABLE 1-1

|  | Thickness (mm) | Flexural Strength (N/cm) | | Maximum Heat Generation Temperature (° C.) | Duration of Maintaining 30° C. or Higher (min) |
| --- | --- | --- | --- | --- | --- |
|  |  | Before Heat Generation | After Heat Generation |  |  |
| Example 1-1 | 7.3 | 0.40 | 0.93 | 51.4-60.0 | 172.8-178.0 |
| Comp. Example 1-1 | 6.8 | 0.26 | 0.55 | 38.8-51.1 | 75.2-111.3 |
| Comp. Example 1-2 | 9-30 | * | * | 42.4-54.4 | 10.2-228.8 |

*: When cut to 50 mm width, the product crumbled along the cut edges. Flexural strength of the specimen inclusive of the powder was unmeasurable.

It is seen from FIG. 14 that the warming device of Example (the present invention) exhibits almost equal heat generation characteristics at difference sites of measurement and stably sustains heat generation at 40° C. or higher for a prolonged period of time. As shown in Table 1-1, the warming device of Example is thin, flexible, and convenient to carry. In contrast, as shown in FIGS. 15 and 16, the warming devices of Comparative Examples show considerable variation in heat generation temperature from site to site, and heat generation at 40° C. or higher does not last long at most of the sites of measurement.

In Examples 2-1 and 2-2 and Comparative Example 2-1, warming devices were prepared. The thickness, flexural strength, and heat generation characteristics of the resulting warming devices were measured as described hereunder. The results obtained are shown in Table 2-1.

Example 2-1

(1) Formulation of Raw Material Composition

Oxidizable metal: iron powder, RKH (trade name) from Dowa Iron Powder Co., Ltd. 75 wt %
Fibrous material: pulp fiber NBKP, Mackenzie (trade name) from Fletcher
Challenge Canada, Ltd.; CSF: 200 ml 15 wt %
Moisture retaining agent: activated carbon, Carboraffin (trade name) from Takeda Chemical Industries, Ltd.; average particle size: 43 μm 10 wt %
To 100 parts by weight of the composition of the above components were added 0.2 parts by weight of sodium carboxymethyl cellulose, Cellogen WS-C (trade name) from Dai-ichi Kogyo Seiyaku Co., Ltd., as a flocculant and 0.3 parts by weight of a polyamide-epichlorohydrin resin, WS552 (trade name) from Japan PMC Corp.) as a flocculant. Water (industrial water) was added thereto to result in a solids concentration of 0.3%.

(2) Papermaking Conditions

The raw material composition was formed into sheeting on an inclined short-wire paper machine to prepare a wet molded sheet.

(3) Drying Conditions

The wet molded sheet was press dewatered between felt blankets, passed as such between 120° C. heated rolls to be dried to a water content of 5 wt % or less to obtain a molded sheet (heat generating sheet precursor) having a basis weight of 180 g/m$^2$ and a thickness of 0.25 mm. As a result of measurement with a thermogravimetric analyzer (TG/DTA 6200 from Seiko Instruments Inc.), the resulting heat generating sheet precursor was found to be made up of 72 wt % iron, 17 wt % pulp, and 11 wt % activated carbon.

(4) Preparation of Heat Generating Sheet

Six of the resulting molded sheets (heat generating sheet precursors) were stacked one on top of another, and the basis weight of the stack was adjusted to 1060 g/m$^2$. An electrolytic solution described below was sprayed to the stack to obtain a heat generating sheet. As a result of measurement with a thermogravimetric analyzer (TG/DTA 6200 from Seiko Instruments Inc.), the resulting heat generating sheet was found to be made up of 45 wt % iron, 10.6 wt % pulp, 6.9 wt % activated carbon, 1.9 wt % NaCl, and 35.6 wt % water.
Electrolytic Solution:
Electrolyte: purified salt (NaCl)
Water: industrial water
Concentration: 5% by mass (5) Preparation of Warming Device A stack of four air-impermeable, highly expanded polyethylene sheets, Miramat (trade name) #110, available from JSP Corp., having a thickness of 1 mm each was disposed under the resulting heat generating sheet as a heat insulating sheet. A nonwoven fabric/porous polyethylene sheet laminate having a water vapor permeability of 500 g/(m$^2$·24 hr) and a basis weight of 100 g/m$^2$ (Breathron 1500 from Nitto Denko Corp.) was superposed as an air permeable sheet on the upper side of the heat generating sheet. A PE film weighing 20 g/m$^2$ was superposed as an air impermeable sheet on the lower side of the heat insulating sheet. The air permeable sheet and the air impermeable sheet were heat sealed around the perimeter of the heat generating sheet. Air-through nonwoven fabric made of PET/PE core/sheath conjugate fibers and having a basis weight of 20 g/m$^2$ was used as a surfacing member on the air impermeable sheet side.

Example 2-2

A warming device was prepared in the same manner as in Example 2-1, except for using, as a heat insulating sheet, air-permeable urethane foam TL (trade name) from Bridgestone Corp. having a thickness of 5 mm and disposing an air impermeable PE film between the heat generating sheet and the heat insulating sheet.

Comparative Example 2-1

A commercially available warming device, Hokaron Zabuton manufactured and sold in 2003 by Lotte Denshi, Inc. (240 mm×330 mm), was used.
(a) Thickness Measurement
The thickness of the warming devices obtained in Example and Comparative Examples was measured with a slide gauge (from Mitutoyo Corp.) at five or more different points to obtain an average. The warming device of Comparative Example 2-2 was horizontally shaken a few times with its both ends held by hands to even the thickness prior to the thickness measurement.

(b) Flexural Strength Measurement

The flexural strength of the resulting warming device was measured by three point bending flexural test using a tensile/compression tester, RTA-500 from Orientec. A test specimen measuring 5 cm by 30 cm was cut out of the warming device, placed on the tester at a span length of 50 mm between the supports, and pressed at the middle with an indenter having a radius of 5 mm at a crosshead speed of 20 mm/min. The flexural strength was obtained from equation:

Flexural strength(N/cm)=Maximum bending load(N)/sample width(cm)

(c) Measurement of Heat Generation Characteristics

Figure 17:
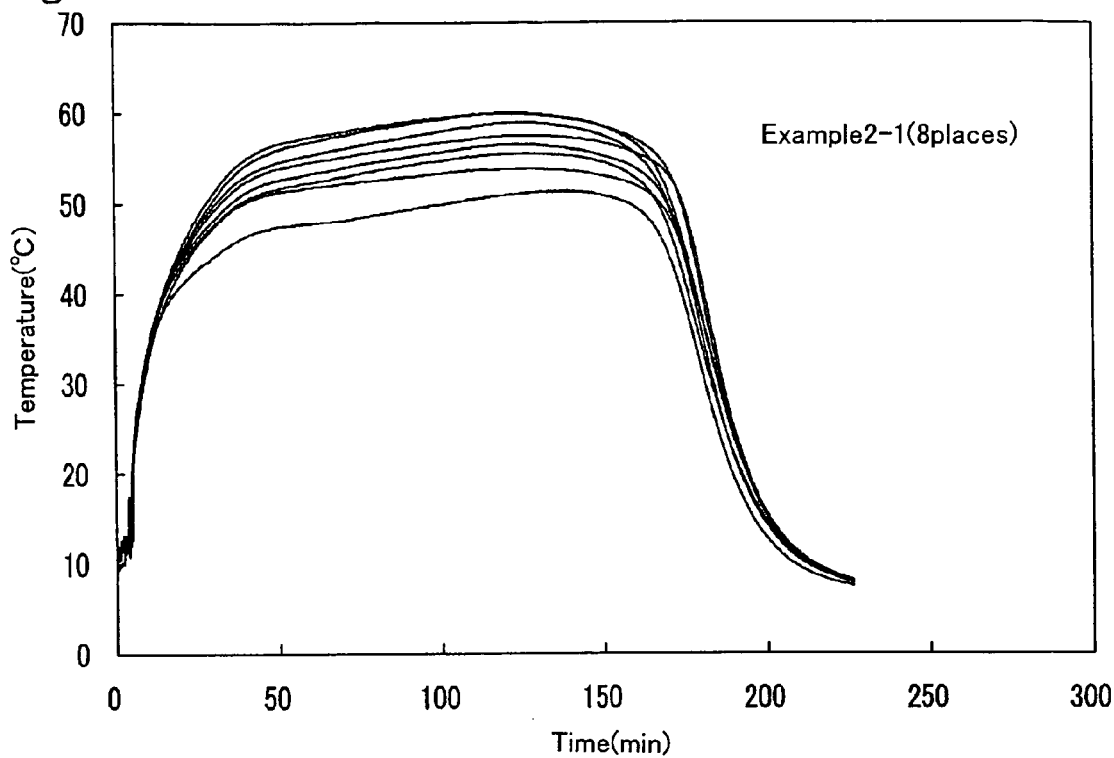
FIG. 17 is a graph showing changes of heat generation temperature with time in another warming device prepared in Example.
Figure 18:
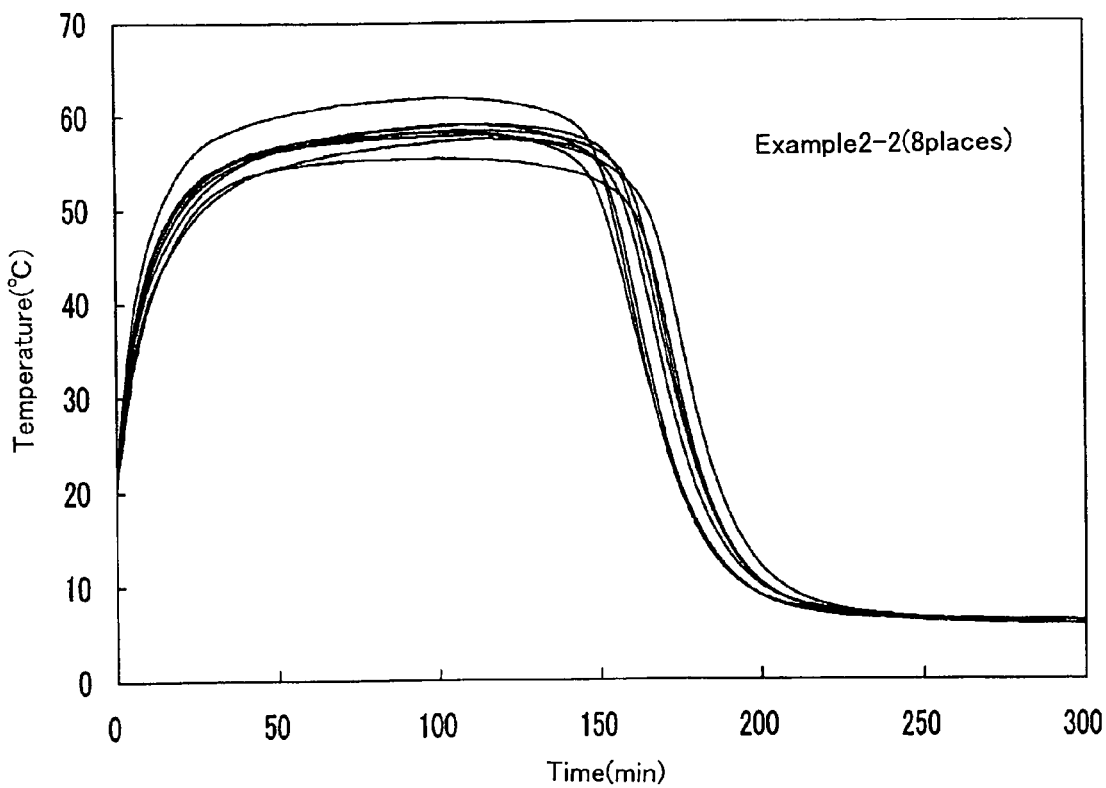
FIG. 18 is a graph showing changes of heat generation temperature with time in still another warming device prepared in Comparative Example.

The warming device was placed on a 5 mm thick polypropylene plate with its air permeable sheet side up in a chamber maintained at 5° C. Seven or eight temperature sensors were set at arbitrarily chosen positions on the air permeable sheet, and a blanket was overlaid thereon. The results obtained are shown in FIGS. 17 to 18.

TABLE 2-1

| | Thickness (mm) | Flexural Strength (N/cm) | | Maximum Heat Generation Temperature (° C.) | Duration of Maintaining 40° C. or Higher (min) |
| | | Before Heat Generation | After Heat Generation | | |
| --- | --- | --- | --- | --- | --- |
| Example 2-1 | 7.3 | 0.40 | 0.93 | 51.4-60.0 | 172.8-178.0 |
| Example 2-2 | 6.9 | 0.24 | 0.70 | 55.0-62.0 | 164.0-175.7 |
| Comp. Example 2-1 | 9-30 | * | * | 42.4-54.4 | 10.2-288.8 |

*: When cut to 50 mm width, the product crumbled along the cut edges. Flexural strength of the specimen inclusive of the powder was unmeasurable.

Figure 19:
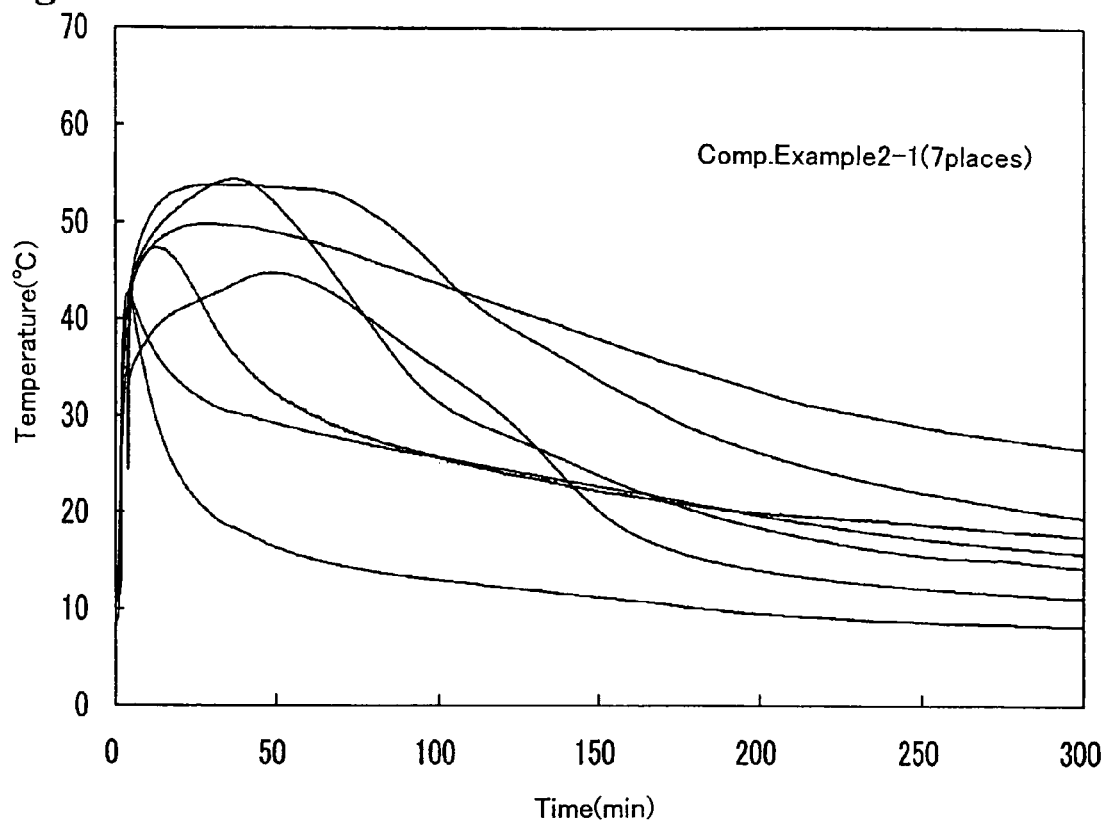
FIG. 19 is a graph showing changes of heat generation temperature with time in still another warming device prepared in Comparative Example.

As shown in Table 2-1, the warming devices of Examples (the present invention) are thin, flexible, and convenient to carry. It is seen from FIGS. 17 and 18 that the warming devices of Examples exhibit equal heat generation temperature characteristics at difference sites of measurement and stably maintain a plateau at a temperature level of 40° C. or higher for a prolonged period of time. In contrast, as shown in FIG. 19, the comparative warming device shows considerable variation in heat generation temperature from site to site, and heat generation at 40° C. or higher does not last long at most of the sites of measurement.

In Examples 3-1 to 3-4, warming devices were prepared, and the thickness and the flexural strength of the resulting warming devices were measured as described below.

Example 3-1

(1) Formulation of Raw Material Composition

Oxidizable metal: iron powder, RKH (trade name) from Dowa Iron Powder Co., Ltd. 75 wt %
Fibrous material: pulp fiber NBKP, Mackenzie (trade name) from Fletcher Challenge Canada, Ltd.; CSF: 200 ml 10 wt %
Moisture retaining agent: activated carbon, (classified by 45 μm mesh, Carboraffin (trade name) from Takeda Chemical Industries, Ltd) 15 wt %

To 100 parts by weight of the composition of the above components were added 0.25 parts by weight of sodium carboxymethyl cellulose, Cellogen WS-C (trade name) from Dai-ichi Kogyo Seiyaku Co., Ltd., as a flocculant and 0.5 parts by weight of a polyamide-epichlorohydrin resin, WS547 (trade name) from Japan PMC Corp.) as a flocculant. Water (industrial water) was added thereto to result in a solids concentration of 0.3%.

Electrolytic Solution:
Electrolyte: purified salt (NaCl)
Water: industrial water
Concentration: 5% by mass (2) Papermaking Conditions The raw material composition was formed into sheeting using a small-sized, inclined short-wire paper machine (possessed by Kochi Prefectural Paper Technology Center) at a line speed of 7 m/min to prepare a wet molded sheet.

(3) Drying Conditions

The wet molded sheet was press dewatered between felt blankets, passed as such between 120° C. heated rolls at a line speed of 7 m/min to be dried to a water content of 5 wt % or less to obtain a molded sheet (heat generating sheet precursor) having a basis weight of 100 g/m$^2$ and a thickness of 0.12 mm.

(4) Condition of Addition of Electrolytic Solution

The electrolytic solution described above was sprayed to the dried molded sheet (heat generating sheet precursor) to obtain a molded sheet (heat generating sheet).

(5) Preparation of Warming Device

Three of the resulting heat generating sheets were stacked. The air permeable sheet and the air impermeable sheet described below were superposed on the upper and the lower sides of the stack, respectively, and heat sealed around the perimeter of the stack of the heat generating sheets.

Air permeable sheet: perforated polyethylene sheet having a water vapor permeability of 1000 g/(m$^2$·24 hr) and a basis weight of 80 g/m$^2$.
Surfacing member on the surface of the air permeable sheet: air-through nonwoven fabric made of PET/PE core/sheath conjugate fibers and having a basis weight of 20 g/m$^2$.
Air impermeable sheet: PE film weighing 20 g/m$^2$.
Surfacing member on the surface of the air impermeable sheet: air-through nonwoven fabric made of PET/PE core/sheath conjugate fibers and having a basis weight of 20 g/m$^2$.

Example 3-2

A warming device was prepared in the same manner as in Example 3-1, except that five of the heat generating sheets used in Example 3-1 were stacked and that two thicknesses of perforated PE film having a water vapor permeability f 500 g/(m$^2$·24 hr) were used as an air permeable sheet.

Example 3-3

A warming device was prepared in the same manner as in Example 3-1, except that ten of the heat generating sheets used in Example 3-1 were stacked.

Example 3-4

A warming device was prepared in the same manner as in Example 3-1, except that twenty of the heat generating sheets used in Example 3-1 were stacked.

Example 3-5

The heat generating sheets of Example 3-1 were combined with the other sheets described below according to the following layer structure. The air permeable sheet and the air impermeable sheet were heat sealed in the same manner as in Example 3-1 to prepare a warming device.
Layer structure: air permeable sheet/heat generating sheets/buffer material/air impermeable sheet
Air permeable sheet: a nonwoven fabric/porous polyethylene sheet laminate (Breathron 1260 from Nitto Denko Corp.; water vapor permeability: 250 g/(m²·24 hr); basis weight: 100 g/m²)
Buffer material: polyethylene terephthalate nonwoven fabric (NA from Kuraray Co., Ltd.; basis weight: 180 g/m²; thickness: 5 mm²)
Air impermeable sheet: PE film (basis weight: 20 g/m²)

Comparative Example 3-1

A disposable body warmer, Haru On-Packs (trade name) from Mycoal Corp., a kind of commercially available warming articles, was used.

Comparative Example 3-2

A disposable foot warmer, Nakajiki Kairo Ashipoka Sheet (trade name) from Mycoal Corp., a kind of commercially available warming articles, was used.

The thickness of the warming device obtained in Examples and Comparative Examples and the flexural strength of the warming devices before heat generation and after the end of heat generation were measured as follows. The results obtained are shown in Table 3-1. Conformability of the warming devices was evaluated by comparing the flexural strengths before and after the heat generation.

(a) Thickness Measurement

The thickness of the warming device was measured with a dial gauge, Digimatic Indicator IDF-112 (measuring force: 1.28 N, available from Mitutoyo Corp.) at five or more different points to obtain an average. The thickness of the warming device of Example 5 was measured in the same manner but with a slide gauge (from Mitutoyo Corp.) in view of the buffer material.

(b) Flexural Strength Measurement (b-1) Before Heat Generation

The flexural strength of the resulting warming device was measured by three point bending flexural test using a tensile/compression tester, RTA-500 from Orientec. A test specimen cut out of the warming device was placed on the tester at a span length of 50 mm between the supports and pressed at the middle with an indenter having a radius of 5 mm at a crosshead speed of 20 mm/min. The flexural strength was obtained from equation:

Flexural strength(N/cm)=Maximum bending load(N)/sample width(cm)

(b-2) After Heat Generation

The warming device was made to heat up in an ambient atmosphere. The time when the temperature of the warming device dropped below 37° C. was regarded as the end of use. At that time, the flexural strength was measured in the same manner as described above.

TABLE 3-1

| | Thickness of Warming Device (mm) | Total Thickness of Heat Generating Sheets (mm) | Total Basis weight of Heat Generating Sheets (g/m²) | Flexural Strength (N/cm) | |
|---|---|---|---|---|---|
| | | | | Before Heat Generation | After Heat Generation |
| Example 3-1 | 0.89 | 0.4 | 300 | 0.029 | 0.077 |
| Example 3-2 | 1 | 0.7 | 550 | 0.036 | 0.389 |
| Example 3-3 | 2.41 | 1.8 | 1300 | 0.071 | 0.155 |
| Example 3-4 | 4.38 | 3.5 | 2600 | 0.145 | 0.247 |
| Example 3-5 | 7.0-8.0 | 1.1 | 850 | 0.261 | |
| Comp. Example | 1.5-4.5 | — | 4300 | 0.326 | 9.776 |
| Comp. Example 3-2 | 1.3-1.5 | — | 2200 | 0.900 | 3.391 |

As shown in Table 3-1, the warming devices of Examples (the present invention) are thin and more flexible both before and after heat generation than those of Comparative Examples.

In Examples 4-1 and 4-2 and Comparative Examples 4-1 to 4-3, a heat generating sheet precursor was prepared from a raw material composition, the formulation of which is described below and in Table 4-1. The heat generating sheet precursor was combined with other sheets as described below, embossed through matched steel embossing rolls as described below to form projections and depressions, and cut to shape to prepare a heat generating molded article containing no electrolyte. The electrolyte described below was incorporated into the molded article to obtain a desired heat generating molded article.

Example 4-1

(1) Formulation of Raw Material Composition

Oxidizable metal: iron powder, RKH (trade name) from Dowa Iron Powder Co., Ltd. 8.3 g
Fibrous material: pulp fiber (NBKP, Mackenzie (trade name) from Fletcher Challenge Canada, Ltd.; average fiber length: 2.1 mm): 1.1 g
Moisture retaining agent: activated carbon (classified by 45 μm mesh, Carboraffin (trade name) from Takeda Chemical Industries, Ltd) 1.7 g
Flocculant: sodium carboxymethyl cellulose, Cellogen WS-C (trade name) from Dai-ichi Kogyo Seiyaku Co., Ltd. 0.06 g
Flocculant: polyamide-epichlorohydrin resin, WS547 (trade name) from Japan PMC Corp. 0.44 g
Water (industrial water) 20000 g
Electrolytic Solution:
Electrolyte: purified salt (NaCl)
Water: industrial water
Concentration: 5% by mass (2) Papermaking Conditions The raw material composition was agitated at 300 rpm for 1 minute and drained through a square type standard sheet machine fitted with an 80 mesh wire manufactured by Kumagai Riki Kogyo K.K. in accordance with JIS P8209. The resulting wet sheet was dried on a KRK rotary drier (from Kumagai Riki Kyogo) to a water content of 1% by mass or lower to obtain a heat generating sheet precursor.

(3) Embossing

Mixed fiber paper containing 20% polyester fiber and having a basis weight of 20 g/m² was superposed as an air permeable sheet on both sides of the heat generating sheet precursor, and the three-layered sheet was embossed under the following conditions.
Embossing Conditions:
Embossing machine: hydraulic 4-roll embossing machine manufactured by Yuri Roll Co., Ltd.; relief height: 1 mm
Pressing temperature: room temperature
Pressing pressure: adjusted to give a difference of 1 mm between projections and depressions
Distance D10: 1 mm
Shape and area of bottoms and tops: ellipse (major diameter: 2 mm; minor diameter: 1 mm); 1.6 mm² each; number of bottoms of depressions and tops of projections per 100 cm²: 2500

(4) Condition of Addition of Electrolytic Solution

The molded article free of electrolyte was cut into a 50 mm by 50 mm square. The electrolytic solution described above was syringed onto the embossed side or between layers to penetrate throughout the molded sheet by capillarity to obtain a heat generating molded article containing 35% of the electrolytic solution based on the weight of the heat generating sheet precursor.

Example 4-2

A heat generating molded article was prepared in the same manner as in Example 4-1, except for changing the difference between projections and depressions to 0.3 mm.

Comparative Example 4-1

A heat generating molded article was prepared in the same manner as in Example 4-1, except that two of the heat generating sheets of Example 4-1 were stacked and not embossed.

Comparative Example 4-2

A heat generating molded article was prepared in the same manner as in Example 4-2, except for using pulp having a freeness of 700 ml.

Comparative Example 4-3

A heat generating molded article was prepared in the same manner as in Example 4-1, except for using pulp having a freeness of 700 ml.

The unity of the heat generating sheet precursor and the air permeable sheets in the heat generating molded article was evaluated by observing sliding between the sheets and fall-off of powder from a cut area as follows. The heat generation characteristics of the heat generating molded article were also examined. The results are shown in Table 2.
(a) Evaluation of Unity of Molded Article
A 50 mm×50 mm square was cut out of the heat generating molded article containing no electrolyte and continuously shaken on a vibrator (Touch Mixer MT-51 available from Yamato Scientific Co., Ltd.) with a sheet of white paper fixed on the vibrating surface at "speed set memory 1". Sliding and fall-off of constituents from the cut areas were rated on the following A to C scale, and the unity of the molded article was evaluated based on the rates.
(a-1) Sliding Between Sheets
A: No sliding occurs when shaken for 1 minute.
B: Sliding occurs in 1 minute shaking with a sliding displacement of 5 mm or less.
C: Sliding occurs in 1 minute shaking with a sliding displacement of 5 mm or more.
(a-2) Fall-off of Constituents From Cut Areas
A: Scarcely any powder is observed on the white paper after 1 minute shaking.
B: Some fallen powder is observed on the white paper in a part of the area in which the multilayered sheet has moved.
C: A considerable amount of fallen powder is observed on the white powder in the entire area in which the multilayered sheet has moved.
(b) Evaluation of Heat Generation Characteristics
A tester having a 4.2-liter closed chamber adjusted to 1% RH or less in which 5.0 l/min of dry air was fed was prepared. The heat generating molded article containing the electrolyte (50 cm×50 cm) was placed with the a water vapor permeable sheet side up in the chamber to induce heat generating reaction. The temperature of the lower side of the heat generating sheet was measured with a thermocouple.

|  | Composition of Slurry on Solid Basis (wt %) | | | | Components | | | |
|---|---|---|---|---|---|---|---|---|
|  | Oxidizable Metal | Fibrous Material | Moisture Retaining Agent | CSF (ml) | other than Fibrous Material (wt %) | Breaking Length (m) | Relief Height (mm) | Basis weight of Sheet (g/m²) |
| Example 4-1 | 75 | 10 | 15 | 250 | 76.5 | 108 | 1 | 416 |
| Example 4-2 | 75 | 10 | 15 | 250 | 76.5 | 108 | 0.3 | 450 |
| Comp. Example 4-1 | 75 | 10 | 15 | 250 | 76.5 | 108 | 0 | 410 |
| Comp. Example 4-2 | 75 | 10 | 15 | 700 | 60.3 | 8.7 | 1 | 396 |
| Comp. Example 4-3 | 75 | 10 | 15 | 700 | 60.3 | 8.7 | 0.3 | 358 |

TABLE 4-2

| | Heat Generation Characteristics | | | |
|---|---|---|---|---|
| | Maximum Temp. (° C.) | Duration of maintaining 40° C. or Higher (min) | Unity Sliding | Fall-off of Powder |
| Example 4-1 | 45 | 2.2 | A | A |
| Example 4-2 | 48 | 2.8 | A | B |
| Comp. Example 4-1 | 48 | 1.8 | C | B |
| Comp. Example 4-2 | 43 | 1.8 | A | C |
| Comp. Example 4-3 | 40 | 0 | B | C |

As is shown in Table 4-2, the heat generating elements of Examples are united with superposed sheets and prevented from sliding between the sheets, hardly suffer from fall-off of constituent components, and exhibit satisfactory heat generation characteristics.

In Examples 5-1 and 5-2 and Comparative Examples 5-1 to 5-3, heat generating sheets having the composition shown in Table 5-1 were prepared. The resulting heat generating sheets were stacked one on top of another and embossed through matched steel embossing rolls as described below to form projections and depressions. The embossed structure was cut to shape to prepare a heat generating sheet 2.

Example 5-1

(1) Formulation of Raw Material Composition

Oxidizable metal: iron powder, RKH (trade name) from Dowa Iron Powder Co., Ltd. 8.3 g
Fibrous material: pulp fiber (NBKP, Mackenzie (trade name) from Fletcher Challenge Canada, Ltd.; average fiber length: 2.1 mm) 1.1 g
Moisture retaining agent: activated carbon (classified by 45 μm mesh, Carboraffin (trade name) from Takeda Chemical Industries, Ltd) 1.7 g
Flocculant: sodium carboxymethyl cellulose, Cellogen WS-C (trade name) from Dai-ichi Kogyo Seiyaku Co., Ltd. 0.06 g
Flocculant: polyamide-epichlorohydrin resin, WS547 (trade name) from Japan PMC Corp. 0.44 g
Water (industrial water) 20000 g
Electrolytic Solution:
Electrolyte: purified salt (NaCl)
Water: industrial water
Concentration: 5% by mass (2) Papermaking Conditions The raw material composition was agitated at 300 rpm for 1 minute and drained through a square type standard sheet machine fitted with an 80 mesh wire manufactured by Kumagai Riki Kogyo K.K. in accordance with JIS P8209. The resulting wet sheet was dried on a KRK rotary drier (from Kumagai Riki Kyogo) to a water content of 1% by mass or lower to obtain a molded sheet.

(3) Embossing

Two of the resulting molded sheets (molded articles of sheet form) were stacked together and embossed under the following conditions.

Embossing machine: hydraulic 4-roll embossing machine manufactured by Yuri Roll Co., Ltd.; relief height: 1 mm
Pressing temperature: room temperature
Pressing pressure: adjusted to give a difference of 1 mm between projections and depressions
Distance D2: 1 mm
Shape and area of bottoms and tops: ellipse (major diameter: 2 mm; minor diameter: 1 mm); 1.6 $mm^2$ each; number of bottoms of depressions and tops of depressions per 100 $cm^2$: 2500

(4) Condition of Addition of Electrolytic Solution

The embossed stack of the molded articles was cut into a 50 mm by 50 mm square, which was impregnated with 35%, based on the weight of the resulting stack of heat generating sheets, of the electrolytic solution described above by spraying. A tester having a 4.2-liter closed chamber adjusted to 1% RH or less in which 5.0 l/min of dry air was fed was prepared. The stack of the heat generating sheets was placed in the chamber with the water vapor permeable sheet side up to induce heat generating reaction.

The temperature of the lower side of the heat generating sheets was measured with a thermocouple.

Example 5-2

A stack of heat generating sheets was prepared in the same manner as in Example 5-1, except for changing the difference between projections and depressions to 0.3 mm.

Comparative Example 5-1

A stack of heat generating sheets was prepared in the same manner as in Example 5-1, except that the two heat generating sheets of Example 5-1 were not embossed.

Comparative Example 5-2

A stack of heat generating sheets was prepared in the same manner as in Example 5-1, except for using pulp having a freeness of 700 ml.

Comparative Example 5-3

Figure 20:
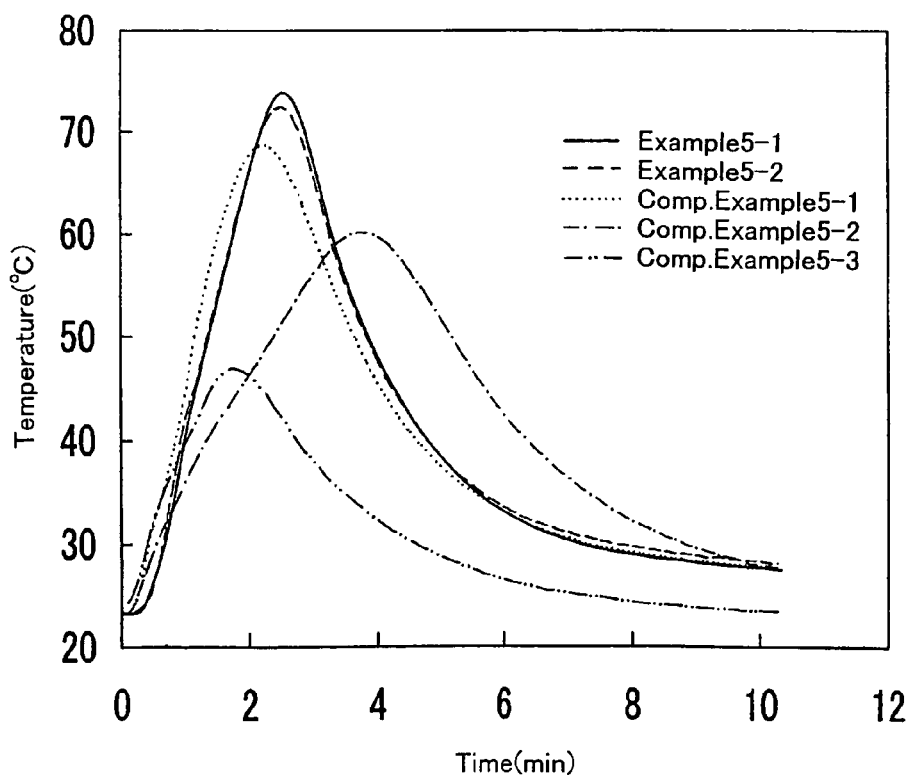
FIG. 20 is a graph showing heat generation characteristics of other heat generating sheets prepared in Examples and Comparative Examples.

A stack of heat generating sheets was prepared in the same manner as in Example 5-2, except for using pulp having a freeness of 700 ml.
(a) Evaluation of Shape Retention of Heat Generating Sheet
The resulting stacks of heat generating sheets were evaluated based on the following criteria. The results are shown in Table 5-2.
A: Fall-off of the components is scarce, and the embossed profile is retained.
B: Fall-off of the components is scarce, or the embossed profile is retained.
C: Fall-off of the components is considerable, and the sheet has no shape retention (easily crumbles).
(b) Evaluation of Heat Generation Characteristics
The stack of heat generating sheets was cut into a 50 cm×50 cm square. A water vapor permeable sheet having a water vapor permeability (JIS Z208) of 5000 g/($m^2$·24 hr) and a water vapor impermeable sheet were superposed on the respective sides of the stack and joined along the periphery to enclose the heat generating sheets therein. The thus enclosed stack of heat generating sheet was placed with the water vapor permeable sheet side up in a 4.2-liter closed chamber having a relative humidity of 1% or lower while feeding 5.0 l/min of dry air into the chamber to induce heat generation. The temperature of the lower side of the heat generating sheet stack was measured with a thermocouple. The results of the measurement are shown in FIG. 20. The maximum temperature reached and the duration of maintaining temperatures at or above 40° C. are shown in Table 5-2.

(c) Evaluation of Non-Sliding Properties

The stack of heat generating sheets was cut into a 50 cm×50 cm square. The cut piece was continuously shaken on a vibrator (Touch Mixer MT-51 available from Yamato Scientific Co., Ltd.) at "speed set memory 1". Evaluation was made based on the following criteria. The results are shown in Table 5-2.

A: Sliding of the heat generating sheets does not occur in 1 minute shaking.
B: Sliding of the heat generating sheets occurs in 1 minute shaking with a displacement of 5 mm or less.
C: Sliding of the heat generating sheets occurs in 1 minute shaking with a displacement of 5 mm or more, or the heat generating sheets crumble to lose their shape of a sheet.

TABLE 5-1

| | Composition of Slurry on Solid Basis (wt %) | | | | Components other than |
|---|---|---|---|---|---|
| | Oxidizable Metal | Fibrous Material | Moisture Retaining Agent | CSF (ml) | Fibrous Material (wt %) |
| Example 5-1 | 75 | 10 | 15 | 250 | 76.5 |
| Example 5-2 | 75 | 10 | 15 | 250 | 76.5 |
| Comp. Example 5-1 | 75 | 10 | 15 | 250 | 76.5 |
| Comp. Example 5-2 | 75 | 10 | 15 | 700 | 60.3 |
| Comp. Example 5-3 | 75 | 10 | 15 | 700 | 60.3 |

TABLE 5-2

| | Breaking Length (m) | Distance D between Projection and Depression (mm) | Basis weight of Sheet (g/m$^2$) | Shape Retention of Sheet | Heat Generation Characteristics | | Non sliding |
|---|---|---|---|---|---|---|---|
| | | | | | Max. Temp. (° C.) | Duration of maintaining 40° C. or Higher | |
| Example 5-1 | 108 | 1 | 341 | A | 74 | 3.8 | A |
| Example 5-2 | 108 | 0.3 | 343 | A | 73 | 3.8 | A |
| Comp. Example 5-1 | 108 | 0 | 361 | * | 70 | 3.7 | C |
| Comp. Example 5-2 | 8.7 | 1 | 326 | B | 60 | 5 | C |
| Comp. Example 5-3 | 8.7 | 0.3 | 184 | C | 47 | 1.7 | C |

* Not evaluated because embossing was not done.

As shown in Table 5-2, the sheets of Examples show better embossing properties and higher unity (reduced sliding) than the comparative ones. As shown in FIG. 20, the heat generating sheets of Examples exhibit high heat generating capabilities immediately after the start of use, proving excellent in heat generation characteristics.

In Examples 6-1 to 6-3 and Comparative Example 6-1, molded sheets were prepared, and heat generating sheets were prepared from the resulting molded sheets.

Example 6-1

(1) Formulation of Raw Material Composition

Oxidizable metal: iron powder (classified by 45 μm mesh), RKH (trade name) from Dowa Iron Powder Co., Ltd., 150 g
Fibrous material: pulp fiber NBKP, Skeena (trade name) produced by Skeena; average
fiber length: 2.1 mm
20 g
Fibrous material: polyvinyl alcohol fiber, VPB107-1 (trade name) from Kuraray Co., Ltd. 2.0 g
Moisture retaining agent: activated carbon (classified by 45 μm mesh), Carboraffin (trade name) from Takeda Chemical Industries, Ltd.; average particle size: 45 μm,
30 g
Flocculant: sodium carboxymethyl cellulose, Cellogen WS-C (trade name) from Dai-ichi Kogyo Seiyaku Co., Ltd. 0.5 g
Flocculant: polyamide-epichlorohydrin resin, WS547 (trade name) from Japan PMC Corp. 0.5 g
Water (industrial water) 99800 g (2) Papermaking Conditions The raw material composition was formed into sheeting using a small-sized, inclined short-wire paper machine (possessed by Kochi Prefectural Paper Technology Center) at a line speed of 7 m/min to prepare a wet molded sheet.

(3) Dewatering and Drying Conditions

The wet molded sheet was press dewatered between felt blankets, passed as such between 120° C. heated rolls at a line speed of 7 m/min to be dried to a water content of 5 wt % or less.

(4) Perforating

The resulting molded sheet (molded article of sheet form) was needle-punched to make holes of 0.5 mm in diameter at a distance of 3 mm at a density of 12 holes per 10 cm$^2$.

(5) Condition of Addition of Electrolytic Solution

Four of the resulting molded sheets (0.14 mm thick each) were stacked one on top of another, and the stack was impregnated with an electrolytic solution described below by spraying to obtain a stack of heat generating sheets having a water content of 36%.
Electrolytic solution:
Electrolyte: purified salt (NaCl)
Water: industrial water
Concentration: 5 wt %
Heat Generation Characteristics of Heat Generating Sheet:

The stack of heat generating sheets was cut into a 50 cm×50 cm square. A water vapor permeable sheet having a water vapor permeability (JIS Z208) of 600 g/(m²·24 hr) and a water vapor impermeable sheet were superposed on the respective sides of the cut stack and joined along the periphery to enclose the sheets therein. The thus enclosed stack of heat generating sheets was placed with the water vapor permeable sheet side up in a 4.2-liter closed chamber having a relative humidity of 1% or lower while feeding 5.0 l/min of dry air into the chamber to induce heat generation. The temperature of the lower side of the heat generating sheet stack was measured with a thermocouple.

Example 6-2

A stack of heat generating sheets was prepared in the same manner as in Example 6-1, except that holes were made at a distance of 10 mm and at a density of 1 hole/10 cm².

Example 6-3

A stack of heat generating sheets was prepared in the same manner as in Example 6-1, except that cut were made as follows through the molded articles prepared in the same manner as in Example 6-1 in place of the holes.
Making Cuts:

Cuts each measuring 4.5 mm in length were made through the molded sheets using blades of prescribed length. The total length of the cuts made per unit area was 27 mm/cm².

Comparative Example 6-1

A stack of heat generating sheets was prepared in the same manner as in Example 6-1, except that holes were not made.

The thickness, basis weight, air permeance, and heat generation characteristics of the resulting heat generating sheets were measured. The results obtained are shown in Table 6-1. The change in heat generation temperature with time is graphed in FIG. 21.

6-3 having an air permeance of 0.1 to 8 s/(6.4 cm²·300 ml) per 100 g/m² exhibit superior heat generation characteristics to those of Comparative Example 6-1 in maximum temperature reached and duration at 40° C. or higher.

INDUSTRIAL APPLICABILITY

The warming device of sheet form according to the present invention is thin and flexible and exhibits excellent heat generating performance and portability. Therefore, it is suited to wide applications.

The present invention provides a warming device of sheet form that is thin, flexible, agreeable to the touch while in use, and is suited to wide applications.

The present invention provides a heat generating molded article of sheet form having good unity between the heat generating sheet and the air permeable sheet and the air impermeable sheet and exhibiting satisfactory heat generation characteristics and hand.

The present invention provides a heat generating sheet that heats up immediately after the start of use and hardly slides when stacked one on top of another.

The present invention provides a heat generating sheet that is thin and yet exhibits high heat generation characteristics.

The invention claimed is:

1. A warming device of sheet form comprising a plurality of heat generating molded articles of sheet form stacked on top of one another wherein each of said plurality of heat generating molded articles is prepared by papermaking and comprises an oxidizable metal, a moisture retaining agent, and a fibrous material and an air permeable holder holding the plurality of heat generating molded articles of sheet form, the warming device having a thickness of 0.1 to 10 mm and a flexural strength, after heat generation comes to an end, of 0.05 to 3.0 N/cm.

2. The warming device of sheet form according to claim 1, wherein the molded sheet has a thickness of 0.1 to 2.0 mm.

3. The warming device of sheet form according to claim 1, wherein the fibrous material has a CSF of 600 ml or less.

4. The warming device of sheet form according to claim 1, wherein the molded sheet contains 50% by weight or more of the components other than the fibrous material.

5. The warming device of sheet form according to claim 1, wherein the holder comprises an air permeable sheet and an air impermeable sheet joined together and has a surfacing member disposed on the outer surface of each of the air permeable sheet and the air impermeable sheet.

6. The warming device of sheet form according to claim 5, wherein the surfacing member on the air impermeable sheet retains a functional preparation.

TABLE 6-1

|  | Thickness (mm) | Basis weight (g/m²) | Air Permeance (s/300 ml) | Air Permeance per 100 g/m² (s/6.4 cm² · 300 ml) | Heat Generation Characteristics | |
|---|---|---|---|---|---|---|
|  |  |  |  |  | Max. Temp. (° C.) | Duration at 40° C. or Higher (min) |
| Example 6-1 | 0.507 | 404.8 | 4.6 | 1.1 | 46.8 | 41.3 |
| Example 6-2 | 0.499 | 404.8 | 24.4 | 6.0 | 44.5 | 38.3 |
| Example 6-3 | 0.494 | 405.6 | 6 | 1.5 | 47.4 | 39.3 |
| Comp. Example 6-1 | 0.500 | 412 | 35.6 | 8.6 | 42.5 | 31.3 |

Figure 21:
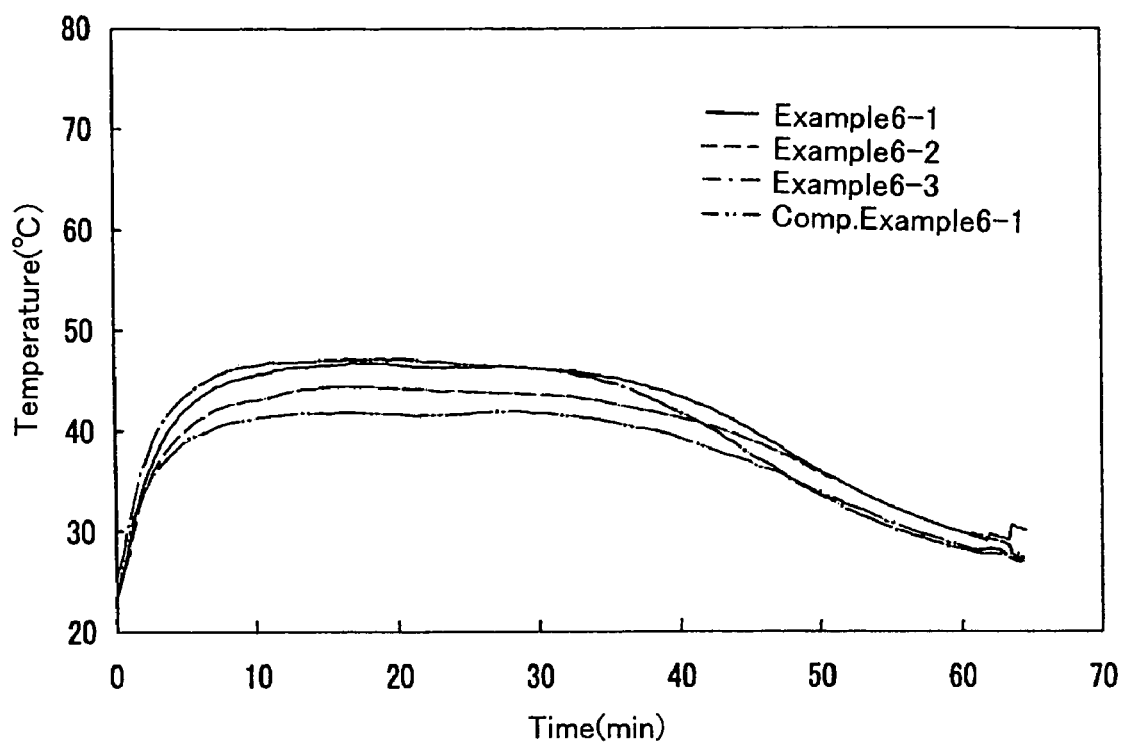
FIG. 21 is a graph showing heat generation characteristics of still other heat generating sheets prepared in Examples and Comparative Examples.

As shown in Table 6-1 and FIG. 21, the heat generating sheets of the present invention, i.e., those of Examples 6-1 to

7. A warming device of sheet form comprising a plurality of heat generating molded articles of sheet form stacked on top of one another wherein each of said plurality of heat generating molded articles is prepared by papermaking and comprises an an oxidizable metal, a moisture retaining agent, and a fibrous material and an air permeable holder holding the plurality of heat generating molded articles of sheet form, the warming device further comprising a non-liquid retentive, heat insulating sheet disposed in the holder, which has a thickness of 1 to 30 mm and said warming device has a flexural strength, after heat generation comes to an end, 0.05 to 3.0 N/cm.

8. The warming device of sheet form according to claim 7, wherein the holder is partly formed of an air permeable sheet, and the heat insulating sheet is not disposed between the air permeable sheet and the molded sheet.

9. A warming device of sheet form comprising a plurality of heat generating molded articles of sheet form stacked on top of one another
wherein each of said plurality of heat generating molded articles is prepared by papermaking and comprises an oxidizable metal, a moisture retaining agent, and a fibrous material and an air permeable holder holding the plurality of heat generating molded articles,
the holder being partly formed of an air permeable sheet,
there being no heat insulating sheet between the air permeable sheet and the molded sheet, and
the warming device having a flexural strength, after heat generation comes to an end, of 0.05 to 3.0 N/cm and having a thickness of 1 to 30 mm.

10. The warming device of sheet form according to claim 1, wherein the content of components other than the fibrous material is from 50% to 98% by weight.

11. The warming device of sheet form according to claim 1, wherein the content of the fibrous material is from 2% to 50% by weight.

12. The warming device of sheet form according to claim 1, wherein said heat generating molded article of sheet form has projections and depressions formed on both sides thereof by embossing.

13. The warming device of sheet form according to claim 1, wherein said heat generating molded article of sheet form has a number of holes or cuts therein.

14. The warming device of sheet form according to claim 7, wherein the content of components other than the fibrous material is from 50% to 98% by weight.

15. The warming device of sheet form according to claim 7, wherein the content of the fibrous material is from 2% to 50% by weight.

16. The warming device of sheet form according to claim 7, wherein said heat generating molded article of sheet form has projections and depressions formed on both sides thereof by embossing.

17. The warming device of sheet form according to claim 7, wherein said heat generating molded article of sheet form has a number of holes or cuts therein.

18. The warming device of sheet form according to claim 9, wherein the content of components other than the fibrous material is from 50% to 98% by weight.

19. The warming device of sheet form according to claim 9, wherein the content of the fibrous material is from 2% to 50% by weight.

20. The warming device of sheet form according to claim 9, wherein said heat generating molded article of sheet form has projections and depressions formed on both sides thereof by embossing.

21. The warming device of sheet form according to claim 9, wherein said heat generating molded article of sheet form has a number of holes or cuts therein.

* * * * *